(12) United States Patent
Bahekar et al.

(10) Patent No.: US 8,841,413 B2
(45) Date of Patent: Sep. 23, 2014

(54) ANTIDIABETIC COMPOUNDS

(75) Inventors: Rajesh H. Bahekar, Ahmedabad (IN);
Braj Bhushan Lohray, Ahmedabad (IN); Vidya Bhushan Lohray, Ahmedabad (IN); Mukul R. Jain, Ahmedabad (IN); Kaushik M. Banerjee, Ahmedabad (IN); Pankaj Ramanbhai Patel, Ahmedabad (IN)

(73) Assignee: Cadila Healthcare Limited, Amedadabad (IN)

( * ) Notice: Subject to any disclaimer, the term of this patent is extended or adjusted under 35 U.S.C. 154(b) by 1573 days.

(21) Appl. No.: 12/311,448

(22) PCT Filed: Sep. 28, 2007

(86) PCT No.: PCT/IN2007/000457
§ 371 (c)(1),
(2), (4) Date: Nov. 19, 2009

(87) PCT Pub. No.: WO2008/062457
PCT Pub. Date: May 29, 2008

(65) Prior Publication Data
US 2013/0225488 A1   Aug. 29, 2013

(30) Foreign Application Priority Data

Oct. 3, 2006   (IN) .................. 1632/MUM/2006
Nov. 30, 2006   (IN) .................. 1965/MUM/2006
Mar. 6, 2007   (IN) .................... 423/MUM/2007

(51) Int. Cl.
*C07K 7/08* (2006.01)
*C07K 7/06* (2006.01)
*C07K 14/605* (2006.01)

(52) U.S. Cl.
CPC ... *C07K 7/08* (2013.01); *C07K 7/06* (2013.01); *C07K 14/605* (2013.01)
USPC .......... 530/323; 530/300; 530/327; 530/326; 514/1.1; 514/6.8; 514/6.9; 514/5.8; 514/21.4

(58) Field of Classification Search
CPC ............ C07K 1/006; C07K 7/06; C07K 7/04; C07K 7/00; A61K 6/00; A61K 38/08; A61K 38/04; A61K 38/00
See application file for complete search history.

(56) References Cited

U.S. PATENT DOCUMENTS 6,864,069 B2   3/2005   Pan et al.
2004/0005664 A1*  1/2004   Meyers et al. ............... 435/69.1

FOREIGN PATENT DOCUMENTS

WO   03/033671   4/2003
WO   2006/014287   2/2006

OTHER PUBLICATIONS

Ahn, Jung-Mo, et al. "Development of Potent Truncated Glucagon Antagonists." *Journal of Medicinal Chemistry* (2001) vol. 44, No. 9, pp. 1372-1379.

* cited by examiner

*Primary Examiner* — Karlheinz R Skowronek
*Assistant Examiner* — Catherine Mader
(74) *Attorney, Agent, or Firm* — Ladas & Parry LLP

(57) ABSTRACT

The present invention provides novel peptidomimetics, of formula (I), which primarily act as glucose dependent insulin secretagogues. Furthermore, it was found that these peptidomimetics showed glucagon receptor antagonistic activity, along with the GLP-1 receptor agonistic activity.

$$A-Z_1-Z_2-Z_3-Z_4-Z_5-Z_6-Z_7-Z_8-Z_9-Z_{10}-Z_{11}-B \quad (I)$$

20 Claims, 7 Drawing Sheets

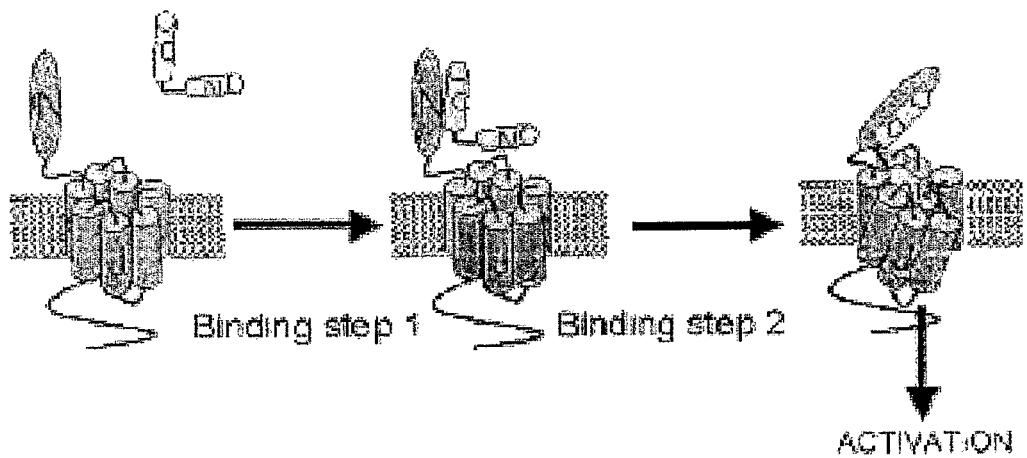
Figure 1: Two-domain model for interaction of peptide ligands with class B GPCRs
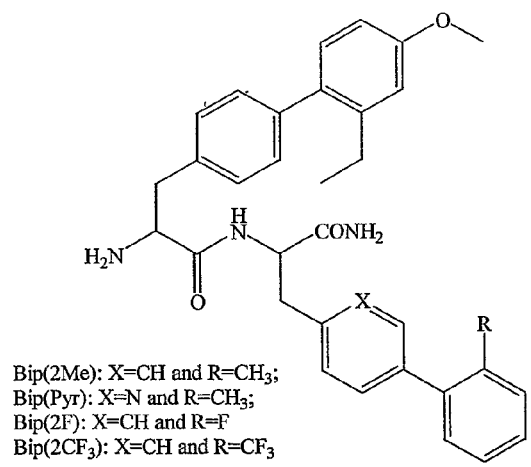
Bip(2Me): X=CH and R=CH₃;
Bip(Pyr): X=N and R=CH₃;
Bip(2F): X=CH and R=F
Bip(2CF₃): X=CH and R=CF₃
Figure 2: Structures of dipeptides which showed *in vitro* Glucagon / GLP-1 antagonistic activity

Figure 3: *In vitro* Human Glucagon and GLP-1 receptor antagonistic activity of dipeptide (Bip(OMe)-Bip(2Me)).

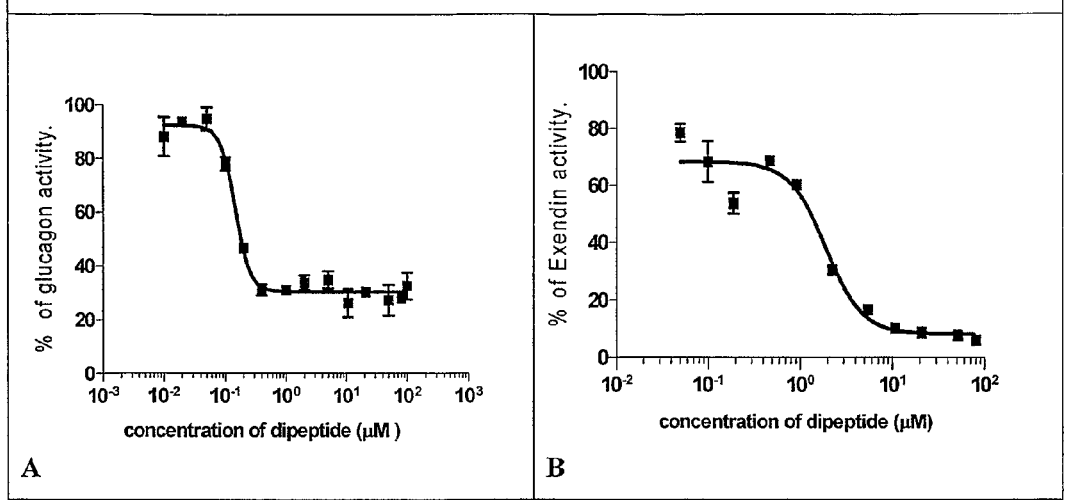

Figure A showed % inhibition of glucagon peptide activity in human glucagon receptor overexpressed in CHO cell lines, incubated with different concentration of dipeptide; Figure B showed % inhibition of EX-4 peptide activity in human GLP-1 receptor overexpressed in CHO cell lines, incubated with different concentration of dipeptide

Figure 4: *In vitro* Human Glucagon receptor antagonistic activity and GLP-1 receptor agonistic activity with Seq. ID. No.5.

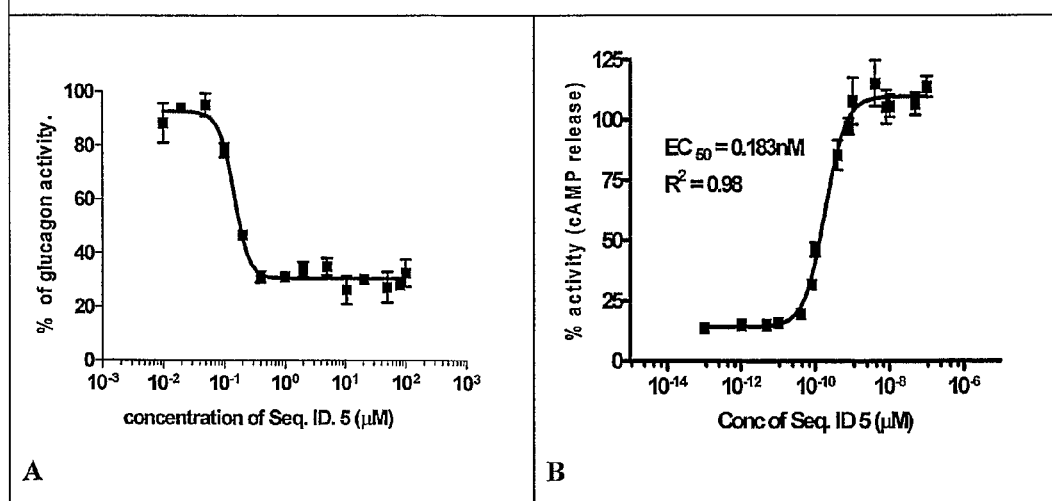

Figure A showed % inhibition of glucagon peptide activity in human glucagon receptor overexpressed in CHO cell lines, incubated with different concentration of Seq. ID 5; Figure B showed % activity (cAMP release) wrt Ex-4, of Seq. ID 5, in human GLP-1 receptor overexpressed in CHO cell lines.

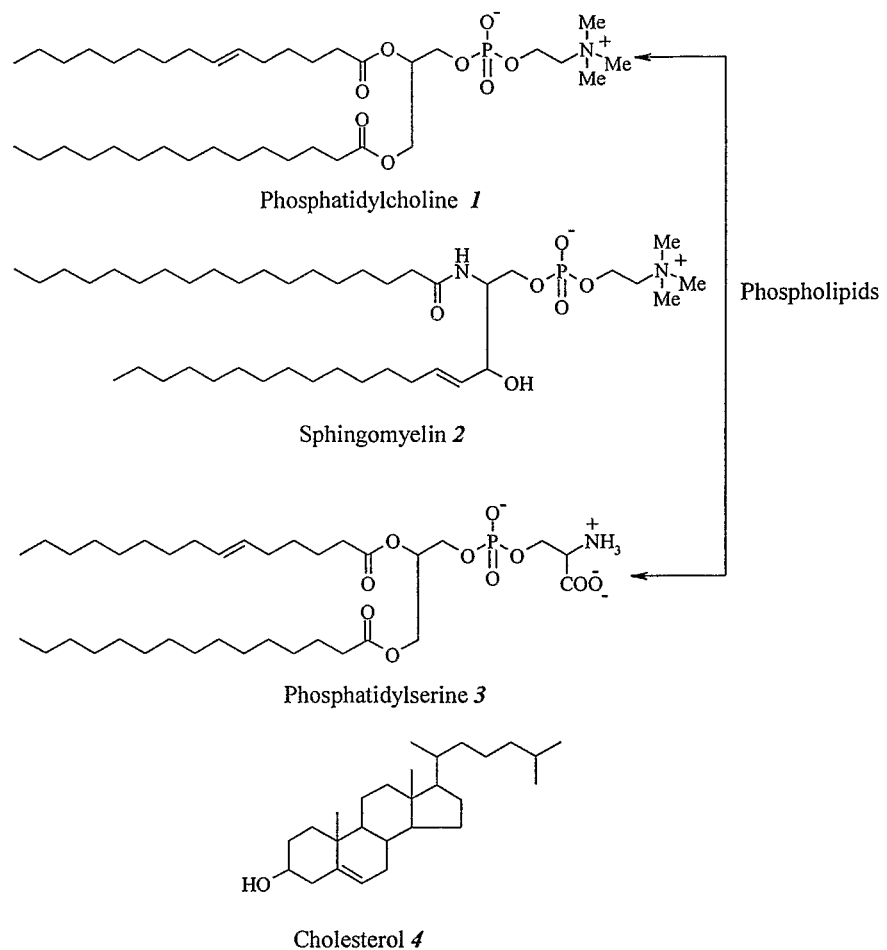
Figure 5: Some of the structural components of epithelial membrane

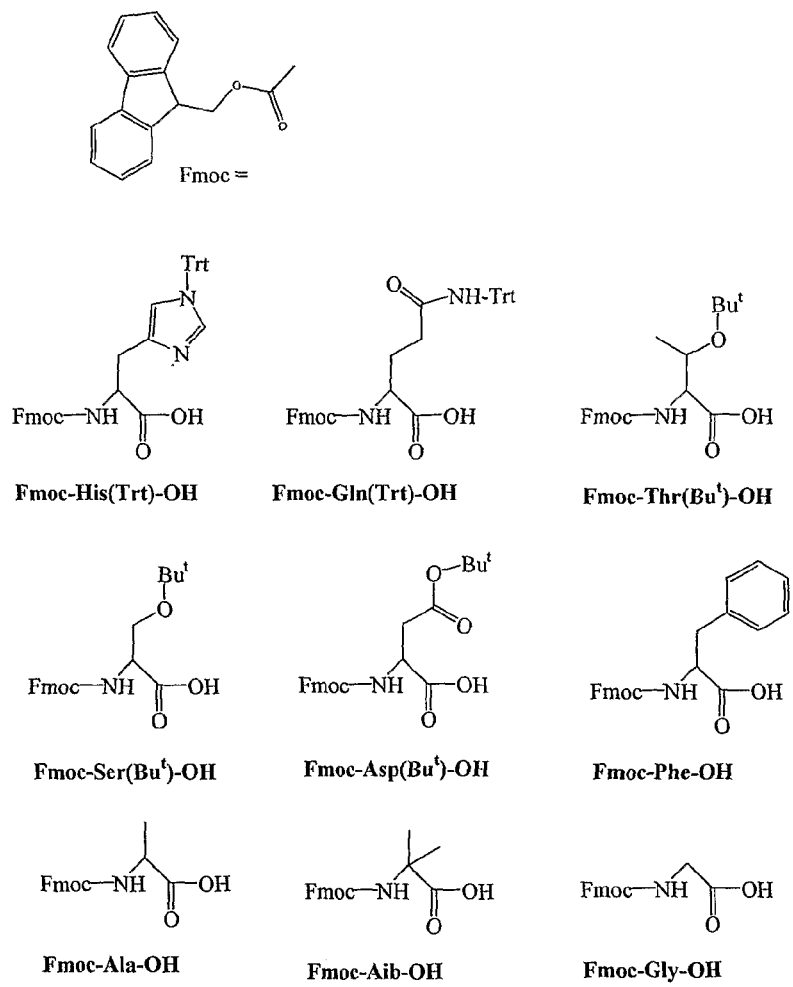
Figure 6: Examples of orthogonally protected amino acids used in Fmoc based-solid phase peptide synthesis (SPPS) of peptidomimetics.

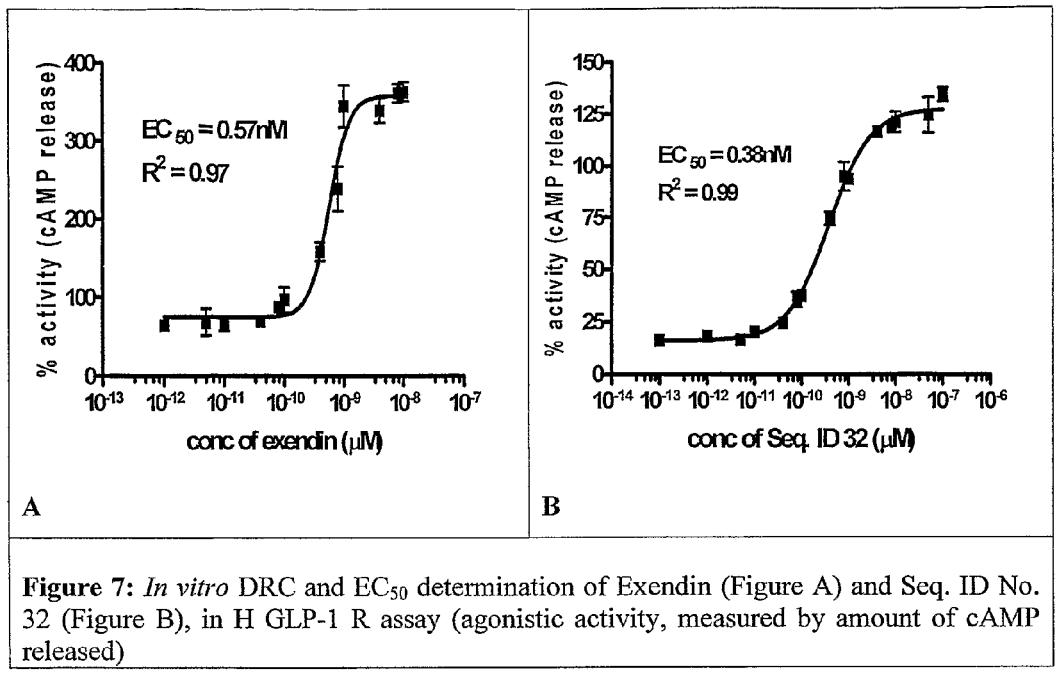

Figure 7: *In vitro* DRC and $EC_{50}$ determination of Exendin (Figure A) and Seq. ID No. 32 (Figure B), in H GLP-1 R assay (agonistic activity, measured by amount of cAMP released)

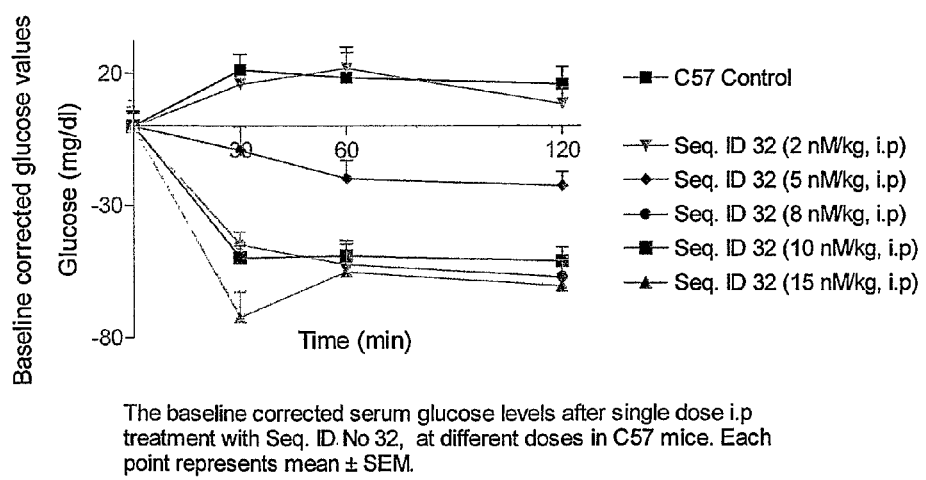

The baseline corrected serum glucose levels after single dose i.p treatment with Seq. ID. No 32, at different doses in C57 mice. Each point represents mean ± SEM.

Figure 8: *In vivo* glucose reduction in C57 mice, with Seq. ID No. 32, after intraperitonial (i.p) administration (dose response curve (DRC))

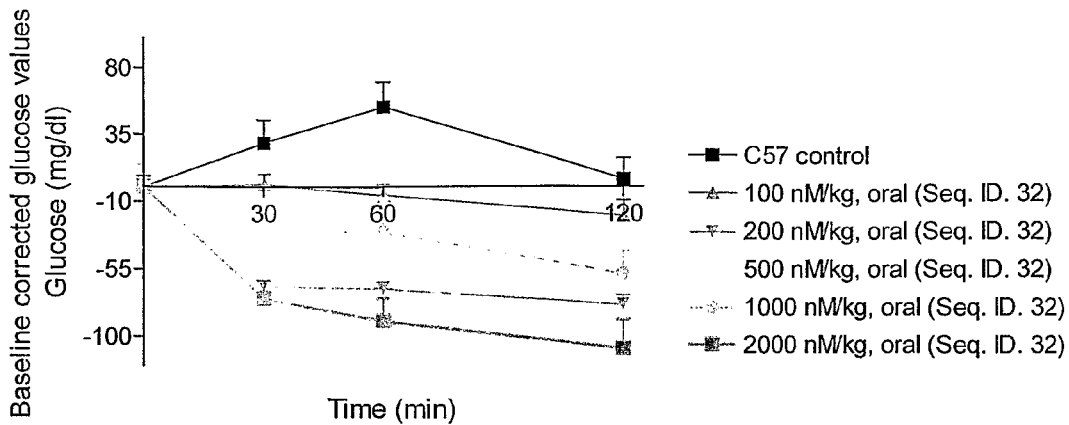
Figure 9: *In vivo* glucose reduction in C57 mice, with Seq. ID No. 32, after oral (p.o) administration (dose response curve (DRC))
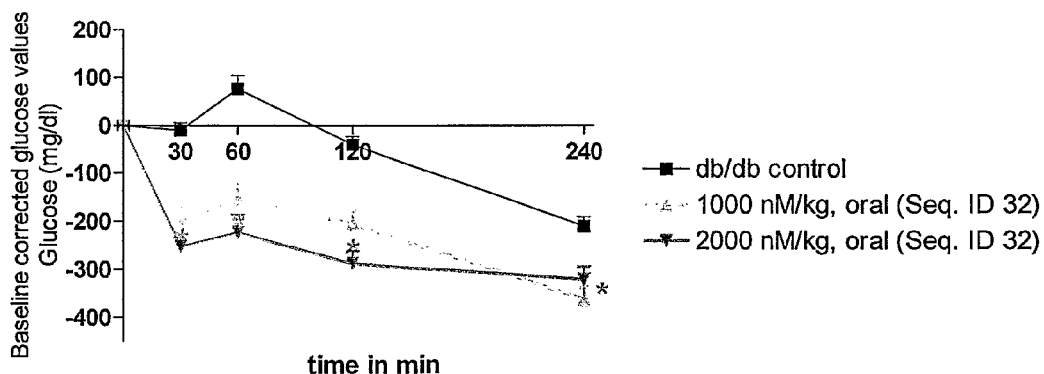
Figure 10: *In vivo* glucose reduction in db/db mice, with Seq. ID No. 32, after oral (p.o) administration.

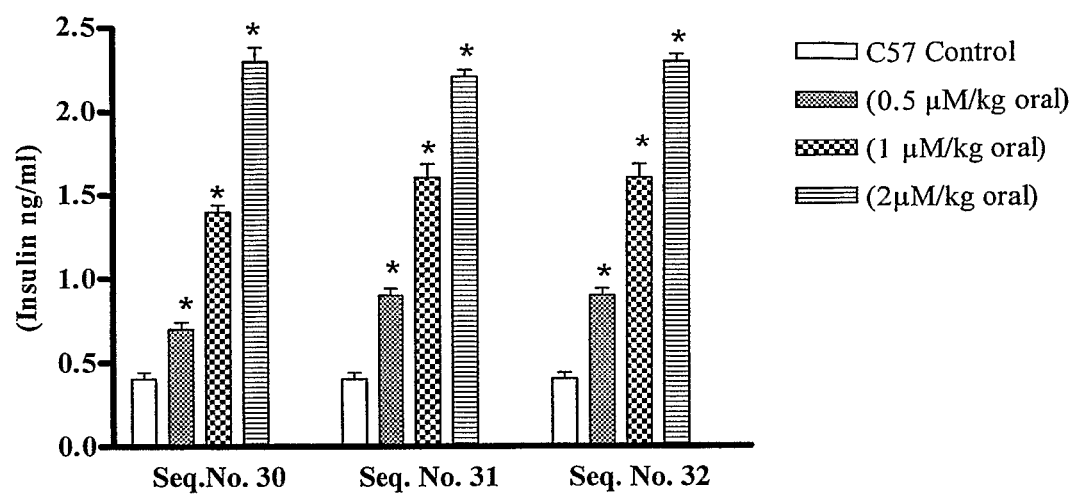
Figure 11: The serum insulin levels after single oral administration of vehicles / test compounds (Seq. ID. No. 30, 31 and 32), in C57BL/6J mice (*in vivo*).

SEQUENCE LISTING

```
<160> NUMBER OF SEQ ID NOS: 196

<210> SEQ ID NO 1
<211> LENGTH: 29
<212> TYPE: PRT
<213> ORGANISM: Artificial Sequence
<220> FEATURE:
<223> OTHER INFORMATION: Synthetic pepetide

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 30
<212> TYPE: PRT
<213> ORGANISM: Artificial Sequence
<220> FEATURE:
<223> OTHER INFORMATION: Synthetic peptide

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

His Ala Glu Gly Thr Phe Thr Ser Asp
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

His Ser Gln Gly Thr Phe Thr Ser Asp
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2Me)

<400> SEQUENCE: 5

His Ser Gln Gly Thr Phe Thr Ser Asp Xaa Xaa
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 6

His Ser Gln Gly Thr Phe Thr Ser Asp Xaa Xaa
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2F)

<400> SEQUENCE: 7

His Ser Gln Gly Thr Phe Thr Ser Asp Xaa Xaa
1               5                   10

<210> SEQ ID NO 8
```

-continued

```
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 8

His Ser Gln Gly Thr Phe Thr Ser Asp Xaa Xaa
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2Me)

<400> SEQUENCE: 9

His Ala Gln Gly Thr Phe Thr Ser Asp Xaa Xaa
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 10

His Ala Gln Gly Thr Phe Thr Ser Asp Xaa Xaa
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 11
```

-continued

His Ala Gln Gly Thr Phe Thr Ser Asp Xaa Xaa
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 12

His Ala Gln Gly Thr Phe Thr Ser Asp Xaa Xaa
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2Me)

<400> SEQUENCE: 13

His Xaa Gln Gly Thr Phe Thr Ser Asp Xaa Xaa
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 14

His Xaa Gln Gly Thr Phe Thr Ser Asp Xaa Xaa
1               5                   10

<210> SEQ ID NO 15
<211> LENGTH: 11
<212> TYPE: PRT
<213> ORGANISM: Artificial Sequence

```
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 15

His Xaa Gln Gly Thr Phe Thr Ser Asp Xaa Xaa
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MOD_RES
<222> LOCATION: (10)..(10)
<223> OTHER INFORMATION: Xaa is Bip(OMe) = Biphenylalanine(OMe)
<220> FEATURE:
<221> NAME/KEY: MOD_RES
<222> LOCATION: (11)..(11)
<223> OTHER INFORMATION: Xaa is Biphenylalanine(2-Trifluoromethyl)

<400> SEQUENCE: 16

His Xaa Gln Gly Thr Phe Thr Ser Asp Xaa Xaa
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 17

His Xaa Gln Gly Thr Phe Thr Ser Asp Xaa Xaa
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
```

```
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 18

His Xaa Gln Gly Thr Phe Thr Ser Asp Xaa Xaa
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 19

His Xaa Gln Gly Thr Phe Thr Ser Asp Xaa Xaa
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 20

His Xaa Gln Gly Thr Phe Thr Ser Asp Xaa Xaa
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
```

```
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 21

His Ser Gln Gly Thr Xaa Thr Ser Asp Xaa Xaa
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 22

His Ser Gln Gly Thr Xaa Thr Ser Asp Xaa Xaa
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 23

His Ser Gln Gly Thr Xaa Thr Ser Asp Xaa Xaa
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
```

```
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 24

His Ser Gln Gly Thr Xaa Thr Ser Asp Xaa Xaa
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 25

His Ala Gln Gly Thr Xaa Thr Ser Asp Xaa Xaa
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 26

His Ala Gln Gly Thr Xaa Thr Ser Asp Xaa Xaa
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
<223> OTHER INFORMATION: Xaa is alpha-Me-2F-Phe =
```

```
        alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 27

His Ala Gln Gly Thr Xaa Thr Ser Asp Xaa Xaa
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
<223> OTHER INFORMATION: Xaa is alpha-Me-2F-Phe =
        alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 28

His Ala Gln Gly Thr Xaa Thr Ser Asp Xaa Xaa
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (6)..(6)
<223> OTHER INFORMATION: Xaa is alpha-Me-2F-Phe =
        alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 29

His Xaa Gln Gly Thr Xaa Thr Ser Asp Xaa Xaa
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
```

```
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 30

His Xaa Gln Gly Thr Xaa Thr Ser Asp Xaa Xaa
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 31

His Xaa Gln Gly Thr Xaa Thr Ser Asp Xaa Xaa
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 32
```

His Xaa Gln Gly Thr Xaa Thr Ser Asp Xaa Xaa
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 33

His Xaa Gln Gly Thr Xaa Thr Ser Asp Xaa Xaa
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 34

His Xaa Gln Gly Thr Xaa Thr Ser Asp Xaa Xaa
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE

```
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 35

His Xaa Gln Gly Thr Xaa Thr Ser Asp Xaa Xaa
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 36

His Xaa Gln Gly Thr Xaa Thr Ser Asp Xaa Xaa
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 37

His Ser Gln Gly Thr Xaa Thr Ser Asp Xaa Xaa
1               5                   10

<210> SEQ ID NO 38
<211> LENGTH: 11
<212> TYPE: PRT
<213> ORGANISM: Artificial Sequence
<220> FEATURE:
```

```
<223> OTHER INFORMATION: Synthetic peptidomimetic
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 38

His Ser Gln Gly Thr Xaa Thr Ser Asp Xaa Xaa
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 39

His Ser Gln Gly Thr Xaa Thr Ser Asp Xaa Xaa
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 40

His Ser Gln Gly Thr Xaa Thr Ser Asp Xaa Xaa
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
```

```
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 41

His Ala Gln Gly Thr Xaa Thr Ser Asp Xaa Xaa
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 42

His Ala Gln Gly Thr Xaa Thr Ser Asp Xaa Xaa
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 43

His Ala Gln Gly Thr Xaa Thr Ser Asp Xaa Xaa
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
```

<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 44

His Ala Gln Gly Thr Xaa Thr Ser Asp Xaa Xaa
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 45

His Xaa Gln Gly Thr Xaa Thr Ser Asp Xaa Xaa
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 46

His Xaa Gln Gly Thr Xaa Thr Ser Asp Xaa Xaa
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)

```
<223> OTHER INFORMATION: Xaa is Aib = alpha-Aminoisobutyric Acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 47

His Xaa Gln Gly Thr Xaa Thr Ser Asp Xaa Xaa
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 48

His Xaa Gln Gly Thr Xaa Thr Ser Asp Xaa Xaa
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 49

His Xaa Gln Gly Thr Xaa Thr Ser Asp Xaa Xaa
1               5                   10
```

```
<210> SEQ ID NO 50
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 50

His Xaa Gln Gly Thr Xaa Thr Ser Asp Xaa Xaa
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 51

His Xaa Gln Gly Thr Xaa Thr Ser Asp Xaa Xaa
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
```

```
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 52

His Xaa Gln Gly Thr Xaa Thr Ser Asp Xaa Xaa
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 53

His Ser Xaa Gly Thr Phe Thr Ser Asp Xaa Xaa
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 54

His Ser Xaa Gly Thr Phe Thr Ser Asp Xaa Xaa
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)
```

-continued

<400> SEQUENCE: 55

His Ser Xaa Gly Thr Phe Thr Ser Asp Xaa Xaa
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 56

His Ser Xaa Gly Thr Phe Thr Ser Asp Xaa Xaa
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 57

His Ala Xaa Gly Thr Phe Thr Ser Asp Xaa Xaa
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 58

His Ala Xaa Gly Thr Phe Thr Ser Asp Xaa Xaa

```
1               5                   10
```

```
<210> SEQ ID NO 59
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 59

His Ala Xaa Gly Thr Phe Thr Ser Asp Xaa Xaa
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 60

His Ala Xaa Gly Thr Phe Thr Ser Asp Xaa Xaa
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 61

His Xaa Xaa Gly Thr Phe Thr Ser Asp Xaa Xaa
```

<210> SEQ ID NO 62
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 62

His Xaa Xaa Gly Thr Phe Thr Ser Asp Xaa Xaa
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 63

His Xaa Xaa Gly Thr Phe Thr Ser Asp Xaa Xaa
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)

```
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 64

His Xaa Xaa Gly Thr Phe Thr Ser Asp Xaa Xaa
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 65

His Xaa Xaa Gly Thr Phe Thr Ser Asp Xaa Xaa
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 66

His Xaa Xaa Gly Thr Phe Thr Ser Asp Xaa Xaa
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
```

```
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 67

His Xaa Xaa Gly Thr Phe Thr Ser Asp Xaa Xaa
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 68

His Xaa Xaa Gly Thr Phe Thr Ser Asp Xaa Xaa
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 69

His Ser Xaa Gly Thr Xaa Thr Ser Asp Xaa Xaa
```

<210> SEQ ID NO 70
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 70

His Ser Xaa Gly Thr Xaa Thr Ser Asp Xaa Xaa
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 71

His Ser Xaa Gly Thr Xaa Thr Ser Asp Xaa Xaa
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:

```
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 72

His Ser Xaa Gly Thr Xaa Thr Ser Asp Xaa Xaa
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 73

His Ala Xaa Gly Thr Xaa Thr Ser Asp Xaa Xaa
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 74

His Ala Xaa Gly Thr Xaa Thr Ser Asp Xaa Xaa
1               5                   10

<210> SEQ ID NO 75
<211> LENGTH: 11
<212> TYPE: PRT
<213> ORGANISM: Artificial Sequence
<220> FEATURE:
```

```
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 75

His Ala Xaa Gly Thr Xaa Thr Ser Asp Xaa Xaa
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 76

His Ala Xaa Gly Thr Xaa Thr Ser Asp Xaa Xaa
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
```

```
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 77

His Xaa Xaa Gly Thr Xaa Thr Ser Asp Xaa Xaa
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 78

His Xaa Xaa Gly Thr Xaa Thr Ser Asp Xaa Xaa
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 79

His Xaa Xaa Gly Thr Xaa Thr Ser Asp Xaa Xaa
1               5                   10

<210> SEQ ID NO 80
```

```
-continued

<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 80

His Xaa Xaa Gly Thr Xaa Thr Ser Asp Xaa Xaa
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 81

His Xaa Xaa Gly Thr Xaa Thr Ser Asp Xaa Xaa
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
```

```
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 82

His Xaa Xaa Gly Thr Xaa Thr Ser Asp Xaa Xaa
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 83

His Xaa Xaa Gly Thr Xaa Thr Ser Asp Xaa Xaa
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
```

```
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 84

His Xaa Xaa Gly Thr Xaa Thr Ser Asp Xaa Xaa
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 85

His Ser Xaa Gly Thr Xaa Thr Ser Asp Xaa Xaa
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 86

His Ser Xaa Gly Thr Xaa Thr Ser Asp Xaa Xaa
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic peptidomimetic
```

```
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 87

His Ser Xaa Gly Thr Xaa Thr Ser Asp Xaa Xaa
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 88

His Ser Xaa Gly Thr Xaa Thr Ser Asp Xaa Xaa
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 89

His Ala Xaa Gly Thr Xaa Thr Ser Asp Xaa Xaa
1               5                   10
```

```
<210> SEQ ID NO 90
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 90

His Ala Xaa Gly Thr Xaa Thr Ser Asp Xaa Xaa
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 91

His Ala Xaa Gly Thr Xaa Thr Ser Asp Xaa Xaa
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
```

```
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 92

His Ala Xaa Gly Thr Xaa Thr Ser Asp Xaa Xaa
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 93

His Xaa Xaa Gly Thr Xaa Thr Ser Asp Xaa Xaa
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 94

His Xaa Xaa Gly Thr Xaa Thr Ser Asp Xaa Xaa
1               5                   10

<210> SEQ ID NO 95
<211> LENGTH: 11
<212> TYPE: PRT
```

```
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 95

His Xaa Xaa Gly Thr Xaa Thr Ser Asp Xaa Xaa
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 96

His Xaa Xaa Gly Thr Xaa Thr Ser Asp Xaa Xaa
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
```

```
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 97

His Xaa Xaa Gly Thr Xaa Thr Ser Asp Xaa Xaa
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 98

His Xaa Xaa Gly Thr Xaa Thr Ser Asp Xaa Xaa
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)
```

```
<400> SEQUENCE: 99

His Xaa Xaa Gly Thr Xaa Thr Ser Asp Xaa Xaa
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (3)..(3)
<223> OTHER INFORMATION: Xaa is CNB = 2-amino-4-cyano-butyric acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 100

His Xaa Xaa Gly Thr Xaa Thr Ser Asp Xaa Xaa
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 101

His Ser Gln Xaa Thr Phe Thr Ser Asp Xaa Xaa
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
```

```
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 102

His Ser Gln Xaa Thr Phe Thr Ser Asp Xaa Xaa
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 103

His Ser Gln Xaa Thr Phe Thr Ser Asp Xaa Xaa
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 104

His Ser Gln Xaa Thr Phe Thr Ser Asp Xaa Xaa
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
```

```
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 105

His Ala Gln Xaa Thr Phe Thr Ser Asp Xaa Xaa
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 106

His Ala Gln Xaa Thr Phe Thr Ser Asp Xaa Xaa
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 107

His Ala Gln Xaa Thr Phe Thr Ser Asp Xaa Xaa
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
```

```
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 108

His Ala Gln Xaa Thr Phe Thr Ser Asp Xaa Xaa
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 109

His Xaa Gln Xaa Thr Phe Thr Ser Asp Xaa Xaa
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 110

His Xaa Gln Xaa Thr Phe Thr Ser Asp Xaa Xaa
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
```

```
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 111

His Xaa Gln Xaa Thr Phe Thr Ser Asp Xaa Xaa
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 112

His Xaa Gln Xaa Thr Phe Thr Ser Asp Xaa Xaa
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 113
```

His Xaa Gln Xaa Thr Phe Thr Ser Asp Xaa Xaa
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 114

His Xaa Gln Xaa Thr Phe Thr Ser Asp Xaa Xaa
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 115

His Xaa Gln Xaa Thr Phe Thr Ser Asp Xaa Xaa
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:

```
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 116

His Xaa Gln Xaa Thr Phe Thr Ser Asp Xaa Xaa
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 117

His Ser Gln Xaa Thr Xaa Thr Ser Asp Xaa Xaa
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 118

His Ser Gln Xaa Thr Xaa Thr Ser Asp Xaa Xaa
1               5                   10
```

```
<210> SEQ ID NO 119
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(1)
<223> OTHER INFORMATION: Xaa is Bip(2F) = Biphenylalanine(2-Fluoro)
<220> FEATURE:
<221> NAME/KEY: misc_feature
<222> LOCATION: (11)..(11)
<223> OTHER INFORMATION: Xaa can be any naturally occurring amino acid

<400> SEQUENCE: 119

His Ser Gln Xaa Thr Xaa Thr Ser Asp Xaa Xaa
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 120

His Ser Gln Xaa Thr Xaa Thr Ser Asp Xaa Xaa
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
```

```
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 121

His Ala Gln Xaa Thr Xaa Thr Ser Asp Xaa Xaa
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 122

His Ala Gln Xaa Thr Xaa Thr Ser Asp Xaa Xaa
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 123

His Ala Gln Xaa Thr Xaa Thr Ser Asp Xaa Xaa
```

<210> SEQ ID NO 124
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
    acid
<220> FEATURE:
<221> NAME/KEY: MISC_FEATURE
<222> LOCATION: (6)..(6)
<223> OTHER INFORMATION: Xaa is alpha-Me-2F-Phe =
    alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 124

His Ala Gln Xaa Thr Xaa Thr Ser Asp Xaa Xaa
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
    acid
<220> FEATURE:
<221> NAME/KEY: MISC_FEATURE
<222> LOCATION: (6)..(6)
<223> OTHER INFORMATION: Xaa is alpha-Me-2F-Phe =
    alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 125

His Xaa Gln Xaa Thr Xaa Thr Ser Asp Xaa Xaa
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid

```
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 126

His Xaa Gln Xaa Thr Xaa Thr Ser Asp Xaa Xaa
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 127

His Xaa Gln Xaa Thr Xaa Thr Ser Asp Xaa Xaa
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
```

```
        alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 128

His Xaa Gln Xaa Thr Xaa Thr Ser Asp Xaa Xaa
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
        acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
        acid
<220> FEATURE:
<221> NAME/KEY: MISC_FEATURE
<222> LOCATION: (6)..(6)
<223> OTHER INFORMATION: Xaa is alpha-Me-2F-Phe =
        alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 129

His Xaa Gln Xaa Thr Xaa Thr Ser Asp Xaa Xaa
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
        acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
        acid
<220> FEATURE:
<221> NAME/KEY: MISC_FEATURE
<222> LOCATION: (6)..(6)
<223> OTHER INFORMATION: Xaa is alpha-Me-2F-Phe =
        alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
```

-continued

```
<222> LOCATION: (11)..(11)
<223> OTHER INFORMATION: Xaa is Bip(Pyr) = Biphenylalanine(Pyr)

<400> SEQUENCE: 130

His Xaa Gln Xaa Thr Xaa Thr Ser Asp Xaa Xaa
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 131

His Xaa Gln Xaa Thr Xaa Thr Ser Asp Xaa Xaa
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 132

His Xaa Gln Xaa Thr Xaa Thr Ser Asp Xaa Xaa
1               5                   10
```

```
<210> SEQ ID NO 133
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 133

His Ser Gln Xaa Thr Xaa Thr Ser Asp Xaa Xaa
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 134

His Ser Gln Xaa Thr Xaa Thr Ser Asp Xaa Xaa
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
```

```
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(1)
<223> OTHER INFORMATION: Xaa is Bip(2F) = Biphenylalanine(2-Fluoro)
<220> FEATURE:
<221> NAME/KEY: misc_feature
<222> LOCATION: (11)..(11)
<223> OTHER INFORMATION: Xaa can be any naturally occurring amino acid

<400> SEQUENCE: 135

His Ser Gln Xaa Thr Xaa Thr Ser Asp Xaa Xaa
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 136

His Ser Gln Xaa Thr Xaa Thr Ser Asp Xaa Xaa
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 137

His Ala Gln Xaa Thr Xaa Thr Ser Asp Xaa Xaa
```

```
<210> SEQ ID NO 138
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 138

His Ala Gln Xaa Thr Xaa Thr Ser Asp Xaa Xaa
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 139

His Ala Gln Xaa Thr Xaa Thr Ser Asp Xaa Xaa
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
```

```
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 140

His Ala Gln Xaa Thr Xaa Thr Ser Asp Xaa Xaa
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 141

His Xaa Gln Xaa Thr Xaa Thr Ser Asp Xaa Xaa
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 142

His Xaa Gln Xaa Thr Xaa Thr Ser Asp Xaa Xaa
```

```
1               5                    10

<210> SEQ ID NO 143
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 143

His Xaa Gln Xaa Thr Xaa Thr Ser Asp Xaa Xaa
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 144

His Xaa Gln Xaa Thr Xaa Thr Ser Asp Xaa Xaa
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
```

```
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 145

His Xaa Gln Xaa Thr Xaa Thr Ser Asp Xaa Xaa
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 146

His Xaa Gln Xaa Thr Xaa Thr Ser Asp Xaa Xaa
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
```

```
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 147

His Xaa Gln Xaa Thr Xaa Thr Ser Asp Xaa Xaa
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (4)..(4)
<223> OTHER INFORMATION: Xaa is ACP = 1-aminocyclopropane carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 148

His Xaa Gln Xaa Thr Xaa Thr Ser Asp Xaa Xaa
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 149

His Ser Gln Gly Xaa Phe Thr Ser Asp Xaa Xaa
1               5                   10
```

```
<210> SEQ ID NO 150
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (10)..(01)
<223> OTHER INFORMATION: Xaa is Bip(OMe) = Biphenylalanine(OMe)
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 150

His Ser Gln Gly Xaa Phe Thr Ser Asp Xaa Xaa
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 151

His Ser Gln Gly Xaa Phe Thr Ser Asp Xaa Xaa
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 152

His Ser Gln Gly Xaa Phe Thr Ser Asp Xaa Xaa
```

```
<210> SEQ ID NO 153
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 153

His Ala Gln Gly Xaa Phe Thr Ser Asp Xaa Xaa
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 154

His Ala Gln Gly Xaa Phe Thr Ser Asp Xaa Xaa
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 155

His Ala Gln Gly Xaa Phe Thr Ser Asp Xaa Xaa
1               5                   10
```

<210> SEQ ID NO 156
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
    acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 156

His Ala Gln Gly Xaa Phe Thr Ser Asp Xaa Xaa
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
    acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 157

His Xaa Gln Gly Xaa Phe Thr Ser Asp Xaa Xaa
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
    acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE

```
<222> LOCATION: (11)..(11)
<223> OTHER INFORMATION: Xaa is Bip(Pyr) = Biphenylalanine(Pyr)

<400> SEQUENCE: 158

His Xaa Gln Gly Xaa Phe Thr Ser Asp Xaa Xaa
1               5                   10

<210> SEQ ID NO 159
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 159

His Xaa Gln Gly Xaa Phe Thr Ser Asp Xaa Xaa
1               5                   10

<210> SEQ ID NO 160
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 160

His Xaa Gln Gly Xaa Phe Thr Ser Asp Xaa Xaa
1               5                   10

<210> SEQ ID NO 161
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
```

```
                           acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 161

His Xaa Gln Gly Xaa Phe Thr Ser Asp Xaa Xaa
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 162

His Xaa Gln Gly Xaa Phe Thr Ser Asp Xaa Xaa
1               5                   10

<210> SEQ ID NO 163
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 163
```

His Xaa Gln Gly Xaa Phe Thr Ser Asp Xaa Xaa
1               5                   10

<210> SEQ ID NO 164
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 164

His Xaa Gln Gly Xaa Phe Thr Ser Asp Xaa Xaa
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 165

His Ser Gln Gly Xaa Xaa Thr Ser Asp Xaa Xaa
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE

```
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 166

His Ser Gln Gly Xaa Xaa Thr Ser Asp Xaa Xaa
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 167

His Ser Gln Gly Xaa Xaa Thr Ser Asp Xaa Xaa
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 168

His Ser Gln Gly Xaa Xaa Thr Ser Asp Xaa Xaa
1               5                   10
```

```
<210> SEQ ID NO 169
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 169

His Ala Gln Gly Xaa Xaa Thr Ser Asp Xaa Xaa
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 170

His Ala Gln Gly Xaa Xaa Thr Ser Asp Xaa Xaa
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
```

```
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 171

His Ala Gln Gly Xaa Xaa Thr Ser Asp Xaa Xaa
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 172

His Ala Gln Gly Xaa Xaa Thr Ser Asp Xaa Xaa
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 173

His Xaa Gln Gly Xaa Xaa Thr Ser Asp Xaa Xaa
1               5                   10
```

```
<210> SEQ ID NO 174
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 174

His Xaa Gln Gly Xaa Xaa Thr Ser Asp Xaa Xaa
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 175

His Xaa Gln Gly Xaa Xaa Thr Ser Asp Xaa Xaa
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
```

<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 176

His Xaa Gln Gly Xaa Xaa Thr Ser Asp Xaa Xaa
1               5                   10

<210> SEQ ID NO 177
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 177

His Xaa Gln Gly Xaa Xaa Thr Ser Asp Xaa Xaa
1               5                   10

<210> SEQ ID NO 178
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic

```
            acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 178

His Xaa Gln Gly Xaa Xaa Thr Ser Asp Xaa Xaa
1               5                   10

<210> SEQ ID NO 179
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 179

His Xaa Gln Gly Xaa Xaa Thr Ser Asp Xaa Xaa
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is alpha-Me-2F-Phe =
      alpha-methyl-2-fluorophenylalanine
<220> FEATURE:
```

```
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 180

His Xaa Gln Gly Xaa Xaa Thr Ser Asp Xaa Xaa
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 181

His Ser Gln Gly Xaa Xaa Thr Ser Asp Xaa Xaa
1               5                   10

<210> SEQ ID NO 182
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 182

His Ser Gln Gly Xaa Xaa Thr Ser Asp Xaa Xaa
1               5                   10

<210> SEQ ID NO 183
<211> LENGTH: 11
<212> TYPE: PRT
<213> ORGANISM: Artificial Sequence
<220> FEATURE:
```

```
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 183

His Ser Gln Gly Xaa Xaa Thr Ser Asp Xaa Xaa
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 184

His Ser Gln Gly Xaa Xaa Thr Ser Asp Xaa Xaa
1               5                   10

<210> SEQ ID NO 185
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)
```

```
<400> SEQUENCE: 185

His Ala Gln Gly Xaa Xaa Thr Ser Asp Xaa Xaa
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 186

His Ala Gln Gly Xaa Xaa Thr Ser Asp Xaa Xaa
1               5                   10

<210> SEQ ID NO 187
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 187

His Ala Gln Gly Xaa Xaa Thr Ser Asp Xaa Xaa
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
```

```
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 188

His Ala Gln Gly Xaa Xaa Thr Ser Asp Xaa Xaa
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 189

His Xaa Gln Gly Xaa Xaa Thr Ser Asp Xaa Xaa
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)
```

<400> SEQUENCE: 190

His Xaa Gln Gly Xaa Xaa Thr Ser Asp Xaa Xaa
1               5                   10

<210> SEQ ID NO 191
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 191

His Xaa Gln Gly Xaa Xaa Thr Ser Asp Xaa Xaa
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is Aib = alpha-Aminoisobutyric Acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 192

His Xaa Gln Gly Xaa Xaa Thr Ser Asp Xaa Xaa
1               5                   10

<210> SEQ ID NO 193
<211> LENGTH: 11
<212> TYPE: PRT
<213> ORGANISM: Artificial Sequence
<220> FEATURE:

```
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2Me) = Biphenylalanine(2-Methyl)

<400> SEQUENCE: 193

His Xaa Gln Gly Xaa Xaa Thr Ser Asp Xaa Xaa
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(Pyr) = Biphenylalanine(Pyr)

<400> SEQUENCE: 194

His Xaa Gln Gly Xaa Xaa Thr Ser Asp Xaa Xaa
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (5)..(5)
```

```
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Bip(2F) = Biphenylalanine(2-Fluoro)

<400> SEQUENCE: 195

His Xaa Gln Gly Xaa Xaa Thr Ser Asp Xaa Xaa
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Synthetic peptidomimetic
<220> FEATURE:
<221> NAME/KEY: MISC_FEATURE
<222> LOCATION: (2)..(2)
<223> OTHER INFORMATION: Xaa is ACP = 1-aminocyclopropane carboxylic
      acid
<220> FEATURE:
<221> NAME/KEY: MISC_FEATURE
<222> LOCATION: (5)..(5)
<223> OTHER INFORMATION: Xaa is PCA = 4-Hydroxy-pyrrolidine-2-carboxylic
      acid
<220> FEATURE:
<221> NAME/KEY: MISC_FEATURE
<222> LOCATION: (6)..(6)
<223> OTHER INFORMATION: Xaa is 2F-Phe = 2-fluorophenylalanine
<220> FEATURE:
<221> NAME/KEY: MISC_FEATURE
<222> LOCATION: (10)..(10)
<223> OTHER INFORMATION: Xaa is Bip(OMe) = Biphenylalanine(OMe)
<220> FEATURE:
<221> NAME/KEY: MISC_FEATURE
<222> LOCATION: (11)..(11)
<223> OTHER INFORMATION: Xaa is Biphenylalanine(2-Trifluoromethyl)

<400> SEQUENCE: 196

His Xaa Gln Gly Xaa Xaa Thr Ser Asp Xaa Xaa
1               5                   10
```

ANTIDIABETIC COMPOUNDS

FIELD OF INVENTION

The present invention relates to novel compounds of general formula (I), their tautomeric forms, their pharmaceutically acceptable salts and pharmaceutical compositions containing them:

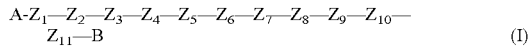

$$A-Z_1-Z_2-Z_3-Z_4-Z_5-Z_6-Z_7-Z_8-Z_9-Z_{10}-Z_{11}-B \qquad (I)$$

The present invention also relates to a processes for preparing compounds of general formula (I), their tautomeric forms, their pharmaceutically acceptable salts and pharmaceutical compositions containing them.

BACKGROUND TO THE INVENTION

Diabetes is characterized by impaired insulin secretion from pancreatic β-cells, insulin resistance or both (Cavaghan, M. K., et al., J. Clin. Invest. 2000, 106, 329). Majority of type 2 diabetic patients can be treated with agents that reduces hepatic glucose production (glucagon antagonist), reduce glucose absorption form GIT, stimulate β-cell function (insulin secretagogues) or with agents that enhance the tissue sensitivity of the patients towards insulin (insulin sensitizes). The drugs presently used to treat type 2 diabetes include α-glucosidase inhibitors, insulin sensitizers, insulin secretagogues and $K_{ATP}$ channel blocker (Chehade, J. M., et al., Drugs, 2000, 60, 95). However, almost one-half of type 2 diabetic subjects lose their response to these agents, over a period of time and thereby require insulin therapy. Insulin treatment has several drawbacks, it is injectable, produces hypoglycemia and causes weight gain (Burge, M. R., Diabetes Obes. Metab., 1999, 1, 199).

Problems with the current treatment necessiate new therapies to treat type 2 diabetes. In this regard, glucagon-like peptide-1 (GLP-1) agonist, which promote glucose-dependent insulin secretion in the pancreas and glucagon receptor antagonist, which inhibit hepatic glucose production by inhibiting glycogenolysis and gluconeogenesis, were found to be therapeutically potential. Thus GLP-1 agonist and glucagon antagonist together were found to reduce the circulating glucose levels and represent useful therapeutic agents for the treatment and prevention of type 2 diabetes (Perry, T. A., et al., Trends Pharmacol. Sci., 2003, 24, 377).

Glucagon and GLP-1 are members of structurally related peptide hormone family (secretin family). Glucagon and GLP-1 constitute a highly homologous set of peptides because these two hormones originate from a common precursor, preproglucagon, which upon tissue-specific processing leads to production of GLP-1 predominantly in the intestine and glucagon in the pancreas (Jiang, G., et al., Am. J. Physiol. Endocrinol. Metab., 2003, 284, E671-678). The receptors for these two peptides are homologous (58% identity) and belong to the class B family of G-protein coupled receptors (GPCRs). Class-B GPCRS is also called as the secretin receptor family, which consist of 15 peptide-binding receptors in humans. GPCR receptors comprise an extracellular N-teiininal domain of 100-160 residues, connected to a juxtamembrane domain (J-domain) of seven membrane-spanning α-helices with intervening loops and a. C-terminal tail (Brubaker, P. L., et al., Receptors Channels, 2002, 8, 179). Class B GPCRs are activated by endogenous peptide ligands of intermediate size, typically 30-40 amino acids (Hoare, S. R. J., Drug. Discovery Today, 2005, 10, 423; Gether, U., Endocrine Reviews, 2000, 21, 90).

Glucagon is a 29-amino acid peptide hormone processed from proglucagon in pancreatic α-cells by PC2. Glucagon acts via a seven transmembrane GPCRs, consisting of 485 amino acids. Glucagon is released into the bloodstream when circulating glucose is low. The main physiological role of glucagon is to stimulate hepatic glucose output, thereby leading to increase in glycemia (Tan, K., et al., Diabetologia, 1985, 28, 435). Glucagon provides the major counterregulatory mechanism for insulin in maintaining glucose homeostasis in vivo. Glucagon and its receptor represent potential targets for the treatment of diabetes. Antagonising glucagon action by blocking the action of the secreted glucagon at glucagon receptor (glucagon antagonist) or by inhibiting (suppressing) the glucagon production itself represents a new avenue for intervention of diabetes and metabolic disorders (Unson, C. G., et al., Peptides, 1989, 10, 1171; Parker, J. C., Diabetes, 2000, 49, 2079; Johnson, D. G., Science, 1982, 215, 1115).

The GLP-1 (7-36) amide is a product of the preproglucagon gene, which is secreted from intestinal L-cells, in response to the ingestion of food. The physiological action of GLP-1 has gained considerable interest. GLP-1 exerts multiple action by stimulating insulin secretion from pancreatic β-cells, in a glucose dependent manner (insulinotropic action). GLP-1 lowers circulating plasma glucagon concentration, by inhibiting its secretion (production) from α-cells (Drucker D. J., Endocrinology, 2001, 142, 521-527). GLP-1 also exhibits properties like stimulation of β-cell growth, appetite suppression, delayed gastric emptying and stimulation of insulin sensitivity (Nauck, M. A., Horm. Metab. Res., 2004, 36, 852). Currently, various analogs of GLP-1 and EX-4, such as Liraglutide/NN2211 (Novo Nordisk; Phase-III; WO 1998 008871), BIM 51077 (Ipsen; Phase-II; WO 2000 034331), CJC-1131 (ConjuChem; Phase-II; WO 2000 069911) and ZP-10 (Zealand & Aventis; Phase-II; WO 2001 004156) are in different stages of clinical development (Nauck M. A., Regulatory Peptides, 2004, 115, 13). Recently, BYETTA® (Exendin-4, AC 2933; U.S. Pat. No. 5,424,286), has been launched in the US market (Amylin & Lilly). However, all the existing GLP-1 agonists are delivered by the parenteral route of administration, so the patient incompliance is major problem with the existing GLP-1 based therapy.

The effector system of glucagon and GLP-1 receptors is the Adenylyl Cyclase (AC) enzyme. Interaction of glucagon or GLP-1 agonist with glucagon or GLP-1 receptors (GLP-1 R) respectively causes activation of AC, which converts ATP to cAMP. Increase in the intracellular cAMP level raises the ratio of ADP/ATP, thereby initiating the cell depolarization (due to closure of $K_{ATP}$ channel). Increase in the intracellular cAMP level also activates Protein Kinase (PK-A & PK-C), which raises the cystolic $Ca^{2+}$ concentration, by opening of L-type of $Ca^{2+}$ channel. An increase in the intracellular $Ca^{2+}$ leads to exocytosis of insulin, in pancreatic β-cells and glucagon peptide in α-cells (Fehmann, H. C., Endocr. Rev., 1995, 16, 390).

GLP-1 and glucagon sequences alignment shown below represent the primary structural relationships:

```
Glucagon:
                                    (Seq. ID No: 1)
NH2-¹HSQGTFTSD⁹YSKYLDSRRAQDFVQWLMNT-CONH2

GLP-1(7-36):
                                    (Seq. ID No: 2)
NH2-¹HAEGTFTSD⁹VSSYLEGQAAKEFIAWLVKGR-CONH2
```

First N-terminal 1-9 residues of GLP-1 peptide, with C-terminal amide:

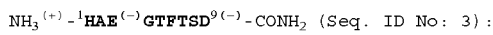

NH$_3^{(+)}$-$^1$HAE$^{(-)}$GTFTSD$^{9(-)}$-CONH$_2$ (Seq. ID No: 3):

Net charge Negative

First N-terminal 1-9 residues of Glucagon peptide, with C-terminal amide:

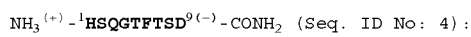

NH$_3^{(+)}$-$^1$HSQGTFTSD$^{9(-)}$-CONH$_2$ (Seq. ID No: 4):

Net charge Neutral

Single-letter abbreviations for amino acids can be found in Zubay, G., Biochemistry 2$^{nd}$ ed., 1988, MacMillan Publishing, New York, p. 33.

Native or synthetic GLP-1 peptides are rapidly metabolized by the proteolytic enzymes, such as dipeptidyl peptidase-IV (DPP-IV) into an inactive metabolite, thereby limiting the use of GLP-1 as a drug (Deacon, C. F., Regulatory Peptides, 2005, 128, 117). Similarly, several nonpeptidyl and peptidyl glucagon receptor antagonist of diverse structures have been reported over recent years, but none of them are in active development or under clinical trials (Kurukulasuriya, R., Expert Opinion Therapeutic Patents, 2005, 15, 1739; Lau, J., J. Med. Chem., 2007, 50, 113; Petersen, K. F. Diabetologia, 2001, 44, 2018; Cascieri, M. A., JBC, 1999, 274, 8694). It is believed that identifying nonpeptide ligands (especially agonist) for class B GPCRs is the principle bottleneck in drug discovery. HTS has apparently yielded few hits (US 2005/6927214; WO 2000/042026; US 2007/0043093), however, screening of those hits against corresponding receptors, especially under in vivo condition (animal models) prone to be false negatives (Murphy, K. G., PNAS, 2007, 104, 689).

Glucagon and GLP-1 both play major roles in overall glucose homeostasis (Drucker, D. J., J. Clin. Invest., 2007, 117, 24; Bollyky, J., J. Clin. Endocrinol. Metab., 2007, 92, 2879). Glucagon increases plasma glucose concentrations by stimulating gluconeogenesis and glycogenolysis in the liver while GLP-1 lowers plasma glucose concentrations mediated by glucose dependent insulin secretion (Mojsov, S., et al., JBC., 1990, 265, 8001). Knowing the importance of both glucagon peptide and GLP-1 in maintaining normal blood glucose concentrations, in the recent years, there has been considerable interest in identifying a single ligand, which act as glucagon receptor antagonists and GLP-1 receptor agonists (Claus, T. H., J. Endocrinology, 2007, 192, 371; Pan C. Q., JBC, 2006, 281, 12506).

Although identification of potent nonpeptide GLP-1 agonist may be difficult (Chen, D., PNAS, 2007, 104, 943; Knudsen, L. B., PNAS, 2007, 104, 937) but the design of a hybrid peptidomimetic acting as both glucagon antagonist and GLP-1 receptor agonist would likely to provide a novel approach for the treatment of type 2 diabetes (Claus, T B., J. Endocrinology, 2007, 192, 371). Structure-activity relationship (SAR) studies have been reported in the literature to determine the role of individual amino acids in both the glucagon and GLP-1 sequences (Runge, S., JBC, 2003, 278, 28005; Mann, R., Biochem. Soc. Trans., 2007, 35, 713). Glucagon and GLP-1 have no defined structure in aqueous solution, but in the presence of micelles or in the membrane mimetic environment, they adopt an alpha; helical structure in the mid-section, with flexible N- and C-terminal regions (Thornton, K., Biochemistry, 1994, 33, 3532; Neidigh, J. W., Biochemistry, 2001, 40, 13188). This suggests that the helical structure is required for binding of peptide ligands to their respective receptors. Mutations or deletion of amino acids in the N-terminal region of both the peptides results in receptor antagonists or inactive compounds, suggesting the importance of the N-terminus for receptor activation by both the glucagon and GLP-1 peptides (Hjorth, S. A., JBC., 1994, 269, 30121; Green, B. D., J. Mol. Endocrinology, 2003, 31, 529). In vivo, GLP-1 gets rapidly degraded by dipeptidyl-peptidase IV (DPP IV), a protease responsible for cleaving peptides containing proline or alanine residues in the penultimate. N-terminal position, resulting in the inactive metabolites. Substitution of the DPP-IV susceptible sites, such as substitution of Ala at 2$^{nd}$ position of GLP-1 peptide with D-Ala, Aib, greatly improves plasma stability (Deacon, C. F., Diabetes, 1998, 47, 764).

In the present investigation, we found that coupling of N-terminal sequence of glucagon peptide (first 1-9 residues, Seq. ID. No. 4) with a dipeptide of two unnatural amino acids resulted in the identification of novel class of peptidomimetics having both the glucagon antagonistic and GLP-1 agonistic activities, at varying degree of selectivity. To enhance the duration of action and stability against DPP-IV enzyme, we have site-specifically modified the hybrid peptidomimetics selectively at position $Z_2$ with unnatural amino acids such as D-Ala, Aib and 1-amino-cyclopropane carboxylic acid (ACP) and succeeded in identifying short peptidomimetics. Some of the peptidomimetics showed efficacy even by oral route of administration, while retaining both the glucagon antagonistic and GLP-1 agonistic activities.

PRIOR ART

A series of human GLP-1 mimics, have been reported with general formula Xaa1-Xaa11, wherein Xaa1-Xaa9 represent the first 1-9 residues of GLP-1 peptide (HAEGTFTSD; Seq. ID No. 3), with some analogs wherein Xaa2 represents either Ala Or are optionally replaced with Aib, Xaa3 represents amino acids with carboxylic acid side chain such as glutamic acid, aspartic acid etc. but not the Gln (Q), which is conserved in N-terminal sequence of Glucagon peptide (HSQGTFTSD, Seq. ID No. 4). Xaa6 represents Phe or are optionally replaced with -α-Me-2F-Phe-, Xaa9 represent amino acids with carboxylic acid or amide side chains such as aspartic acid, glutamic acid, asparagine etc., Xaa10 & Xaa11 represents combination of substituted or unsubstituted biphenyl alanine (Bip) derivatives (WO 2003/033671A2; US 2004/0127423 A1; WO 2004/094461 A2; US 2006/0004222 A1; WO 2006/014287 A1; WO 2006/127948 A2; WO 2007/082264 A2; US 2007/0021346 A1; US2007/0099835).

The present invention provides novel peptidomimetics of formula (I) (hereinafter referred to as peptidomimetics), which primarily act as a glucagon receptor antagonist and also exhibit GLP-1R agonistic effects. Different peptidomimetics reported in this invention showed significant glucose dependent insulin secretion (in vitro) and reduce circulating glucose levels (in vivo), with different level of affinity/selectivity towards glucagon and GLP-1 receptors. Furthermore, these peptidomimetics showed increased stability to proteolytic cleavage, especially against DPP-IV enzyme with improved half-life. Some of the peptidomimetics were found to be stable against GIT enzymes and acidic pH of stomach, with oral bioavailability, making them suitable candidate for the treatment/mitigation/prophylaxis of both type 1 & type 2 diabetes, metabolic disorders and related disorders.

Design Strategy for the Dual Acting Peptidomimetics (Glucagon Antagonist and GLP-1 Agonist):

The similarity between glucagon and GLP-1 peptides and also between their respective receptors raises the possibility of producing hybrid peptidomimetics that can bind with both the receptors, but selectively exhibit antagonistic activity at glucagon receptor and agonistic activity at GLP-1 receptor. Furthermore, in order to have oral bioavailibility and increased metabolic stability, it is also essential to develop peptidomimetics, with shorter amino acid sequence.

A general mechanism of peptide ligand interaction with class B GPCRs has emerged and is termed as the 'two-domain' model. The C-terminal portion of the peptide binds the N-domain of the receptor, confirm binding of ligand with the receptor and the N-terminal ligand region binds the J-domain, an interaction that activates the receptor and stimulates intracellular signaling, (FIG. 1) (Ji, T. H., JBC, 1988, 273, 17299; Hjorth, S. A., et al., Regulatory Peptides, 1996, 64, 70). Thus the N-domain of GLP-1 and glucagon receptors determine the selectivity of the C-terminal portion of GLP-1 and glucagon peptides respectively (Hoare, S. R. J., Drug. Discovery Today, 2005, 10, 423).

In order to design short chain peptides/peptidomimetics that binds with both receptors and exhibits agonist activity on the GLP-1 receptor but antagonist activity on the glucagon receptor, we decided to explore two-domain model concept (reported in the literature for Class-B, GPCRs), which indicates importance of both the activation and binding components of endogenous peptide ligands.

Recently, series of chimeric peptides (prepared recombinantly) has been reported, which act as both GLP-1 receptor agonist and glucagon receptor antagonist, constructed mainly by combining the N-terminal residues of glucagon peptide (residues 1-26) with last C-terminal 4 residues of GLP-1 peptide (VKGR) (Pan C. Q., et al., U.S. Pat. No. 6,864,069 B2; Pan C. Q., JBC, 2006, 281, 12506). However, these reports describe full-length chimeric peptides exhibiting GLP-1 receptor agonist and glucagon receptor antagonist properties and not the short chain peptides/peptidomimetics. In broad sense, this concept indicates that incorporation of C-terminal sequence of GLP-1 (especially last 4 residues, VKGR) into glucagon sequence lead to the formation of novel peptides, which act as both GLP-1 receptor agonist and glucagon receptor antagonist.

Thus for dual GLP-1 agonist activity and glucagon antagonistic activity, binding component of GLP-1 peptide sequence is essential (atleast last 4 residues) and for activation of GLP-1 receptor and inhibition of glucagon receptor, N-terminal sequence of glucagon peptide is required. However, while designing such dual acting peptidomimetics, it is also essential to keep shortest peptide sequence so that novel peptidomimetic could be orally bioavailable. Furthermore, to improve metabolic stability against DPP-IV enzyme, which selectively cleave N-terminal dipeptide at the penultimate N-terminal position, it is essential to incorporate DPP-IV stable amino acid, especially at $2^{nd}$ position.

In search of short length binding component, we explored the GLP-1 and glucagon receptor binding affinities of substituted or unsubstituted unnatural dipeptide amino acids (Bip-Bip). Such unnatural dipeptide amino acids have been reported, in combination of first 1-9 N-terminal residues of GLP-1 peptide sequence (WO 2003/033671A2; US 2004/0127423 A1; WO 2004/094461 A2; US 2006/0004222 A1; WO 2006/014287 A1; WO 2006/127948. A2; WO 2007/082264 A2; US 2007/0021346 A1; US2007/0099835) as potential peptidomimetics with GLP-1 agonist activity. Surprisingly, in our in vitro human GLP-1 and Glucagon receptors assays, dipeptides (Bip(OMe)-Bip(2Me)/Bip(OMe)-Bip(Pyr)/Bip(OMe)-Bip(2F)/Bip(OMe)-Bip(2CF$_3$)), [FIG. 2], showed antagonistic activity both in human GLP-1 and Glucagon receptors assay, [FIG. 3].

Knowing the binding affinity of dipeptide towards both the GLP-1 and glucagon receptors, we decided to couple this binding component with the activation unit. Surprisingly, instead of first 9 residues of N-terminal sequence of GLP-1 peptide (HAEGTFTSD; Seq. ID No. 3), when we attached this dipeptide to first 9 residues of N-terminal sequence of Glucagon peptide ($^1$HSQGTFTSD$^9$; Seq. ID No: 4), we found that this peptidomimetic (NH$_3^+$-HSQGTFTSD-Bip(OMe)-Bip(2Me)-CONH$_2$; Seq. ID No. 5) primarily showed glucagon receptor antagonistic activity, along with the GLP-1 receptor agonistic activity, [FIG. 4].

Furthermore, to increase the stability of this dual acting peptidomimetic against proteolytic cleavage, especially against DPP-IV (Dipeptidyl peptidase-IV) enzyme, we have site-specifically modified the hybrid peptidomimetic, selectively at position-2, with unnatural amino acids such as D-Ala, Aib or ACP and succeeded in identifying metabolically stable short peptidomimetics, while retaining both the GLP-1 agonist and glucagon antagonist activities.

Oral route of drug administration is universally accepted by patients due to its ease of administration but it encounters absorption and enzymatic barriers along with the first-pass effect. Although, the oral route of drug administration is the route of choice, the delivery of peptide and protein drugs by this route is currently limited due to their poor permeability and rapid degradetion in the gastrointestinal tract. Therefore, most of the commercially available peptide and protein drugs are administered by the parenteral route. However, due to patient non-compliance and short half-life of peptide and protein drugs, the parenteral route of administration is not suitable for the delivery of these drugs. Thus, the clinical utilities of most of peptide and protein drugs are currently limited due to their unfavorable physiochemical properties, such as high molecular weight, metabolic susceptibility and hydrophilicity (Morishita, M., Drug Discovery Today, 2006, 11, 905).

Epithelia represent a good target for the delivery of biopharmaceuticals. However, semi-permeable nature of epithelia limit the passage of peptide and protein drugs through their surfaces and thereby act as a principal absorption barrier (Arhewon, I. M., African J. Biotechnology, 2005, 4, 1591). The cell membrane of epithelial cells is made up of a continuous bilayer layer of membrane lipids and proteins. The membrane lipids consist of amphiphilic, phospholipids; such as phosphatidylcholine, sphingomyelin, phosphatidylserine and phosphatidylethanolamine, along with glycolipids and cholesterol molecules [FIG. 5].

Phosphatidylcholine and sphingomyelin are neutral phospholipids, whereas phosphatidylserine are negatively charged phospholipid. At physiological pH, most epithelia exhibit net negative charge due to the presence of phosphatidylserine. Thus while designing our peptidomimetics, attempts were made to avoid net negative charge. In general, in all the sequences designed in this invention, net neutral charge was maintained, which could be possible by incorporation first 1-9 residues of N-terminal sequence of glucagon peptide (Seq. ID No. 4) and not the first 1-9 residues of N-terminal sequence of GLP-1 peptide (Seq. ID No. 4), which mainly differ in their net charges (neutral to net negative) due to glutamine (Q; conserved in glucagon sequence) vs glutamic acid (E; conserved in GLP-1 sequence), at position-3. Overall, considerable potential exists in a single therapeutic compound, functioning as both a GLP-1R agonist and a glucagon receptor antagonist and preferably due to short peptide chain length, such peptidomimetic are likely to be orally bioavailable for the treatment or prevention of diabetes and related metabolic disorders.

SUMMARY OF THE INVENTION

The present invention describes a group of novel peptidomimetics that function both as an antagonist of the glucagon receptor and agonist of the GLP-1 receptor, having different degree of affinity/selectivity towards both the receptors and useful for reducing circulating glucose levels and for the treatment of diabetes. These peptidomimetics are defined by the general formula (I) as given below. The peptidomimetics of the present invention are useful in the treatment of the human or animal body, by regulation of insulin and glucagon action. The peptidomimetics of this invention are therefore suitable for the treatment/mitigation/regulation or prophylaxis of type 1 and type 2 diabetes and associated metabolic disorders.

PREFERRED EMBODIMENTS

A preferred embodiment of the present invention is to provide novel peptidomimetics of general formula (I), their tautomeric forms, novel intermediates involved in their synthesis, their pharmaceutically acceptable salts, their pharmaceutically acceptable solvates and pharmaceutical compositions containing them or their mixtures, suitable for the treatment treatment/mitigation/regulation of diabetes.

In another preferred embodiment is provided a process for the preparation of novel peptidomimetics of general formula (I), their tautomeric forms, their pharmaceutically acceptable salts, pharmaceutically acceptable solvates and pharmaceutical compositions containing them.

In a further preferred embodiment, is provided pharmaceutical compositions containing peptidomimetics of general formula (I), their tautomeric forms, their pharmaceutically acceptable salts, solvates and their mixtures having pharmaceutically acceptable carriers, solvents, diluents, excipients and other media normally employed in their manufacture.

In a still further preferred embodiment is provided the use of the novel peptidomimetics of the present invention as antidiabetic agents, by administering a therapeutically effective & non-toxic amount of the peptidomimetics of formula (I), or their pharmaceutically acceptable compositions to the mammals those are in need of such treatment.

ABBREVIATIONS USED

The following abbreviations are employed in the examples and elsewhere herein:
Aib=α-Aminoisobutyric acid,
ACN=Acetonitrile,
Bip=Biphenylalanine residue,
Bn=Benzyl,
Boc=tert-Butoxycarbonyl,
$Bu^t$=O-tert-butyl group,
cAMP=Adenosine 3',5'-cyclic monophosphate,
DCM=Dichloromethane,
DMF=N,N-Dimethylformamide,
DIPCDI=Di-isopropylcarbodiimide,
DIPEA=Diisopropylethylamine,
Et=Ethyl,
$Et_2O$=Diethyl ether,
Fmoc=Fluorenylmethoxycarbonyl,
g=Gram(s),
GLP-1R=Glucagon Like Peptide-1 Receptor,
Glucagon R=Glucagon receptor,
h=Hour(s),
HOBt=Hydroxybenzotriazole,
HOAt=7-Aza-hydroxybenzotriazole,
HBTU=2-(1H-benzotriazole-1-yl)-1,1,3,3-tetramethyl aminium hexafluorophosphate;
HPLC=High Performance Liquid Chromatography,
i.p.=intraperitonial,
L=Liter,
LC/MS=Liquid Chromatography/Mass Spectrometry,
Me=Methyl,
Min=minute (s),
mL=milliliter,
μl=microliter,
mg=milligram (s),
mmol=millimole (s),
MS=Mass Spectrometry,
PyBOP=Benzotriazole-1-yl-oxy-tris-pyrrolidino-phosphonium hexafluorophosphate,
SPPS=Solid Phase Peptide Synthesis,
sc=subcutaneous,
TMS=Trimethylsilyl,
TIPS=Triisopropylsilane,
TFA=Trifluoroacetic acid,
TBTU=2-(1H-benzotriazole-1-yl)-1,1,3,3-tetramethylaminium tetrafluoroborate,
Trt=Trityl group.

BRIEF DESCRIPTION OF THE DRAWINGS

FIG. 1 illustrates two-domain model for interaction of peptide ligands with class B GPCRs.

FIG. 2 illustrates structures of dipeptides which showed in vitro Glucagon/GLP-1 antagonistic activity.

FIG. 3 illustrates in vitro Human Glucagon and GLP-1 receptor antagonistic activity of dipeptide (Bip(OMe)-Bip (2Me)).

FIG. 4 illustrates in vitro Human Glucagon receptor antagonistic activity and GLP-1 receptor agonistic activity with Seq. ID. 5.

FIG. 5 illustrates some of the structural components of epithelial membrane.

FIG. 6 illustrates examples of orthogonally protected amino acids used in Fmoc based-solid phase peptide synthesis (SPPS) of peptidomimetics.

FIG. 7 illustrates in vitro DRC and $EC_{50}$ determination of Exendin (Figure A) and Seq. ID No. 32 (Figure B), in H GLP-1 R assay (agonistic activity, measured by amount of cAMP released).

FIG. 8 illustrates in vivo glucose reduction in C57 mice, with Seq. ID No. 32, after intraperitonial (i.p) administration (dose response curve (DRC))

FIG. 9 illustrates in vivo glucose reduction in C57 mice, with Seq. ID No. 32, after oral (p.o) administration (dose response curve (DRC))

FIG. 10 illustrates in vivo glucose reduction in db/db mice, with Seq. ID No. 32, after oral (p.o) administration.

FIG. 11 illustrates The serum insulin levels after single oral administration of vehicles/test peptidomimetics (Seq. ID. No. 30, 31 and 32), in C57BL/6J mice (in vivo).

DETAILED DESCRIPTION OF THE INVENTION

In accordance with the present invention, synthetic peptidomimetics having the structural formula (I), which showed glucose dependent insulin secretion. Furthermore, it was found that these peptidomimetics showed glucagon receptor antagonistic activity, along with the GLP-1 receptor agonistic activity. These dual acting peptidomimetics exhibit increased stability to proteolytic cleavage, especially against DPP-IV (Dipeptidyl peptidase-IV) enzyme. Most of peptidomimetics were found to be stable in rat plasma upto 24 hours (in vitro), showed increased stability against GIT enzymes such as pepsin and acidic stomach pH and also against liver microsomes (in vitro). Due to increased metabolic stability and also due to desirable net-charge profile, some of these peptidomimetics can also be delivered by oral routes of administration, for the treatment or prevention of diabetes and related metabolic disorders.

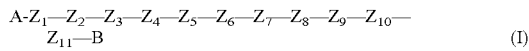
(I)

wherein, A represents the groups $—NH—R_1$, $R_3—CO—$ or $R_3—SO_2—$, wherein $R_1$ represents hydrogen, or optionally substituted linear or branched $(C_1-C_{10})$ alkyl chain; $R_3$ is selected from linear or branched $(C_1-C_{10})$ alkyl, $(C_3-C_6)$ cycloallyl, aryl, heteroaryl or arylalkyl groups.

In a preferred embodiment, the aryl group is selected from phenyl, napthyl, indanyl, fluorenyl or biphenyl, groups; the heteroaryl group is selected from pyridyl, thienyl, furyl, imidazolyl, benzofuranyl groups;

B represents $—COOR_2$, $—CONHR_2$ or $CH_2OR_2$ or a tetrazole, wherein $R_2$ represents H, optionally substituted groups selected from linear or branched $(C_1-C_{10})$ alkyl group, aryl or aralkyl groups as defined earlier;

$Z_1$ represents Histidine (H);

$Z_2$ represents a naturally or unnaturally occurring amino acid selected from the group comprising of L-Serine, D-Serine, L-alanine, D-alanine, α-amino-isobutyric acid (Aib), 1-amino cyclopropane carboxylic acid (ACP);

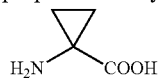

1-amino-cyclopropane carboxylic acid (ACP)

$Z_3$ represents glutamine (Gln; Q) or compounds of formula II.

Formula II

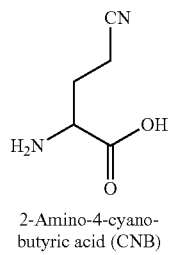

2-Amino-4-cyano-butyric acid (CNB)

$Z_4$ represents glycine (G) or the group 1-amino cyclopropane carboxylic acid (ACP);

$Z_5$ represents a naturally or normaturally occurring amino acid comprising a hydroxyl side chain; a preferred $Z_5$ is threonine or compounds of formula III Formula III

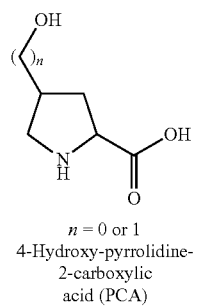

n = 0 or 1
4-Hydroxy-pyrrolidine-2-carboxylic acid (PCA)

$Z_6$ represents a naturally or unnaturally occurring amino acid having a disubstituted alpha carbon having two side chains, wherein each of them may independently be an optionally substituted alkyl or aryl or an aralkyl group wherein the substituents may be selected from one or more alkyl groups or one or more halo groups. Preferred $Z_6$ represents phenylalanine (Phe; F), alpha-methyl-phenylalanine (-α-Me-Phe-), alpha-methyl-2-fluorophenylalanine (-α-Me-2F-Phe-) or alpha-methyl-2,6-difluorophenylalanine (-α-Me-2,6-F-Phe-) or 2-fluorophenylalanine (-2F-Phe-) as given below.

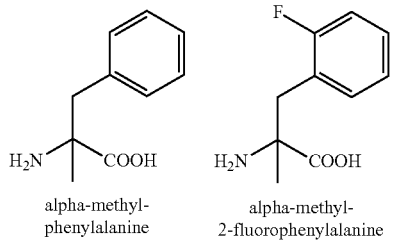

alpha-methyl-phenylalanine         alpha-methyl-2-fluorophenylalanine

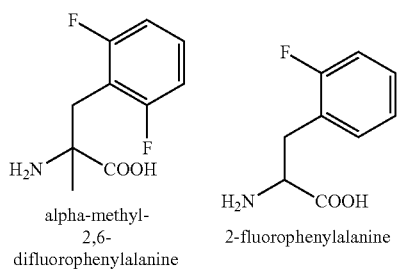

alpha-methyl-2,6-difluorophenylalanine         2-fluorophenylalanine $Z_7$ and $Z_8$ each independently represents a naturally or non-naturally occurring amino acid comprising a hydroxyl side chain, preferred $Z_7$ & $Z_8$ is independently selected from threonine, serine, 1-amino cyclopropane carboxylic acid (ACP) or compound of formula III as defined earlier;

$Z_9$ independently represent a naturally or normaturally occurring amino acid having an amino acid side chain comprising an acidic group. Preferred $Z_9$ is selected from aspartic acid or compounds of formula II as defined earlier.

$Z_{10}$ represents a naturally or unnaturally occurring amino acid of formula IV Formula IV

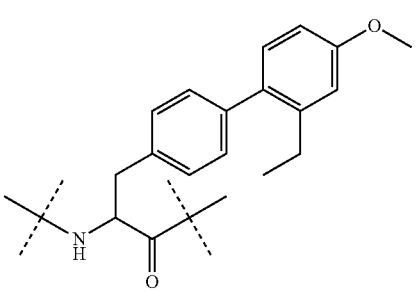

Bip(OMe)

$Z_{11}$ represents a naturally or unnaturally occurring amino acids of formula V (a-d)

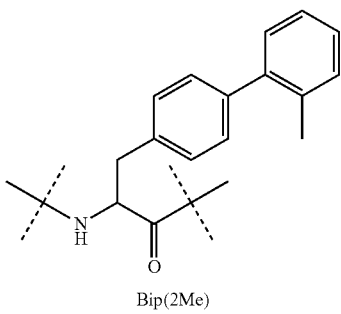

Bip(2Me)

Formula Va

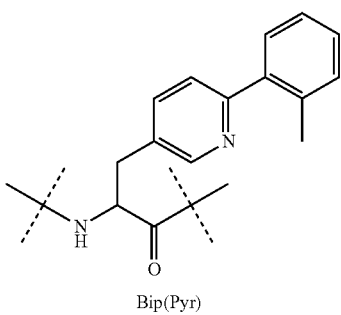

Bip(Pyr)

Formula Vb

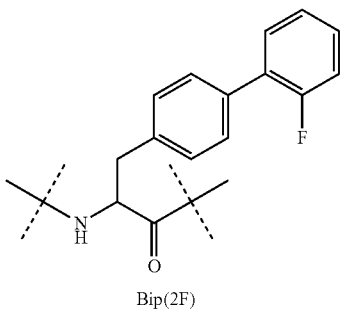

Bip(2F)

Formula Vc

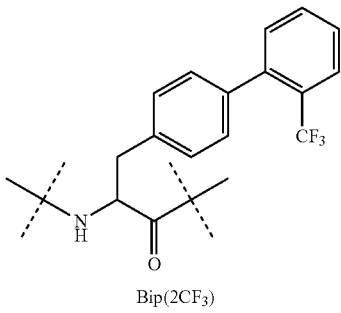

Bip(2CF3)

Formula Vd

DEFINITIONS

The term 'natural amino acids' indicates all those twenty amino acids, which are present in nature.

The term 'unnatural amino acids' or 'non-natural amino acids' represents either replacement of L-amino acids with corresponding D-amino acids such as replacement of L-Ala with D-Ala and the like or suitable modifications of the L or D amino acids, amino alkyl acids, either by α-alkylation such as substitution of Ala with α-methyl Ala (Aib) or replacement of Phe with α-methyl Phe;

substitution on the side chain of amino acid such as substitution of aromatic amino acid side chain with halogen, $(C_1-C_3)$alkyl, aryl groups, more specifically the replacement of Phe with 2 & 4-halo Phe;

The various groups, radicals and substituents used anywhere in the specification are described in the following paragraphs.

The term "alkyl" used herein, either alone or in combination with other radicals, denotes a linear or branched radical containing one to ten carbons, such as methyl, ethyl, n-propyl, iso-propyl, n-butyl, sec-butyl, tert-butyl, amyl, t-amyl, n-pentyl, n-hexyl, iso-hexyl, heptyl, octyl, decyl and the like.

The term "cycloalkyl" used herein, either alone or in combination with other radicals, denotes a radical containing three to seven carbons, such as cyclopropyl, cyclobutyl, cyclopentyl, cyclohexyl, cycloheptyl and the like.

The term "aryl" or "aromatic" used herein, either alone or in combination with other radicals, denotes an aromatic system containing one, two or three rings wherein such rings may be attached together in a pendant manner or may be fused, such as phenyl, naphthyl, tetrahydronaphthyl, indane, biphenyl, and the like.

The term "arylalkyl" denotes an alkyl group, as defined above, attached to an aryl, such as benzyl, phenylethyl, naphthylmethyl, and the like. The term "aryloxy" denotes an aryl radical, as defined above, attached to an alkoxy group, such as phenoxy, naphthyloxy and the like, which may be substituted.

The term "aralkoxy" denotes an arylalkyl moiety, as defined above, such as benzyloxy, phenethyloxy, naphthylmethyloxy, phenylpropyloxy, and the like, which may be substituted.

The term "heteroaryl" or "heteroaromatic" used herein, either alone or in combination with other radicals, denotes an aromatic system containing one, two or three rings wherein such rings may be attached together in a pendant manner or may be fused containing one or more hetero atoms selected from O, N or S, such as pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzopyranyl, benzopyranonyl, benzofuranyl, benzothienyl, indolinyl, indolyl, azaindolyl, azaindolinyl, benzodihydrofuranyl, benzodihydrothienyl, pyrazolopyrimidinyl, pyrazolopyrimidonyl, azaquinazolinyl, azaquinazolinoyl, pyridofuranyl, pyridothienyl, thienopyrimidyl, thienopyrimidonyl, quinolinyl, pyrimidinyl, pyrazolyl, quinazolinyl, quinazolonyl, pyrimidonyl, pyridazinyl, triazinyl, benzoxazinyl, benzoxazinonyl, benzothiazinyl, benzothiazinonyl, benzoxazolyl, benzothiazolyl, benzimidazolyl, benzotriazolyl, phthalazynil, naphthylidinyl, purinyl, carbazolyl, phenothiazinyl, phenoxazinyl, and the like.

The term "heteroaralkyl" used herein, either alone or in combination with other radicals, denotes a heteroaryl group, as defined above, attached to a straight or branched saturated carbon chain containing 1 to 6 carbons, such as (2-furyl)methyl, (3-furyl)methyl, (2-thienyl)methyl, (3-thienyl)methyl, (2-pyridyl)methyl, 1-methyl-1-(2-pyrimidyl)ethyl and the like. The terms "heteroaryloxy", "heteroaralkoxy", "heterocycloxy" denotes heteroaryl, heteroarylalkyl, groups respectively, as defined above, attached to an oxygen atom.

The term "acyl" used herein, either alone or in combination with other radicals, denotes a radical containing one to eight carbons such as formyl, acetyl, propanoyl, butanoyl, isobutanoyl, pentanoyl, hexanoyl, heptanoyl, benzoyl and the like, which may be substituted.

The term "carboxylic acid" used herein, alone or in combination with other radicals, denotes a —COOH group, and includes derivatives of carboxylic acid such as esters and amides. The term "ester" used herein, alone or in combination with other radicals, denotes —COO— group, and includes carboxylic acid derivatives, where the ester moieties are alkoxycarbonyl, such as methoxycarbonyl, ethoxycarbonyl, and the like, which may be substituted.

Unless otherwise indicated, the term 'amino acid' as employed herein alone or as part of another group includes, without limitation, an amino group and a carboxyl group linked to the same carbon, referred to as 'α' carbon.

The absolute 'S' configuration at the 'α' carbon is commonly referred to as the 'L' or natural configuration. The 'R' configuration at the 'α' carbon is commonly referred to as the 'D' amino acid. In the case where both the 'α-substituents' is equal, such as hydrogen or methyl, the amino acids are Gly or Aib and are not chiral.

The term 'receptor antagonist' refers to compounds that inhibit the activation of receptor and generation of secondary messenger such as cyclic AMP either by competitive or non-competitive binding.

The term 'Glucagon receptor antagonist' refers to compounds that inhibit activation of glucagon receptor.

The term 'GLP-1 receptor modulator or agonist' refers to a compound that acts at the GLP-1 receptor to alter its ability to regulate downstream signaling events, such as cAMP production and insulin release. Example of receptor modulators includes agonist, partial agonist, inverse agonist and allosteric potentiators.

In accordance with the present invention, the synthetic isolated peptidomimetics described herein primarily act as a glucagon receptor antagonist. Furthermore, it was found that these peptidomimetics also act as GLP-1 receptor agonists. These synthetic peptidomimetics exhibit desirable in vitro glucagon receptor antagonist properties as well as GLP-1 receptor agonist activity in CHO cells transfected with human glucagon or GLP-1 receptor (H Glucagon R or HGLP-1R), in the range of 1-100 nM concentration. H GLP-1 R agonistic activity, is assessed by estimation of amount of cAMP released, while glucagon antagonistic activity was assessed by measuring the amount of cAMP production inhibited by the test peptidomimetics, in presence of glucagon peptide. Novel peptidomimetics exhibit desirable in vitro glucagon receptor antagonist activity in CHO cells transfected with human glucagon receptor, in the range of 1-100-nM concentration. Some of the test peptidomimetics prepared showed glucose dependent insulin release and reduces fasting hyperglycemia, without causing hypoglycemia, when tested in vivo, in different diabetic animal models, such as hyperglycemic C57 mice and db/db mice, thus making them ideal therapeutic candidates for the treatment and prevention of type 2 diabetes. These new classes of peptidomimetics can be administered by oral or parenteral routes of administration.

The present invention provides peptidomimetics of formula (I) pharmaceutical compositions employing such peptidomimetics either alone or in combination and for methods of using such peptidomimetics. In particular, the present invention provides a pharmaceutical composition comprising a therapeutically effective amount of a peptidomimetics of formula (I), alone or in combination(s), with a pharmaceutically acceptable carrier.

Further provided is a method for treating or delaying the progression or onset of diabetes, especially type 2 diabetes, including complications of diabetes, including retinopathy, neuropathy, nephropathy and delayed wound healing and related diseases such as insulin resistance (impaired glucose homeostasis), hyperglycemia, hyperinsulinemia, elevated blood levels of fatty acids or glycerol, hyperlipidemia including hypertriglyceridemia, syndrome X, atherosclerosis and hypertension, wherein a therapeutically effective amount of a peptidomimetics of formula (I) or their combination(s) are administered to a mammal, example, human, a patient in need of treatment.

Preparation of the Peptidomimetics:

Several synthetic routes can be employed to prepare the peptidomimetics of the present invention well known to one skilled in the art of peptide synthesis. The peptidomimetics of formula (I), where all symbols are as defined earlier can be synthesized using the methods described below, together with conventional techniques known to those skilled in the art of peptide synthesis, or variations thereon as appreciated by those skilled in the art. Referred methods include, but not limited to those described below.

The peptidomimetics thereof described herein may be produced by chemical synthesis using suitable variations of various solid-phase techniques generally known such as those described in G. Barany & R. B. Merrifield, "The peptides: Analysis, synthesis, Biology"; Volume 2-"Special methods in peptide synthesis, Part A", pp. 3-284, E. Gross & J. Meienhofer, Eds., Academic Press, New York, 1980; and in J. M. Stewart and J. D. Young, "Solid-phase peptide synthesis" 2nd Ed., Pierce chemical Co., Rockford, Il, 1984.

The preferred strategy for preparing the peptidomimetics of this invention is based on the use of Fmoc-based SPPS approach, wherein Fmoc (9-Fluorenyl-methyl-methyloxycarbonyl) group is used for temporary protection of the α-amino group, in combination with the acid labile protecting groups, such as t-butyloxy carbonyl (Boc), tert-butyl ($Bu^t$), Trityl (Trt) groups (FIG. 6), for temporary protection of the amino acid side chains (see for example E. Atherton & R. C. Sheppard, "The Fluorenylmethoxycarbonyl amino protecting group", in "The peptides: Analysis, synthesis, Biology"; Volume 9—"Special methods in peptide synthesis, Part C", pp. 1-38, S. Undenfriend & J. Meienhofer, Eds., Academic Press, San Diego, 1987).

The peptidomimetics can be synthesized in a stepwise manner on an insoluble polymer support (resin), starting form the C-terminus of the peptide. In an embodiment, the synthesis is initiated by appending the C-terminal amino acid of the peptide to the resin through formation of an amide, ester or ether linkage. This allows the eventual release of the resulting peptide as a C-terminal amide, carboxylic acid or alcohol, respectively.

In the Fmoc-based SPPS, the C-terminal amino acid and all other amino acids used in the synthesis are required to have their α-amino groups and side chain functionalities (if present) differentially protected (orthogonal protection), such that the α-amino protecting group may be selectively removed during the synthesis, using suitable base such as 20% piperidine solution, without any premature cleavage of peptide from resin or deprotection of side chain protecting groups, usually protected with the acid labile protecting groups.

The coupling of an amino acid is performed by activation of its carboxyl group as an active ester and reaction thereof with unblocked α-amino group of the N-terminal amino acid appended to the resin. After every coupling and deprotection, peptidyl-resin was washed with the excess of solvents, such as DMF, DCM and diethyl ether. The sequence of α-amino group deprotection and coupling is repeated until the desired peptide sequence is assembled (Scheme 1). The peptide is then cleaved from the resin with concomitant deprotection of the side chain functionalities, using an appropriate cleavage mixture, usually in the presence of appropriate scavengers to limit side reactions. The resulting peptide is finally purified by reverse phase HPLC.

The synthesis of the peptidyl-resins required as precursors to the final peptides utilizes commercially available cross-linked polystyrene polymer resins (Novabiochem, San Diego, Calif.). Preferred for use in this invention are Fmoc-PAL-PEG-PS resin, 4-(2', 4'-dimethoxyphenyl-Fmoc-aminomethyl)-phenoxyacetyl-p-methyl benzhydrylamine resin (Fmoc-Rink amide MBHA resin), 2-chloro-Trityl-chloride resin or p-benzyloxybenzyl alcohol resin (HMP resin) to which the C-terminal amino acid may or may not be already attached. If the C-terminal amino acid is not attached, its attachment may be achieved by HOBt active ester of the Fmoc-protected amino acid formed by its reaction with DIPCDI. In case of 2-Chloro-trityl resin, coupling of first Fmoc-protected amino acid was achieved, using DIPEA. For the assembly of next amino acid, N-terminal protection of peptidyl resin was selectively deprotected using a solution of 10-20% piperidine solution. After every coupling and deprotection, excess of amino acids and coupling reagents were removed by washing with DMF, DCM and ether. Coupling of the subsequent amino acids can be accomplished using HOBt or HOAT active esters produced from DIPCDI/HOBt or DIPCDI/HOAT, respectively. In case of some difficult coupling, especially coupling of those amino acids, which are hydrophobic or amino acids with bulky side chain protection, complete coupling can be achieved using a combination of highly efficient coupling agents such as HBTU, PyBOP or TBTU, with additives such as DIPEA.

The synthesis of the peptidomimetics described herein can be carried out by using batchwise or continuous flow peptide synthesis apparatus, such as CS-Bio or AAPPTEC peptide synthesizer, utilizing the Fmoc/t-butyl protection strategy. The non-natural non-commercial amino acids present at different position were incorporated into the peptide chain, using one or more methods known in the art. In one approach, a Fmoc-protected non-natural amino acid was prepared in solution, using appropriate literature procedures. For example, the Fmoc-protected Bip analogs, described above, were prepared using modified Suzuki cross coupling method, as known in literature (Kotha, S., et al., Tetrahedron 2002, 58, 9633). The Fmoc-protected α-methylated amino acids were prepared using asymmetric Strecker synthesis (Boesten, W. H. J., et al., Org. Lett., 2001, 3(8), 1121). The resulting derivative was then used in the step-wise synthesis of the peptide. Alternatively, the required non-natural amino acid was built on the resin directly using synthetic organic chemistry procedures and a linear peptide chain were build.

Scheme 1: General Scheme for Fmoc-Based SPPS

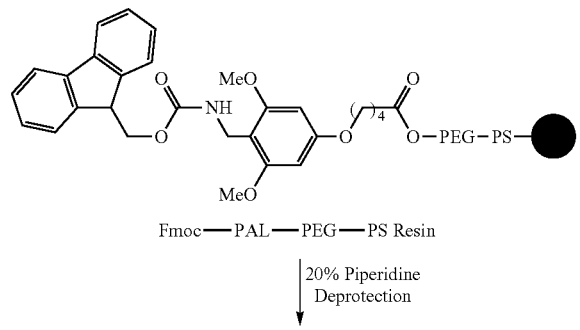

Fmoc—PAL—PEG—PS Resin

20% Piperidine
Deprotection

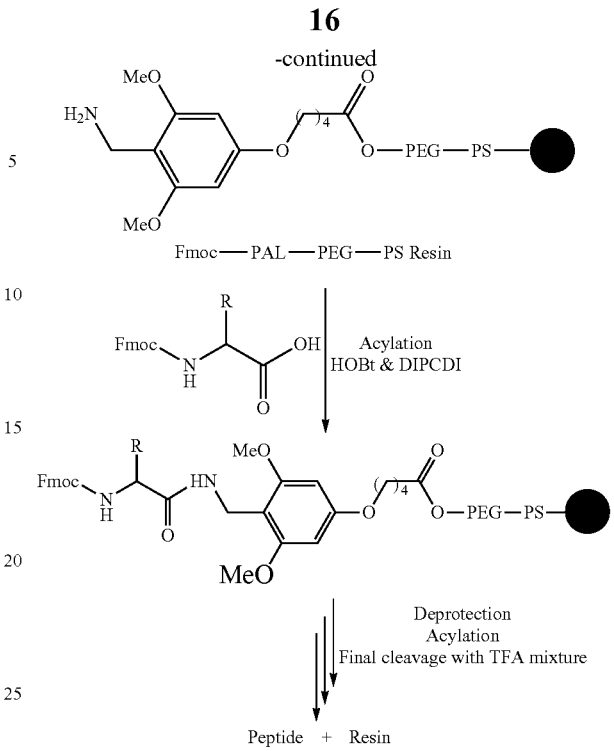

The peptide-resin precursors for their respective peptidomimetics may be cleaved and deprotected using suitable variations of any of the standard cleavage procedures described in the literature (King, D. S., et al., Int. J. Peptide Protein Res., 1990, 36, 255). A preferred method for use in this invention is the use of TFA cleavage mixture, in the presence of water and TIPS as scavengers. Typically, the peptidyl-resin was incubated in TFA/Water/TIPS (94:3:3; V:V:V; 10 ml/100 mg of peptidyl resin) for 1.5-2 hrs at room temperature. The cleaved resin is then filtered off, the TFA solution is concentrated or dried under reduced pressure. The resulting crude peptide is either precipitated or washed with $Et_2O$ or is re-dissolved directly into DMF or 50% aqueous acetic acid for purification by preparative HPLC.

Peptidomimetics with the desired purity can be obtained by purification using preparative HPLC. The solution of crude peptide is injected into a semi-Prep column (Luna 10μ; $C_{18}$; 100 Å), dimension 250×50 mm and eluted with a linear gradient of ACN in water, both buffered with 0.1% TFA, using a flow rate of 15-50 ml/min with effluent monitoring by PDA detector at 220 nm. The structures of the purified peptidomimetics can be confirmed by Electrospray Mass Spectroscopy (ES-MS) analysis.

All the peptide prepared were isolated as trifluoro-acetate salt, with TFA as a counter ion, after the Prep-HPLC purification. However, some peptides were subjected for desalting, by passing through a suitable ion exchange resin bed, preferably through anion-exchange resin Dowex SBR P(Cl) or an equivalent basic anion-exchange resin. In some cases, TFA counter ions were replaced with acetate ions, by passing through suitable ion-exchange resin, eluted with dilute acetic acid solution. For the preparation of the hydrochloride salt of peptides, in the last stage of the manufacturing, selected peptides, with the acetate salt was treated with 4 M HCl. The resulting solution was filtered through a membrane filter (0.2 μm) and subsequently lyophilized to yield the white to off-white HCl salt. Following similar techniques and/or such suitable modifications, which are well within the scope of persons skilled in the art, other suitable pharmaceutically acceptable salts of the peptidomimetics of the present invention were prepared.

General Method of Preparation of Peptidomimetics, Using SPPS Approach:

Assembly of Peptidomimetics on Resin:

Sufficient quantity (50-100 mg) of Fmoc-PAL-PEG-PS resin or Fmoc-Rink amide MBHA resin, loading: 0.5-0.6 mmol/g was swelled in DMF (1-10 ml/100 mg of resin) for 2-10 minutes. The Fmoc-group on resin was then removed by incubation of resin with 10-30% piperidine in DMF (10-30 ml/100 mg of resin), for 10-30 minutes. Deprotected resin was filtered and washed excess of DMF, DCM and ether (50 ml×4). Washed resin was incubated in freshly distilled DMF (1 ml/100 mg of resin), under nitrogen atmosphere for 5 minutes. A 0.5 M solution of first Fmoc-protected amino acid (1-3 eq.), pre-activated with HOBt (1-3 eq.) and DIPCDI (1-2 eq.) in DMF was added to the resin, and the resin was then shaken for 1-3 hrs, under nitrogen atmosphere. Coupling completion was monitored using a qualitative ninhydrin test. After the coupling of first amino acid, the resin was washed with DMF, DCM and Diethyl ether (50 ml×4). For the coupling of next amino acid, firstly, the Fmoc-protection on first amino acid, coupled with resin was deprotected, using a 10-20% piperidine solution, followed by the coupling the Fmoc-protected second amino acid, using a suitable coupling agents, and as described above. The repeated cycles of deprotection, washing, coupling and washing were performed until the desired peptide chain was assembled on resin, as per general Scheme 1 above.

Finally, the Fmoc-protected peptidyl-resin prepared above was deprotected by 20% piperidine treatment as described above and the peptidyl-resins were washed with DMF, DCM and Diethyl ether (50 ml×4). Resin containing desired peptide was dried under nitrogen pressure for 10-15 minutes and subjected for cleavage/deprotection.

Representative Example of Automated Solid Phase Synthesis of Peptide Sequence ID. No. 32 (H$_2$N-H-Aib-QGT-(α-Me-2F-Phe)-TSD-Bip(OMe)-Bip(2CF$_3$)-CONH$_2$).

The linear peptide chain, H$_2$N-H-Aib-QGT-(α-Me-2F-Phe)-TSD-Bip(OMe)-Bip(2CF$_3$)-PAL-PEG-PS was assembled on an automated CS-Bio 536 PepSynthesiser™ using Fmoc solid phase peptide synthesis (SPPS) approach (Scheme 2). The Fmoc amino acids and the 2-(1H-Benzotriazol-1-yl)-1,1,3,3-tetramethyluroniumtetrafluoroborate (TBTU) were packed together in vials and positioned in the amino acid module of the synthesizer. A stock solution of diisopropylethylamine (DIPEA; 0.9 M) and DMF were stored in reagent bottles, under dry nitrogen atmosphere. The resin, Fmoc-PAL-PEG-PS (0.38 mmol/g; 1 g) was dried over P$_2$O$_5$, in vacuo (1 hr) and swollen in freshly distilled DMF (5 mL). The swollen resin was slurry packed into a glass column and positioned in the synthesizer. All the synthetic cycles were carried out at a flow rate of 5 mL min$^{-1}$, Table 1. The resin was washed with freshly distilled DMF for 10 minutes. Deprotection of Fmoc group was performed with 20% piperidine in DMF for 10 minutes and the deprotection was monitored by UV detection of the column effluent at 304 nm.

Scheme 2: SPPS of Seq. ID. No. 32

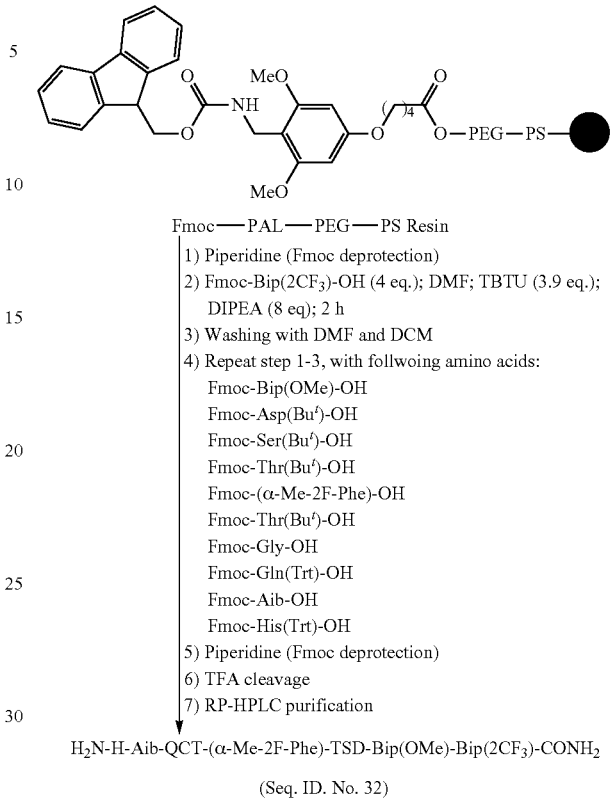

Fmoc—PAL—PEG—PS Resin

1) Piperidine (Fmoc deprotection)
2) Fmoc-Bip(2CF$_3$)-OH (4 eq.); DMF; TBTU (3.9 eq.); DIPEA (8 eq); 2 h
3) Washing with DMF and DCM
4) Repeat step 1-3, with follwoing amino acids:
   Fmoc-Bip(OMe)-OH
   Fmoc-Asp(Bu$^t$)-OH
   Fmoc-Ser(Bu$^t$)-OH
   Fmoc-Thr(Bu$^t$)-OH
   Fmoc-(α-Me-2F-Phe)-OH
   Fmoc-Thr(Bu$^t$)-OH
   Fmoc-Gly-OH
   Fmoc-Gln(Trt)-OH
   Fmoc-Aib-OH
   Fmoc-His(Trt)-OH
5) Piperidine (Fmoc deprotection)
6) TFA cleavage
7) RP-HPLC purification H$_2$N-H-Aib-QCT-(α-Me-2F-Phe)-TSD-Bip(OMe)-Bip(2CF$_3$)-CONH$_2$ (Seq. ID. No. 32)

Excess piperidine was removed by three auxiliary wash cycles and a distilled DMF wash cycle, with each cycle of 15 minutes. The amino group was treated with Fmoc-amino acid (4 equivalent), preactivated with TBTU (3.9 equivalent) in the presence of DIPEA (8 equivalent) and recycled for 120 minutes. The excess amino acid and soluble by-products were removed from column and loop by four auxiliary wash cycles and distilled DMF wash cycles, with each cycle of 10 minutes. Furthermore, synthetic cycles (deprotection, wash, acylation and wash) were repeated for complete assembly of linear peptide. Final deprotection cycle was performed with 20% piperidine in DMF for 15 minutes to remove the terminal Fmoc group, followed by wash cycle (10×4 minutes). Completed peptide-resin was filtered through sintered glass filter, washed three times successively with DMF, DCM, methanol, DMF and diethyl ether (100 mL each). Peptide-resin was dried in vacuo over P$_2$O$_5$ (2 hr) and stored at −20° C. Ninhydrin resin test was carried out to check the N-terminal free amino group of resin bound peptide. Appearance of blue-purple colouration of the solution and the resin beads indicates the presence of free amino group on resin bound peptide and was considered to be a positive test.

TABLE 1

Automated cycles for solid phase peptide synthesis

| Step | Function | Reagent/Solvent | Number of cycles | Time (Minute) |
|---|---|---|---|---|
| 1 | Wash | Dimethylformamide (DMF) | 1 | 10 |
| 2 | Deprotection | 20% piperidine in DMF | 2 | 15 |
| 3 | Wash | DMF | 3 | 15 |

TABLE 1-continued

Automated cycles for solid phase peptide synthesis

| Step | Function | Reagent/Solvent | Number of cycles | Time (Minute) |
|---|---|---|---|---|
| 4 | Acylation | Amino acid; TBTU and diisopropylethylamine (in DMF) | Recycle | 120 |
| 5 | Wash | Dimethylformamide | 4 | 10 |

Small-scale cleavage was carried out to assess the purity of resin bound peptide. The dried Peptide-resin (ca 10-mg) was treated with mixture (1-mL) of TFA, water, triisopropylsilane (95:2.5:2.5 v/v), for 90 minutes at room temperature with gentle occasional swirling. The resin was filtered, washed thoroughly with neat TFA (1 mL) and the entire filtrate was evaporated under reduced pressure. Residual TFA was azeotroped three times with diethyl ether (2 mL). Residue obtained was suspended in distilled water (2 mL) and the aqueous layer was extracted three times with diethyl ether (3 mL). The aqueous layer was separated and freeze-dried to yield the crude peptide $H_2N$-H-Aib-QGT-($\alpha$-Me-2F-Phe)-TSD-Bip(OMe)-Bip($2CF_3$)-$CONH_2$. The lyophilised peptide $H_2N$-H-Aib-QGT-($\alpha$-Me-2F-Phe)-TSD-Bip(OMe)-Bip($2CF_3$)-$CONH_2$ was dissolved in 0.1% aqueous TFA (ca 1 mg/1 mL) and its purity was analyzed by analytical RP-HPLC and characterized by electrospray ionisation mass spectrometry (ESI-MS). Percent purity: 90% (crude peptide). ESI-MS; Calcd. for $H_2N$-H-Aib-QGT-($\alpha$-Me-2F-Phe)-TSD-Bip(OMe)-Bip($2CF_3$)-$CONH_2$: 1580 ($M^+$), 1602 ($M+Na^+$) and 1618 ($M+K^+$); Found (m/z): 1580 ($M^+$), 1602 ($M+Na^+$) and 1618 ($M+K^+$).

Using above protocol and suitable variations thereof which are within, the scope of a person skilled in the art, the peptidomimetics designed in the present invention were prepared, using Fmoc-SPPS approach. Furthermore, resin bound peptidomimetics were cleaved and deprotected, purified and characterized using following protocol.

Cleavage and Deprotection:

The desired peptidomimetics were cleaved and deprotected from their respective peptidyl-resins by treatment with TFA cleavage mixture as follows. A solution of TFA/Water/Triisopropylsilane (95:2.5:2.5) (10 ml/100 mg of peptidyl-resin) was added to peptidyl-resins and the mixture was kept at room temperature with occasional starring. The resin was filtered, washed with a cleavage mixture and the combined filtrate was evaporated to dryness. Residue obtained was dissolved in 10 ml of water and the aqueous layer was extracted 3 times with ether (20 ml each) and finally the aqueous layer was freeze-dried. Crude peptide obtained after freeze-drying was purified by preparative HPLC as follows:

Preparative HPLC Purification of the Crude Peptidomimetics:

Preparative HPLC was carried out on a Shimadzu LC-8A liquid chromatograph. A solution of crude peptide dissolved in DMF or water was injected into a semi-Prep column (Luna 10μ; $C_{18}$; 100 A°), dimension 250×50 mm and eluted with a linear gradient of ACN in water, both buffered with 0.1% TFA, using a flow rate of 15-50 ml/min, with effluent monitoring by PDA detector at 220 nm. A typical gradient of 20% to 70% of water-ACN mixture, buffered with 0.1% TFA was used, over a period of 50 minutes, with 1% gradient change per minute. The desired product eluted were collected in a single 10-20 ml fraction and pure peptidomimetics were obtained as amorphous white powders by lyophilisation of respective HPLC fractions.

HPLC Analysis of the Purified Peptidomimetics

After purification by preparative HPLC as described above, each peptide was analyzed by analytical RP-HPLC on a Shimadzu LC-10AD analytical HPLC system. For analytic HPLC analysis of peptidomimetics, Luna 5μ; $C_{18}$; 100 Å°, dimension 250 X 4.6 mm column was used, with a linear gradient of 0.1%. TFA and ACN buffer and the acquisition of chromatogram was carried out at 220 nm, using a PDA detector.

Characterization by Mass Spectrometry

Each peptide was characterized by electrospray ionisation mass spectrometry (ESI-MS), either in flow injection or LC/MS mode. Triple quadrupole mass spectrometers (API-3000 (MDS-SCIES, Canada) was used in all analyses in positive and negative ion electrospray mode. Full scan data was acquired over the mass range of quadrupole, operated at unit resolution. In all cases, the experimentally measured molecular weight was within 0.5 Daltons of the calculated monoisotopic molecular weight. Quantification of the mass chromatogram was done using Analyst 1.4.1 software.

Utilizing the synthetic methods described herein along with other commonly known techniques and suitable variations thereof, the following novel peptidomimetics were prepared. This list is indicative of the various groups of peptidomimetics, which can be prepared according to the present invention, and are expected to at least include obvious variations of these peptidomimetics. However, such disclosure should not be construed as limiting the scope of the invention in any way. In Table 2-(i-vi), novel peptidomimetics of present invention are listed along with their corresponding Seq. ID. No.

TABLE 2

List of peptidomimetics prepared

| Seq. ID. No. | Sequence of peptidomimetics |
|---|---|
| (i): | |
| 5 | HSQGTFTSD-Bip(OMe)-Bip(2Me) |
| 6 | HSQGTFTSD-Bip(OMe)-Bip(Pyr) |
| 7 | HSQGTFTSD-Bip(OMe)-Bip(2F) |
| 8 | HSQGTFTSD-Bip(OMe)-Bip($2CF_3$) |
| 9 | HAQGTFTSD-Bip(OMe)-Bip(2Me) |
| 10 | HAQGTFTSD-Bip(OMe)-Bip(Pyr) |

TABLE 2-continued

List of peptidomimetics prepared

| Seq. ID. No. | Sequence of peptidomimetics |
|---|---|
| 11 | HAQGTFTSD-Bip(OMe)-Bip(2F) |
| 12 | HAQGTFTSD-Bip(OMe)-Bip(2CF$_3$) |
| 13 | H-Aib-QGTFTSD-Bip(OMe)-Bip(2Me) |
| 14 | H-Aib-QGTFTSD-Bip(OMe)-Bip(Pyr) |
| 15 | H-Aib-QGTFTSD-Bip(OMe)-Bip(2F) |
| 16 | H-Aib-QGTFTSD-Bip(OMe)-Bip(2CF$_3$) |
| 17 | H-(ACP)-QGTFTSD-Bip(OMe)-Bip(2Me) |
| 18 | H-(ACP)-QGTFTSD-Bip(OMe)-Bip(Pyr) |
| 19 | H-(ACP)-QGTFTSD-Bip(OMe)-Bip(2F) |
| 20 | H-(ACP)-QGTFTSD-Bip(OMe)-Bip(2CF$_3$) |
| (ii) | |
| 21 | HSQGT-(α-Me-2F-Phe)-TSD-Bip(OMe)-Bip(2Me) |
| 22 | HSQGT-(α-Me-2F-Phe)-TSD-Bip(OMe)-Bip(Pyr) |
| 23 | HSQGT-(α-Me-2F-Phe)-TSD-Bip(OMe)-Bip(2F) |
| 24 | HSQGT-(α-Me-2F-Phe)-TSD-Bip(OMe)-Bip(2CF$_3$) |
| 25 | HAQGT-(α-Me-2F-Phe)-TSD-Bip(OMe)-Bip(2Me) |
| 26 | HAQGT-(α-Me-2F-Phe)-TSD-Bip(OMe)-Bip(Pyr) |
| 27 | HAQGT-(α-Me-2F-Phe)-TSD-Bip(OMe)-Bip(2F) |
| 28 | HAQGT-(α-Me-2F-Phe)-TSD-Bip(OMe)-Bip(2CF$_3$) |
| 29 | H-Aib-QGT-(α-Me-2F-Phe)-TSD-Bip(OMe)-Bip(2Me) |
| 30 | H-Aib-QGT-(α-Me-2F-Phe)-TSD-Bip(OMe)-Bip(Pyr) |
| 31 | H-Aib-QGT-(α-Me-2F-Phe)-TSD-Bip(OMe)-Bip(2F) |
| 32 | H-Aib-QGT-(α-Me-2F-Phe)-TSD-Bip(OMe)-Bip(2CF$_3$) |
| 33 | H-(ACP)-QGT-(α-Me-2F-Phe)-TSD-Bip(OMe)-Bip(2Me) |
| 34 | H-(ACP)-QGT-(α-Me-2F-Phe)-TSD-Bip(OMe)-Bip(Pyr) |
| 35 | H-(ACP)-QGT-(α-Me-2F-Phe)-TSD-Bip(OMe)-Bip(2F) |
| 36 | H-(ACP)-QGT-(α-Me-2F-Phe)-TSD-Bip(OMe)-Bip(2CF$_3$) |
| (iii): | |
| 37 | HSQGT-(2F-Phe)-TSD-Bip(OMe)-Bip(2Me) |
| 38 | HSQGT-(2F-Phe)-TSD-Bip(OMe)-Bip(Pyr) |
| 39 | HSQGT-(2F-Phe)-TSD-Bip(OMe)-Bip(2F) |
| 40 | HSQGT-(2F-Phe)-TSD-Bip(OMe)-Bip(2CF$_3$) |
| 41 | HAQGT-(2F-Phe)-TSD-Bip(OMe)-Bip(2Me) |
| 42 | HAQGT-(2F-Phe)-TSD-Bip(OMe)-Bip(PYr) |
| 43 | HAQGT-(2F-Phe)-TSD-Bip(OMe)-Bip(2F) |
| 44 | HAQGT-(2F-Phe)-TSD-Bip(OMe)-Bip(2CF$_3$) |
| 45 | H-Aib-QGT-(2F-Phe)-TSD-Bip(OMe)-Bip(2Me) |
| 46 | H-Aib-QGT-(2F-Phe)-TSD-Bip(OMe)-Bip(Pyr) |

TABLE 2-continued

List of peptidomimetics prepared

| Seq. ID. No. | Sequence of peptidomimetics |
|---|---|
| 47 | H-Aib-QGT-(2F-Phe)-TSD-Bip(OMe)-Bip(2F) |
| 48 | H-Aib-QGT-(2F-Phe)-TSD-Bip(OMe)-Bip(2CF$_3$) |
| 49 | H-(ACP)-QGT-(2F-Phe)-TSD-Bip(OMe)-Bip(2Me) |
| 50 | H-(ACP)-QGT-(2F-Phe)-TSD-Bip(OMe)-Bip(Pyr) |
| 51 | H-(ACP)-QGT-(2F-Phe)-TSD7Bip(OMe)-Bip(2F) |
| 52 | H-(ACP)-QGT-(2F-Phe)-TSD-Bip(OMe)-Bip(2CF$_3$) |

(iv):

| Seq. ID. No. | Sequence of peptidomimetics |
|---|---|
| 53 | HS-(CNB)-GTFTSD-Bip(OMe)-Bip(2Me) |
| 54 | HS-(CNB)-GTFTSD-Bip(OMe)-Bip(Pyr) |
| 55 | HS-(CNB)-GTFTSD-Bip(OMe)-Bip(2F) |
| 56 | HS-(CNB)-GTFTSD-Bip(OMe)-Bip(2CF$_3$) |
| 57 | HA-(CNB)-GTFTSD-Bip(OMe)-Bip(2Me) |
| 58 | HA-(CNB)-GTFTSD-Bip(OMe)-Bip(Pyr) |
| 59 | HA-(CNB)-GTFTSD-Bip(OMe)-Bip(2F) |
| 60 | HA-(CNB)-GTFTSD-Bip(OMe)-Bip(2CF$_3$) |
| 61 | H-Aib-(CNB)-GTFTSD-Bip(OMe)-Bip(2Me) |
| 62 | H-Aib-(CNB)-GTFTSD-Bip(OMe)-Bip(Pyr) |
| 63 | H-Aib-(CNB)-GTFTSD-Bip(OMe)-Bip(2F) |
| 64 | H-Aib-(CNB)-GTFTSD-Bip(OMe)-Bip(2CF$_3$) |
| 65 | H-(ACP)-(CNB)-GTFTSD-Bip(OMe)43ip(2Me) |
| 66 | H-(ACP)-(CNB)-GTFTSD-Bip(OMe)-Bip(Pyr) |
| 67 | H-(ACP)-(CNB)-GTFTSD-Bip(OMe)-Bip(2F) |
| 68 | H-(ACP)-(CNB)-GTFTSD-Bip(OMe)-Bip(2CF$_3$) |
| 69 | HS-(CNB)-GT-(α-Me-2F-Phe)-TSD-Bip(OMe)-Bip(2Me) |
| 70 | HS-(CNB)-GT-(α-Me-2F-Phe)-TSD-Bip(OMe)-Bip(Pyr) |
| 71 | HS-(CNB)-GT-(α-Me-2F-Phe)-TSD-Bip(OMe)-Bip(2F) |
| 72 | HS-(CNB)-GT-(α-Me-2F-Phe)-TSD-Bip(OMe)-Bip(2CF$_3$) |
| 73 | HA-(CNB)-GT-(α-Me-2F-Phe)-TSD-Bip(OMe)-Bip(2Me) |
| 74 | HA-(CNB)-GT-(α-Me-2F-Phe)-TSD-Bip(OMe)-Bip(Pyr) |
| 75 | HA-(CNB)-GT-(α-Me-2F-Phe)-TSD-Bip(OMe)-Bip(2F) |
| 76 | HA-(CNB)-GT-(α-Me-2F-Phe)-TSD-Bip(OMe)-Bip(2CF$_3$) |
| 77 | H-Aib-(CNB)-GT-(α-Me-2F-Phe)-TSD-Bip(OMe)-Bip(2Me) |
| 78 | H-Aib-(CNB)-GT-(α-Me-2F-Phe)-TSD-Bip(OMe)-Bip(Pyr) |
| 79 | H-Aib-(CNB)-GT-(α-Me-2F-Phe)-TSD-Bip(OMe)-Bip(2F) |
| 80 | H-Aib-(CNB)-GT-(α-Me-2F-Phe)-TSD-Bip(OMe)-Bip(2CF$_3$) |
| 81 | H-(ACP)-(CNB)-GT-(α-Me-2F-Phe)-TSD-Bip(OMe)-Bip(2Me) |
| 82 | H-(ACP)-(CNB)-GT-(α-Me-2F-Phe)-TSD-Bip(OMe)-Bip(Pyr) |
| 83 | H-(ACP)-(CNB)-GT-(α-Me-2F-Phe)-TSD-Bip(OMe)-Bip(2F) |

TABLE 2-continued

List of peptidomimetics prepared

| Seq. ID. No. | Sequence of peptidomimetics |
|---|---|
| 84 | H-(ACP)-(CNB)-GT-(α-Me-2F-Phe)TSD-Bip(OMe)-Bip(2CF$_3$) |
| 85 | HS-(CNB)-GT-(2F-Phe)-TSD-Bip(OMe)-Bip(2Me) |
| 86 | HS-(CNB)-GT-(2F-Phe)-TSD-Bip(OMe)-Bip(Pyr) |
| 87 | HS-(CNB)-GT-(2F-Phe)-TSD-Bip(OMe)-Bip(2F) |
| 88 | HS-(CNB)-GT-(2F-Phe)-TSD-Bip(OMe)-Bip(2CF$_3$) |
| 89 | HA-(CNB)-GT-(2F-Phe)-TSD-Bip(OMe)-Bip(2Me) |
| 90 | HA-(CNB)-GT-(2F-Phe)-TSD-Bip(OMe)-Bip(Pyr) |
| 91 | HA-(CNB)-GT-(2F-Phe)-TSD-Bip(OMe)-Bip(2F) |
| 92 | HA-(CNB)-GT-(2F-Phe)-TSD-Bip(OMe)-Bip(2CF$_3$) |
| 93 | H-Aib-(CNB)-GT-(2F-Phe)-TSD-Bip(OMe)-Bip(2Me) |
| 94 | H-Aib-(CNB)-GT-(2F-Phe)-TSD-Bip(OMe)-Bip(Pyr) |
| 95 | H-Aib-(CNB)-GT-(2F-Phe)-TSD-Bip(OMe)-Bip(2F) |
| 96 | H-Aib-(CNB)-GT-(2F-Phe)-TSD-Bip(OMe)-Bip(2CF$_3$) |
| 97 | H-(ACP)-(CNB)-GT-(2F-Phe)-TSD-Bip(OMe)-Bip(2Me) |
| 98 | H-(ACP)-(CNB)-GT-(2F-Phe)-TSD-Bip(OMe)-Bip(Pyr) |
| 99 | H-(ACP)-(CNB)-GT-(2F-Phe)-TSD-BiP(OMe)-Bip(2F) |
| 100 | H-(ACP)-(CNB)-GT-(2F-Phe)-TSD-Bip(OMe)-Bip(2CF$_3$) |
| (v): | |
| 101 | HSQ-(ACP)-TFTSD-Bip(OMe)-Bip(2Me) |
| 102 | HSQ-(ACP)-TFTSD-Bip(OMe)-Bip(Pyr) |
| 103 | HSQ-(ACP)-TFTSD-Bip(OMe)-Bip(2F) |
| 104 | HSQ-(ACP)-TFTSD-Bip(OMe)-Bip(2CF$_3$) |
| 105 | HAQ-(ACP)-TFTSD-Bip(OMe)-Bip(2Me) |
| 106 | HAQ-(ACP)-TFTSD-Bip(OMe)-Bip(Pyr) |
| 107 | HAQ-(ACP)-TFTSD-Bip(OMe)-Bip(2F) |
| 108 | HAQ-(ACP)-TFTSD-Bip(OMe)-Bip(2CF$_3$) |
| 109 | H-Aib-Q-(ACP)-TFTSD-Bip(OMe)-Bip(2Me) |
| 110 | H-Aib-Q-(ACP)-TFTSD-Bip(OMe)-Bip(Pyr) |
| 111 | H-Aib-Q-(ACP)-TFTSD-Bip(OMe)-Bip(2F) |
| 112 | H-Aib-Q-(ACP)-TFTSD-Bip(OMe)-Bip(2CF$_3$) |
| 113 | H-(ACP)-Q-(ACP)-TFTSD-Bip(OMe)-Bip(2Me) |
| 114 | H-(ACP)-Q-(ACP)-TFTSD-Bip(OMe)-Bip(Pyr) |
| 115 | H-(ACP)-Q-(ACP)-TFTSD-Bip(OMe)-Bip(2F) |
| 116 | H-(ACP)-Q-(ACP)-TFTSD-Bip(OMe)-Bip(2CF$_3$) |
| 117 | HSQ-(ACP)-T-(α-Me-2F-Phe)-TSD-Bip(OMe)-Bip(2Me) |
| 118 | HSQ-(ACP)-T-(α-Me-2F-Phe)-TSD-Bip(OMe)-Bip(Pyr) |
| 119 | HSQ-(ACP)-T-(α-Me-2F-Phe)-TSD-Bip(OMe)-Bip(2F) |
| 120 | HSQ-(ACP)-T-(α-Me-2F-Phe)-TSD-Bip(OMe)-Bip(2CF$_3$) |

TABLE 2-continued

List of peptidomimetics prepared

| Seq. ID. No. | Sequence of peptidomimetics |
|---|---|
| 121 | HAQ-(ACP)-T-(α-Me-2F-Phe)-TSD-Bip(OMe)-Bip(2Me) |
| 122 | HAQ-(ACP)-T-(α-Me-2F-Phe)-TSD-Bip(OMe)-Bip(Pyr) |
| 123 | HAQ-(ACP)-T-(α-Me-2F-Phe)-TSD-Bip(OMe)-Bip(2F) |
| 124 | HAQ-(ACP)-T-(α-Me-2F-Phe)-TSD-Bip(OMe)-Bip(2CF$_3$) |
| 125 | H-Aib-Q-(ACP)-T-(α-Me-2F-Phe)-TSD-Bip(OMe)-Bip(2Me) |
| 126 | H-Aib-Q-(ACP)-T-(α-Me-2F-Phe)-TSD-Bip(OMe)-Bip(Pyr) |
| 127 | H-Aib-Q-(ACP)-T-(α-Me-2F-Phe)-TSD-Bip(OMe)-Bip(2F) |
| 128 | H-Aib-Q-(ACP)-T-(α-Me-2F-Phe)-TSD-Bip(OMe)-Bip(2CF$_3$) |
| 129 | H-(ACP)-Q-(ACP)-T (α-Me-2F-Phe)-TSD-Bip(OMe)-Bip(2Me) |
| 130 | H-(ACP)-Q-(ACP)-T-(α-Me-2F-Phe)-TSD-Bip(OMe)-Bip(Pyr) |
| 131 | H-(ACP)-Q-(ACP)-T-(α-Me-2F-Phe)-TSD-Bip(OMe)-Bip(2F) |
| 132 | H-(ACP)-Q-(ACP)-T-(α-Me-2F-Phe)-TSD-Bip(OMe)-Bip(2CF$_3$) |
| 133 | HSQ-(ACP)-T-(2F-Phe)-TSD-Bip(OMe)-Bip(2Me) |
| 134 | HSQ-(ACP)-T-(2F-Phe)-TSD-Bip(OMe)-Bip(Pyr) |
| 135 | HSQ-(ACP)-T-(2F-Phe)-TSD-Bip(OMe)-Bip(2F) |
| 136 | HSQ-(ACP)-T-(2F-Phe)-TSD-Bip(OMe)-Bip(2CF$_3$) |
| 137 | HAQ-(ACP)-T-(2F-Phe)-TSD-Bip(OMe)-Bip(2Me) |
| 138 | HAQ-(ACP)-T-(2F-Phe)-TSD-Bip(OMe)-Bip(Pyr) |
| 139 | HAQ-(ACP)-T-(2F-Phe)-TSD-Bip(OMe)-Bip(2F) |
| 140 | HAQ-(ACP)-T-(2F-Phe)-TSD-Bip(OMe)-Bip(2CF$_3$) |
| 141 | H-Aib-Q-(ACP)-T-(2F-Phe)-TSD-Bip(OMe)-Bip(2Me) |
| 142 | H-Aib-Q-(ACP)-T-(2F-Phe)-TSD-Bip(OMe)-Bip(Pyr) |
| 143 | H-Aib-Q-(ACP)-T-(2F-Phe)-TSD-Bip(OMe)-Bip(2F) |
| 144 | H-Aib-Q-(ACP)-T-(2F-Phe)-TSD-Bip(OMe)-Bip(2CF$_3$) |
| 145 | H-(ACP)-Q-(ACP)-T-(2F-Phe)-TSD-Bip(OMe)-Bip(2Me) |
| 146 | H-(ACP)-Q-(ACP)-T-(2F-Phe)-TSD-Bip(OMe)-Bip(Pyr) |
| 147 | H-(ACP)-Q-(ACP)-T-(2F-Phe)-TSD-Bip(OMe)-Bip(2F) |
| 148 | H-(ACP)-Q-(ACP)-T-(2F-Phe)-TSD-Bip(OMe)-Bip(2CF$_3$) |
| (vi): | |
| 149 | HSQG-(PCA)-FTSD-Bip(OMe)-Bip(2Me) |
| 150 | HSQG-(PCA)-FTSD-Bip(OMe)-Bip(Pyr) |
| 151 | HSQG-(PCA)-FTSD-Bip(OMe)-Bip(2F) |
| 152 | HSQG-(PCA)-FTSD-Bip(OMe)-Bip(2CF$_3$) |
| 153 | HAQG-(PCA)-FTSD-Bip(OMe)-Bip(2Me) |
| 154 | HAQG-(PCA)-FTSD-Bip(OMe)-Bip(Pyr) |
| 155 | HAQG-(PCA)-FTSD-Bip(OMe)-Bip(2F) |
| 156 | HAQG-(PCA)-FTSD-Bip(OMe)-Bip(2CF$_3$) |
| 157 | H-Aib-QG-(PCA)-FTSD-Bip(OMe)-Bip(2Me) |

TABLE 2-continued

List of peptidomimetics prepared

| Seq. ID. No. | Sequence of peptidomimetics |
|---|---|
| 158 | H-Aib-QG-(PCA)-FTSD-Bip(OMet)-Bip(Pyr) |
| 159 | H-Aib-QG-(PCA)-FTSD-Bip(OMe)-Bip(2F) |
| 160 | H-Aib-QG-(PCA)-FTSD-Bip(OMe)-Bip(2CF$_3$) |
| 161 | H-(ACP)-QG-(PCA)-FTSD-Bip(OMe)-Bip(2Me) |
| 162 | H-(ACP)-QG-(PCA)-FTSD-Bip(OMe)-Bip(Pyr) |
| 163 | H-(ACP)-QG-(PCA)-FTSD-Bip(OMe)-Bip(2F) |
| 164 | H-(ACP)-QG-(PCA)-FTSD-Bip(OMe)-Bip(2CF$_3$) |
| 165 | HSQG-(PCA)-(α-Me-2F-Phe)-TSD-Bip(OMe)-Bip(2Me) |
| 166 | HSQG-(PCA)-(α-Me-2F-Phe)-TSD-Bip(OMe)-Bip(Pyr) |
| 167 | HSQG-(PCA)-(α-Me-2F-Phe)-TSD-Bip(OMe)-Bip(2F) |
| 168 | HSQG-(PCA)-(α-Me-2F-Phe)-TSD-Bip(OMe)-Bip(2CF$_3$) |
| 169 | HAQG-(PCA)-(α-Me-2F-Phe)-TSD-Bip(OMe)-Bip(2Me) |
| 170 | HAQG-(PCA)-(α-Me-2F-Phe)-TSD-Bip(OMe)-Bip(Pyr) |
| 171 | HAQG-(PCA)-(α-Me-2F-Phe)-TSD-Bip(OMe)-Bip(2F) |
| 172 | HAQG-(PCA)-(α-Me-2F-Phe)-TSD-Bip(OMe)-Bip(2CF$_3$) |
| 173 | H-Aib-QG-(PCA)-(α-Me-2F-Phe)-TSD-Bip(OMe)-Bip(2Me) |
| 174 | H-Aib-QG-(PCA)-(α-Me-2F-Phe)-TSD-Bip(OMe)-Bip(Pyr) |
| 175 | H-Aib-QG-(PCA)-(α-Me-2F-Phe)-TSD-Bip(OMe)-Bip(2F) |
| 176 | H-Aib-QG-(PCA)-(α-Me-2F-Phe)-TSD-Bip(OMe)-Bip(2CF$_3$) |
| 177 | H-(ACP)-QG-(PCA)-(α-Me-2F-Phe)-TSD-Bip(OMe)-Bip(2Me) |
| 178 | H-(ACP)-QG-(PCA)-(α-Me-2F-Phe)-TSD-Bip(OMe)-Bip(Pyr) |
| 179 | H-(ACP)-QG-(PCA)-(α-Me-2F-Phe)-TSD-Bip(OMe)-Bip(2F) |
| 180 | H-(ACP)-QG-(PCA)-(α-Me-2F-Phe)-TSD-Bip(OMe)-Bip(2CF$_3$) |
| 181 | HSQG-(PCA)-(2F-Phe)-TSD-Bip(OMe)-Bip(2Me) |
| 182 | HSQG-(PCA)-(2F-Phe)-TSD-Bip(OMe)-Bip(Pyr) |
| 183 | HSQG-(PCA)-(2F-Phe)-TSD-Bip(OMe)-Bip(2F) |
| 184 | HSQG-(PCA)-(2F-Phe)-TSD-Bip(OMe)-Bip(2CF$_3$) |
| 185 | HAQG-(PCA)-(2F-Phe)-TSD-Bip(OMe)-Bip(2Me) |
| 186 | HAQG-(PCA)-(2F-Phe)-TSD-Bip(OMe)-Bip(Pyr) |
| 187 | HAQG-(PCA)-(2F-Phe)-TSD-Bip(OMe)-Bip(2F) |
| 188 | HAQG-(PCA)-(2F-Phe)-TSD-Bip(OMe)-Bip(2CF$_3$) |
| 189 | H-Aib-QG-(PCA)-(2F-Phe)-TSD-Bip(OMe)-Bip(2Me) |
| 190 | H-Aib-QG-(PCA)-(2F-Phe)-TSD-Bip(OMe)-Bip(Pyr) |
| 191 | H-Aib-QG-(PCA)-(2F-Phe)-TSD-Bip(OMe)-Bip(2F) |
| 192 | H-Aib-QG-(PCA)-(2F-Phe)-TSD-Bip(OMe)-Bip(2CF$_3$) |
| 193 | H-(ACP)-QG-(PCA)-(2F-Phe)-TSD-Bip(OMe)-Bip(2Me) |
| 194 | H-(ACP)-QG-(PCA)-(2F-Phe)-TSD-Bip(OMe)-Bip(Pyr) |

TABLE 2-continued

List of peptidomimetics prepared

| Seq. ID. No. | Sequence of peptidomimetics |
|---|---|
| 195 | H-(ACP)-QG-(PCA)-(2F-Phe)-TSD-Bip(OMe)-Bip(2F) |
| 196 | H-(ACP)-QG-(PCA)-(2F-Phe)-TSD-Bip(OMe)-Bip(2CF$_3$) |

In Vitro and In Vivo Studies of Novel Peptidomimetics:

The peptidomimetics prepared as described above were tested for a) In vitro glucose-dependent insulin secretion (RIN5F cell assay screening protocol);
b) In vitro Human GLP-1 R agonist activity (Cyclic AMP determination);
c) In vitro human glucagon antagonist activity (Cyclic AMP determination);
d) Stability of peptidomimetics against DPP IV enzyme, human plasma, simulated gastric fluid, intestinal fluid and liver microsomes; and
e) Demonstration of in vivo efficacy of test compounds (peptidomimetics) in C57BL/6J mice (in vivo), using various in vitro and in vivo assays, as described below.

In Vitro Studies:

In Vitro Glucose-Dependent Insulin Secretion (RIN5F Cell Assay Screening Protocol)

RIN5F (Rat Insulinoma) cells were cultured in RPMI 1640 medium supplemented with sodium pyruvate (1 mM) HEPES and Glucose (4.5 g/L) in a humidified incubator (5% $CO_2$), at 37° C. After trypsinization, RIN5F cells were seeded at a concentration of $0.2 \times 10^6$·cells per well, in 12 well plates. The cells were grown overnight to 80% confluence and insulin secretion experiments were performed as follows (Montrose-Rafizadeh C., et al., Mol. Cell. Endo. 1997, 130, 109; Wang, X., et al., Endocrinology 2001, 5, 1820).

Cells were washed once with PBS solution followed by 40 min. incubation in fresh Krebs-Ringer Balanced Buffer containing NaCl (115 mmol/L), KCl (4.7 mmol/L), $CaCl_2$ (1.28 mmol/L), $MgSO_4 \cdot 7H_2O$ (1.2 mmol/L), $KH_2PO_4$ (1.2 mmol/L), $NaHCO_3$ (10 mmol/L) and HEPES (25 mmol/L), containing Glucose (1.1 mM) and B.S.A (0.5%), pH 7.4. The buffer was replaced after 40 min. and the cells were incubated (37° C.) with the test peptidomimetics, at different concentration, for 30 min., both in the presence (16.7 mM) and absence (0 mM) of glucose load. The supernatant was collected and the insulin amount was measured by ultra sensitive Rat insulin ELISA kit (Crystal Chem, Ill.). The protein was estimated in the supernatant using Bicinchoninic Acid kit, according to the manufacturer's protocol (Sigma Aldrich, Mo.). The total insulin content obtained in Pico-gram (pg) was divided with the total protein (µg) in order to normalize for differences in cell density between wells. In vitro glucose dependent insulin secretion activity of representative peptidomimetics are listed in [Table 3].

TABLE 3

In vitro glucose dependent insulin secretion activity of representative peptidomimetics

| Seq. ID. No. | Conc. of test compd. (nM) | Insulin secretion (pg/µg/hr)* |
|---|---|---|
| Control 1 (0 mM glucose) | | 5.8 ± 0.66 |
| Control 2 (16.7 mM glucose) | | 10.6 ± 0.62 |
| Exendin-4 | 0.1/1/10 | 16.3 ± 0.61/22.4 ± 0.52/36.5 ± 0.36 |
| 5 | 0.1/1/10 | 12.1 ± 0.52/14.1 ± 0.16/28.0 ± 0.36 |
| 6 | 0.1/1/10 | 12.4 ± 0.26/15.2 ± 0.33/29.6 ± 0.51 |
| 7 | 0.1/1/10 | 11.1 ± 0.12/13.1 ± 0.13/19.0 ± 0.16 |
| 8 | 0.1/1/10 | 12.6 ± 0.20/15.9 ± 0.31/28.4 ± 0.11 |
| 9 | 0.1/1/10 | 11.8 ± 0.50/14.9 ± 0.11/27.9 ± 0.31 |
| 10 | 0.1/1/10 | 12.7 ± 0.21/15.8 ± 0.33/29.3 ± 0.19 |
| 11 | 0.1/1/10 | 13.1 ± 0.11/14.9 ± 0.17/28.8 ± 0.44 |
| 12 | 0.1/1/10 | 12.9 ± 0.14/15.8 ± 0.13/29.9 ± 0.15 |
| 13 | 0.1/1/10 | 16.1 ± 0.22/22.1 ± 0.26/36.0 ± 0.36 |
| 14 | 0.1/1/10 | 15.4 ± 0.14/21.2 ± 0.18/35.6 ± 0.17 |
| 15 | 0.1/1/10 | 15.6 ± 0.33/21.8 ± 0.16/35.6 ± 0.26 |
| 16 | 0.1/1/10 | 16.6 ± 0.41/22.9 ± 0.32/36.7 ± 0.11 |
| 17 | 0.1/1/10 | 16.5 ± 0.12/22.7 ± 0.17/36.5 ± 0.05 |
| 18 | 0.1/1/10 | 16.2 ± 0.13/22.4 ± 0.19/36.2 ± 0.09 |
| 19 | 0.1/1/10 | 17.1 ± 0.15/23.1 ± 0.12/37.0 ± 0.19 |
| 20 | 0.1/1/10 | 16.9 ± 0.22/22.8 ± 0.31/36.7 ± 0.34 |
| 21 | 0.1/1/10 | 12.3 ± 0.33/14.1 ± 0.36/28.0 ± 0.16 |
| 22 | 0.1/1/10 | 12.1 ± 0.42/14.6 ± 0.41/27.8 ± 0.46 |
| 23 | 0.1/1/10 | 11.9 ± 0.17/14.2 ± 0.13/27.6 ± 0.16 |
| 24 | 0.1/1/10 | 12.3 ± 0.33/14.8 ± 0.16/28.1 ± 0.22 |
| 25 | 0.1/1/10 | 12.4 ± 0.22/15.2 ± 0.32/29.6 ± 0.50 |
| 26 | 0.1/1/10 | 12.1 ± 0.51/14.1 ± 0.19/28.1 ± 0.29 |
| 27 | 0.1/1/10 | 12.6 ± 0.25/15.3 ± 0.31/29.7 ± 0.48 |
| 28 | 0.1/1/10 | 12.0 ± 0.14/14.3 ± 0.12/27.8 ± 0.32 |
| 29 | 0.1/1/10 | 16.2 ± 0.20/22.2 ± 0.20/36.1 ± 0.31 |
| 30 | 0.1/1/10 | 15.3 ± 0.19/21.2 ± 0.11/35.5 ± 0.19 |
| 31 | 0.1/1/10 | 15.6 ± 0.31/21.8 ± 0.16/35.6 ± 0.28 |
| 32 | 0.1/1/10 | 16.6 ± 0.41/22.9 ± 0.32/36.6 ± 0.19 |
| 33 | 0.1/1/10 | 16.4 ± 0.12/22.7 ± 0.17/36.6 ± 0.05 |
| 34 | 0.1/1/10 | 16.3 ± 0.15/22.4 ± 0.21/36.2 ± 0.11 |
| 35 | 0.1/1/10 | 17.1 ± 0.11/23.1 ± 0.16/37.0 ± 0.29 |
| 36 | 0.1/1/10 | 16.8 ± 0.20/22.7 ± 0.29/36.6 ± 0.31 |

*In vitro glucose dependent (16.7-mM glucose load) insulin secretion with various concentrations of peptidomimetics were measured using Rat Insulinoma (RIN5F) cells. The total insulin content (pg) was divided with total protein (µg) to normalize difference in cell density between wells. n = 3, values represent mean ± .S.D. Basal insulin secretion was observed for all the test compounds at 0-mM glucose concentration.

In vitro Human GLP-1 R Agonist Activity (Cyclic AMP Determination).

The novel peptidomimetics were screened for Human GLP-1 receptor (HGLP-1 R) agonist activity (in vitro), using the cAMP cell-based assay, in stably transfected CHO/human GLP1R cells. The CHO-K1 cells (CRL 9618), were obtained from American Type Culture Collection (Rockville, Md.). CHO cells were grown in Ham's F12 medium containing L-Glutamine (2 mM), HEPES (25 mM), $NaHCO_3$ (1.1 g/L) and supplemented with NewBorn Calf Serum (NBCS; 10%), Penicillin (50 U/ml (v/v)) and Streptomycin (50 ug/ml (v/v)). Cells were split every 3 days 1:8.

Production of Stable CHO Cell Lines Expressing the Human GLP-1 Receptor.

The cDNA encoding the human GLP-1 receptor was isolated by RT-PCR according to standard protocol. The full-length cDNA was cloned in pcDNA3.1(+). For the production of CHO cell lines expressing the GLP-1 receptor, CHO cells were transfected with 10 μg of the expression plasmid pcDNA/hGLP-1R using CaPO$_4$ according to the standard protocol (Wheeler, M. B., et al., Endocrinology 1993, 133, 57.). Clones expressing the receptor were generated by G418 (800 μg/ml active, Sigma) selection. The stable clones were thereafter maintained at 500 ug/ml (G418). The selected clone was used between passages 9-25 for cAMP assays.

Determination of cAMP Generation.

The CHO cells stably transfected with human GLP-1R were maintained in Ham's F12+10% NBCS+500 ug/ml G418 upto a confluency of 70-75%. The cells were trypsinized using 2 ml of TPVG (0.25% trypsin, 0:53 mM EDTA, 1.38-mM glucose). The trypsin was inactivated using Ham's F12 medium containing 10% NBCS and the cells were suspended in 2 ml of complete medium. 2×10$^5$ cells/well were then seeded in 12 well plate and the plates were incubated in humidified atmosphere at 37° C. for 16-18 h (Fehmann, H. C., et al., Peptides 1994, 15, 453). The next day the assay was proceeded, when the cells showed 90-95% confluency. The medium was aspirated off from the 12 well plate and the cells were washed once using Ham's F12 (plain). The cells were incubated at 37° C. with 500 ul of Ham's F12+1% BSA+0.125 mM RO-20 for 30 min. After the incubation, the medium was aspirated off and fresh medium (plain Ham's F12+1% BSA+0.25 mM RO-20) was added with 5 ul of test compounds (peptidomimetics) that has been dissolved in water (MilliQ). The cells were incubated with the test compounds for 30 min in humidified atmosphere and 37° C. After the incubation, the medium was removed and cells were washed once with plain Ham's F12. Subsequently, the cells were lysed by adding 500 ul of ice cold 0.1 N HCl to each well and shaking for 30 minutes at 200 rpm. The cells were then scrapped, the lysate was collected in micro centrifuge tubes and centrifuged at 12000 rpm for 10 min to remove the debris. 300 ul of supernatant from each micro-centrifuge tube was then removed into a glass tube and dried under N$_2$ for 30 min, for cAMP estimation. The total cAMP was estimated from the sample according to the manufacturer's protocol using Cyclic AMP immunoassay kit (R&D systems, Minneapolis. MN). The remaining supernatant is used to determine the protein concentration using micro BCA (Sigma). Data is calculated as percent of control (Vehicle: water) and expressed as Mean±SD. The in-vitro human GLP-1 receptor agonistic activities of representative peptidomimetics are listed in Table 4.

TABLE 4

In vitro Human GLP-1 R activity (cAMP release) of test compounds (peptidomimetics), shown as % activity with respect to control.

| Seq. ID. No. | Concentration of test compounds | | | | |
|---|---|---|---|---|---|
| | 1 nM | 10 nM | 100 nM | 1 μM | 10 μM |
| Exendin-4 | 89 ± 0.15 | 96 ± 0.18 | 99 ± 0.03 | 99 ± 0.09 | 99 ± 0.06 |
| 5 | 38 ± 0.12 | 78 ± 0.15 | 86 ± 0.18 | 95 ± 0.03 | 98 ± 0.09 |
| 6 | 39 ± 0.11 | 80 ± 0.09 | 88 ± 0.06 | 96 ± 0.14 | 99 ± 0.19 |
| 7 | 45 ± 0.022 | 84 ± 0.46 | 90 ± 0.41 | 99 ± 0.66 | 99 ± 0.03 |
| 8 | 40 ± 0.09 | 81 ± 0.07 | 87 ± 0.04 | 95 ± 0.01 | 98 ± 0.08 |
| 9 | 38 ± 0.11 | 77 ± 0.16 | 85 ± 0.11 | 94 ± 0.08 | 97 ± 0.05 |
| 10 | 39 ± 0.10 | 81 ± 0.08 | 89 ± 0.09 | 96 ± 0.11 | 99 ± 0.16 |
| 11 | 51 ± 0.03 | 86 ± 0.40 | 91 ± 0.21 | 99 ± 0.32 | 99 ± 0.21 |
| 12 | 55 ± 0.16 | 89 ± 0.05 | 93 ± 0.09 | 99 ± 0.02 | 99 ± 0.04 |
| 13 | 60 ± 0.12 | 92 ± 0.15 | 98 ± 0.18 | 99 ± 0.03 | 99 ± 0.09 |
| 14 | 62 ± 0.11 | 94 ± 0.09 | 99 ± 0.06 | 99 ± 0.14 | 99 ± 0.19 |
| 15 | 66 ± 0.022 | 97 ± 0.46 | 99 ± 0.41 | 99 ± 0.66 | 99 ± 0.03 |
| 16 | 69 ± 0.09 | 98 ± 0.07 | 99 ± 0.04 | 99 ± 0.01 | 99 ± 0.08 |
| 17 | 78 ± 0.12 | 99 ± 0.15 | 99 ± 0.18 | 99 ± 0.03 | 99 ± 0.09 |
| 18 | 86 ± 0.11 | 99 ± 0.09 | 99 ± 0.06 | 99 ± 0.14 | 99 ± 0.19 |
| 19 | 96 ± 0.02 | 99 ± 0.46 | 99 ± 0.41 | 99 ± 0.66 | 99 ± 0.03 |
| 20 | 96 ± 0.09 | 99 ± 0.07 | 99 ± 0.04 | 99 ± 0.01 | 99 ± 0.08 |
| 21 | 39 ± 0.12 | 80 ± 0.15 | 86 ± 0.18 | 95 ± 0.03 | 98 ± 0.09 |
| 22 | 40 ± 0.11 | 81 ± 0.09 | 89 ± 0.06 | 96 ± 0.14 | 99 ± 0.19 |
| 23 | 46 ± 0.022 | 85 ± 0.46 | 90 ± 0.41 | 99 ± 0.66 | 99 ± 0.03 |
| 24 | 41 ± 0.09 | 82 ± 0.07 | 87 ± 0.04 | 95 ± 0.01 | 98 ± 0.08 |
| 25 | 38 ± 0.11 | 77 ± 0.16 | 85 ± 0.11 | 94 ± 0.08 | 97 ± 0.05 |
| 26 | 39 ± 0.10 | 81 ± 0.08 | 89 ± 0.09 | 96 ± 0.11 | 99 ± 0.16 |
| 27 | 82 ± 0.22 | 87 ± 0.12 | 92 ± 0.14 | 99 ± 0.22 | 99 ± 0.26 |
| 28 | 55 ± 0.16 | 88 ± 0.13 | 92 ± 0.11 | 99 ± 0.07 | 99 ± 0.09 |
| 29 | 99 ± 0.12 | 99 ± 0.15 | 99 ± 0.18 | 99 ± 0.03 | 99 ± 0.09 |
| 30 | 93 ± 0.11 | 99 ± 0.09 | 99 ± 0.06 | 99 ± 0.14 | 99 ± 0.19 |
| 31 | 93 ± 0.10 | 99 ± 0.46 | 99 ± 0.41 | 99 ± 0.66 | 99 ± 0.03 |
| 32 | 99 ± 0.06 | 99 ± 0.06 | 99 ± 0.08 | 99 ± 0.10 | 99 ± 0.12 |
| 33 | 99 ± 0.11 | 99 ± 0.13 | 99 ± 0.16 | 99 ± 0.06 | 99 ± 0.10 |
| 34 | 99 ± 0.12 | 99 ± 0.08 | 99 ± 0.11 | 99 ± 0.12 | 99 ± 0.16 |
| 35 | 99 ± 0.02 | 99 ± 0.26 | 99 ± 0.31 | 99 ± 0.60 | 99 ± 0.08 |
| 36 | 96 ± 0.09 | 99 ± 0.07 | 99 ± 0.04 | 99 ± 0.01 | 99 ± 0.08 |

Based upon, the in-vitro human GLP-1 receptor agonistic activity, EC$_{50}$ values were determined for novel peptidomimetics and the comparative dose-response curve (DRC) of Exendin and Seq. ID. No. 32 is shown in FIG. 7 as representative example.

In Vitro Human Glucagon Antagonist Activity (Measurement of Inhibition of Amount of Cyclic AMP Production, with Test Peptidomimetics).

The novel peptidomimetics were screened for human glucagon receptor (H-glucagon-R) antagonistic activity (in vitro), using the cAMP cell-based assay, in stably transfected CHO/human glucagon R cells. The CHO-K1 cells (CRL 9618) were obtained from American Type Culture Collection (Rockville, Md.). CHO cells were grown in Ham's F12 medium containing L-Glutamine (2 mM), HEPES (25 mM), NaHCO$_3$ (1.1 g/L) and supplemented with newborn Calf Serum (NBCS; 10%), Penicillin (50 U/ml (v/v)) and Streptomycin (50 ug/ml (v/v)). Cells were split every 3 days 1:8.

Production of Stable CHO Cell Lines Expressing the Human Glucagon Receptor.

The cDNA encoding the human glucagon receptor was isolated by RT-PCR according to standard protocol. The full-length cDNA was cloned in pcDNA3.1(Invitrogen). For the production of CHO cell lines expressing the glucagon receptor, CHO cells were transfected with 10 μg of the expression plasmid pcDNA/H-glucagon-R using CaPO$_4$ according to the standard protocol. Clones expressing the receptor were generated by G418 (800 μg/ml active, Sigma) selection. The stable clones were thereafter maintained at 500 ug/ml (G418). The selected clone was used between passages 9-25 for cAMP assays.

Determination of Glucagon Antagonistic Activity by Measuring Amount of cAMP Production Inhibited after Addition of Test Peptidomimetics Along with Glucagon Peptide.

The CHO cells stably transfected with human glucagon R were maintained in Ham's F12+10% NBCS+500 ug/ml G418 upto a confluency of 70-75%. The cells were trypsinized using 2 ml of TPVG (0.25% trypsin, 0.53 mM EDTA, 1.38-mM glucose). The trypsin was inactivated using Ham's F12 medium containing 10% NBCS and the cells were suspended in 2 ml of complete medium. 2×10$^5$ cells/well were then seeded in 12 well plate and the plates were incubated in humidified atmosphere at 37° C. for 16-18 h. The next day the assay was proceeded, when the cells showed 90-95% confluency. The medium was aspirated off from the 12 well plate and the cells were washed once using Ham's F12 (plain). The cells were incubated at 37° C. with 500 ul of Ham's F12+1% BSA+0.125 mM RO-20 for 30 min. After the incubation, the medium was aspirated off and fresh medium (plain Ham's F12+1% BSA+0.25 mM RO-20) was added with 5 ul of test compounds (peptidomimetics) that has been dissolved in water (MilliQ), followed by addition of glucagon peptide (as agonist). The cells were incubated with the peptidomimetics and glucagon peptide for 30 min in humidified atmosphere and 37° C. After the incubation; the medium was removed and cells were washed once with plain Ham's F12. Subsequently, the cells were lysed by adding 500 ul of ice cold 0.1 N HCl to each well and shaking for 30 minutes at 200 rpm. The cells were then scrapped, the lysate was collected in micro centrifuge tubes and centrifuged at 12000 rpm for 10 min to remove the debris. 300 ul of supernatant from each micro-centrifuge tube was then removed into a glass tube and dried under $N_2$ for 30 min, for cAMP estimation. The total cAMP was estimated from the sample according to the manufacturer's protocol using Cyclic AMP immunoassay kit (R&D systems, Minneapolis: MN). The remaining supernatant is used to determine the protein concentration using micro BCA (Sigma). Data is calculated as percent of control (Vehicle: water) and expressed as Mean+SD. The in-vitro human glucagon receptor antagonistic activities of representative peptidomimetics are listed in Table 5.

Stability of Peptidomimetics Against DPP IV Enzyme, Human Plasma, Simulated Gastric Fluid, Intestinal Fluid and Liver Microsomes.

Different peptidomimetics (final concentration 2 μM) were incubated with either DPP IV (1:25 mU) or pooled human plasma (7.5 μL) or simulated gastric fluid (pH 1.5; composition HCl, NaCl and Pepsin) or simulated intestinal fluid (pH 7.5) or human liver microsomes, for 0, 2, 4, 6, 12 and 24 h (37° C.; 50 mM triethanolamine-HCl buffer; pH 7.8). Concentrations of DPP IV enzyme/human plasma/simulated gastric fluid/simulated intestinal fluid/human liver microsomes were selected in preliminary experiments to provide degradation of approximately 50% of Exendin within 2-4 h, therefore allowing time-dependent degradation to be viewed over 24 h. Reactions were terminated by the addition of TFA/$H_2O$ (15 mL, 10% (v/v)). The reaction products were then applied to a Vydac $C_{18}$ analytical column (4.6×250-mm) and the major degradation fragment separated from intact peptidomimetic. The column was equilibrated with TFA/$H_2O$, at a flow rate of 1 mL/min. Using 0.1% (v/v) TFA in 70% acetonitrile/$H_2O$, the concentration of acetonitrile in the eluting solvent was raised from 0% to 28% over 10 min and from 28% to 42% over 30 min. The absorbance was monitored at 206 nm using UV detector and peaks were collected manually prior to ESI-MS analysis. Area under the curve was measured for test peptidomimetics and their metabolites and percentage degradation were calculated at each time point over a period of 24 h. Stability study results of selected peptidomimetics, against

TABLE 5

In vitro Human Glucagon receptor antagonistic activity of test compounds (peptidomimetics) shown as inhibition of cAMP production (pmol/ml/μg prt) of Glucagon peptide, by the test compounds, incubated at different concentration, along with saturated concentration of glucagon peptide.

| Seq. ID. No. | Concentration of test compounds | | | | |
|---|---|---|---|---|---|
| | 1 nM | 10 nM | 100 nM | 1 nM | 10 μM |
| Glucagon | 22 ± 0.03 | 36 ± 0.07 | 36 ± 0.09 | 37 ± 0.12 | 37 ± 0.08 |
| 5 | 20 ± 0.06 | 18 ± 0.09 | 16 ± 0.01 | 14 ± 0.03 | 12 ± 0.01 |
| 6 | 22 ± 0.03 | 21 ± 0.05 | 20 ± 0.07 | 18 ± 0.04 | 18 ± 0.03 |
| 7 | 6 ± 0.02 | 5 ± 0.03 | 2 ± 0.61 | 0 | 0 |
| 8 | 4 ± 0.01 | 2 ± 0.17 | 0 | 0 | 0 |
| 9 | 18 ± 0.07 | 16 ± 0.01 | 12 ± 0.03 | 8 ± 0.02 | 6 ± 0.08 |
| 10 | 15 ± 0.11 | 12 ± 0.13 | 8 ± 0.09 | 4 ± 0.01 | 2 ± 0.08 |
| 11 | 10 ± 0.03 | 8 ± 0.03 | 6 ± 0.22 | 2 ± 0.13 | 0 |
| 12 | 5 ± 0.09 | 3 ± 0.11 | 0 | 0 | 0 |
| 13 | 10 ± 0.12 | 8 ± 0.02 | 6 ± 0.04 | 4 ± 0.05 | 1 ± 0.02 |
| 14 | 9 ± 0.11 | 6 ± 0.12 | 5 ± 0.14 | 3 ± 0.22 | 0 |
| 15 | 6 ± 0.01 | 5 ± 0.02 | 2 ± 0.13 | 0 | 0 |
| 16 | 4 ± 0.02 | 2 ± 0.15 | 0 | 0 | 0 |
| 17 | 2 ± 0.03 | 0 | 0 | 0 | 0 |
| 18 | 0 | 0 | 0 | 0 | 0 |
| 19 | 5 ± 0.04 | 3 ± 0.02 | 1 ± 0.11 | 0 | 0 |
| 20 | 5 ± 0.01 | 2 ± 0.17 | 0 | 0 | 0 |
| 21 | 19 ± 0.03 | 17 ± 0.08 | 15 ± 0.01 | 14 ± 0.02 | 12 ± 0.11 |
| 22 | 21 ± 0.11 | 19 ± 0.02 | 18 ± 0.07 | 18 ± 0.03 | 16 ± 0.02 |
| 23 | 4 ± 0.05 | 2 ± 0.13 | 2 ± 0.12 | 0 | 0 |
| 24 | 4 ± 0.09 | 2 ± 0.12 | 0 | 0 | 0 |
| 25 | 18 ± 0.12 | 16 ± 0.11 | 12 ± 0.13 | 8 ± 0.12 | 6 ± 0.18 |
| 26 | 15 ± 0.11 | 12 ± 0.13 | 8 ± 0.09 | 4 ± 0.01 | 2 ± 0.08 |
| 27 | 14 ± 0.02 | 11 ± 0.03 | 7 ± 0.22 | 3 ± 0.12 | 0 |
| 28 | 4 ± 0.06 | 3 ± 0.11 | 0 | 0 | 0 |
| 29 | 10 ± 0.16 | 8 ± 0.12 | 6 ± 0.14 | 4 ± 0.15 | 1 ± 0.12 |
| 30 | 9 ± 0.14 | 6 ± 0.14 | 5 ± 0.13 | 3 ± 0.24 | 0 |
| 31 | 6 ± 0.05 | 5 ± 0.04 | 2 ± 0.16 | 0 | 0 |
| 32 | 4 ± 0.16 | 2 ± 0.11 | 0 | 0 | 0 |
| 33 | 0 | 0 | 0 | 0 | 0 |
| 34 | 0 | 0 | 0 | 0 | 0 |
| 35 | 5 ± 0.04 | 3 ± 0.15 | 1 ± 0.15 | 0 | 0 |
| 36 | 3 ± 0.12 | 1 ± 0.12 | 0 | 0 | 0 |

DPP IV enzyme, human plasma, simulated gastric fluid, intestinal fluid and liver microsomes (in vitro) are listed in Table 6.

TABLE 6

Stability study results of selected peptidomimetics against DPP IV enzyme, human plasma, simulated gastric fluid, intestinal fluid and liver microsomes (in vitro)

| Seq. ID. No. | DPP IV enzyme[a] | Human plasma[b] | Simulated gastric fluid[c] | Simulated intestinal fluid[d] | liver microsomes[e] |
|---|---|---|---|---|---|
| EX-4 | 89 (6) | 86 (6.2) | 100 (0.3) | 100 (0.3) | 100 (0.4) |
| 5 | 76 (10) | 78 (9) | 100 (0.5) | 100 (0.5) | 100 (0.5) |
| 6 | 75 (10) | 77 (9) | 100 (0.5) | 100 (0.5) | 100 (0.5) |
| 7 | 77 (10) | 80 (9) | 100 (0.5) | 100 (0.5) | 100 (0.5) |
| 8 | 76 (10) | 78 (9) | 100 (0.5) | 100 (0.5) | 100 (0.5) |
| 9 | 74 (10) | 75 (9) | 100 (0.5) | 100 (0.5) | 100 (0.5) |
| 10 | 70 (10) | 71 (9) | 100 (0.5) | 100 (0.5) | 100 (0.5) |
| 11 | 86 (10) | 70 (9) | 100 (0.5) | 100 (0.5) | 100 (0.5) |
| 12 | 72 (10) | 70 (9) | 100 (0.5) | 100 (0.5) | 100 (0.5) |
| 13 | 00 (>24) | 00 (>24) | 50 (4) | 00 (>24) | 86 (2) |
| 14 | 00 (>24) | 00 (>24) | 55 (4) | 00 (>24) | 84 (2) |
| 15 | 00 (>24) | 00 (>24) | 45 (4) | 00 (>24) | 85 (2) |
| 16 | 00 (>24) | 00 (>24) | 43 (4) | 00 (>24) | 84 (2) |
| 17 | 00 (>24) | 00 (>24) | 49 (4) | 00 (>24) | 82 (2) |
| 18 | 00 (>24) | 00 (>24) | 52 (4) | 00 (>24) | 81 (2) |
| 19 | 00 (>24) | 00 (>24) | 43 (4) | 00 (>24) | 84 (2) |
| 20 | 00 (>24) | 00 (>24) | 41 (4) | 00 (>24) | 80 (2) |
| 21 | 76 (9) | 78 (8) | 12 (8) | 55 (6) | 79 (1) |
| 22 | 75 (9) | 77 (8) | 14 (8) | 45 (6) | 81 (1) |
| 23 | 77 (9) | 80 (8) | 13 (8) | 50 (6) | 82 (1) |
| 24 | 76 (9) | 78 (8) | 14 (8) | 43 (6) | 80 (1) |
| 25 | 74 (9) | 75 (8) | 12 (8) | 46 (6) | 83 (1) |
| 26 | 70 (9) | 71 (8) | 14 (8) | 40 (6) | 78 (1) |
| 27 | 86 (9) | 70 (8) | 15 (8) | 41 (6) | 77 (1) |
| 28 | 72 (9) | 70 (8) | 12 (8) | 42 (6) | 78 (1) |
| 29 | 00 (>24) | 00 (>24) | 00 (>24) | 00 (>24) | 35 (5) |
| 30 | 00 (>24) | 00 (>24) | 00 (>24) | 00 (>24) | 33 (5) |
| 31 | 00 (>24) | 00 (>24) | 00 (>24) | 00 (>24) | 31 (5) |
| 32 | 00 (>24) | 00 (>24) | 00 (>24) | 00 (>24) | 32 (5) |
| 33 | 00 (>24) | 00 (>24) | 00 (>24) | 00 (>24) | 33 (5) |
| 34 | 00 (>24) | 00 (>24) | 00 (>24) | 00 (>24) | 32 (5) |
| 35 | 00 (>24) | 00 (>24) | 00 (>24) | 00 (>24) | 26 (5) |
| 36 | 00 (>24) | 00 (>24) | 00 (>24) | 00 (>24) | 35 (5) |

[a]% degradation of peptidomimetics in 24 h when incubated with DPP-IV enzyme and values in bracket represent half-life ($t_{1/2}$), in h;
[b]% degradation of peptidomimetics in 24 h when incubated with human plasma and values in bracket represent half-life ($t_{1/2}$), in h;
[c]% degradation of peptidomimetics in 24 h when incubated with simulated gastric fluid and values in bracket represent half-life ($t_{1/2}$), in h;
[d]% degradation of peptidomimetics in 24 h when incubated with simulated intestinal fluid and values in bracket represent half-life ($t_{1/2}$), in h;
[e]% degradation of peptidomimetics in 24 h when incubated with liver microsomes and values in bracket represent half-life ($t_{1/2}$), in h.

In Vivo Efficacy Studies:
Demonstration of In Vivo Efficacy (Antihyperglycaemic/Antidiabetic Activity) of Test Compounds (Peptidomimetics) in CS7BL/6J or db/db Mice, Both by Parenteral (i.p) and Oral Routes of Administration.
Animals Acute single dose 120-min time-course experiments were carried out in male C57BL/6J or db/db mice, age 8-12 weeks, bred in-house. Animals were housed in groups of 6 animals per cage, for a week, in order to habituate them to vivarium conditions (25±4° C., 60-65% relative humidity, 12:12 h light:dark cycle, with lights on at 7.30 am). All the animal experiments were carried out according to the internationally valid guidelines following approval by the 'Zydus Research Center animal ethical committee'.

Procedure

The in-vivo glucose lowering properties of some of the test compounds (peptidomimetics) and Exendin-4 were evaluated in C57BL/6J (mild hyperglycemic) or db/db animal models as described below. Two days prior to the study, the animals were randomised and divided into 5 groups (n=6), based upon their fed glucose levels. On the day of experiment, food was withdrawn from all the cages, water was given ad-libitum and were kept for overnight fasting. Vehicle (normal saline)/test/standard compounds were administered intraperitoneally (i.p.) or orally, on a body weight basis. Soon after the 0 min. blood collection from each animal, the subsequent blood collections were done at 30, 60 and 120 or upto 240 min., via retro-orbital route, under light ether anesthesia (Chen, D., et al., Diabetes Obesity Metabolism, 2005, 7, 307. Kim, J. G. et al., Diabetes, 2003, 52, 751).

Blood samples were centrifuged and the separated serum was immediately subjected for the glucose estimation. Serum for insulin estimation was stored at −70° C. until used for the insulin estimation. The glucose estimation was carried out with DPEC-GOD/POD method (Ranbaxy Fine Chemicals Limited, Diagnostic division, India), using Spectramax-190, in 96-microwell plate reader (Molecular devices Corporation, Sunnyvale, Calif.). Mean values of duplicate samples were calculated using Microsoft excel and the Graph Pad Prism software (Ver. 4.0) was used to plot a 0 min base line corrected line graph, area under the curve (0-120 min AUC) and base line corrected area under the curve (0 min BCAUC). The AUC and BCAUC obtained from graphs were analyzed for one way ANOVA, followed by Dunnett's post test, using Graph Pad prism software. Furthermore, the insulin estimation was carried out using rat/mouse insulin ELISA kit (Linco research, Mo. USA). Changes in the blood glucose levels, at 0, 30, 60 and 120 min, with selected peptidomimetics are shown in Table 7 (via ip route of administration) and Table 8 (via oral route of administration) respectively.

TABLE 7

Acute single dose 120-min time-course experiments, in male C57BL/6J mice (in vivo glucose reduction); n = 8, all values are Mean ± SEM, via intraperitonial (i.p.) route of administration.

| Treatment group | 0 min | 30 min | 60 min | 120 min |
|---|---|---|---|---|
| C57 control | 183 ± 6.2 | 186 ± 6.1 | 188 ± 5.2 | 181 ± 5.4 |
| Exendin (2 nM/kg, i.p) | 182 ± 5.3 | 111 ± 4.2 | 128 ± 2.1 | 145 ± 1.2 |
| Seq. ID. 5 (50 nM/kg, i.p) | 181 ± 5.1 | 120 ± 3.8 | 128 ± 2.2 | 149 ± 1.6 |
| Seq. ID. 6 (50 nM/kg, i.p) | 180 ± 5.2 | 119 ± 3.2 | 129 ± 2.6 | 148 ± 1.8 |
| Seq. ID. 7 (50 nM/kg, i.p) | 182 ± 5.3 | 121 ± 3.3 | 127 ± 2.8 | 149 ± 2.0 |
| Seq. ID. 8 (50 nM/kg, i.p) | 183 ± 5.1 | 122 ± 3.1 | 130 ± 2.3 | 148 ± 2.2 |
| Seq. ID. 9 (50 nM/kg, i.p) | 180 ± 5.2 | 120 ± 2.9 | 138 ± 2.4 | 149 ± 2.0 |
| Seq. ID. 10 (50 nM/kg, i.p) | 181 ± 5.3 | 119 ± 3.0 | 128 ± 2.6 | 147 ± 1.9 |
| Seq. ID. 11 (50 nM/kg, i.p) | 179 ± 5.0 | 120 ± 3.6 | 129 ± 2.0 | 148 ± 1.7 |
| Seq. ID. 12 (50 nM/kg, i.p) | 184 ± 5.0 | 122 ± 3.8 | 128 ± 2.1 | 149 ± 2.3 |
| Seq. ID. 13 (30 nM/kg, i.p) | 182 ± 5.1 | 118 ± 2.1 | 116 ± 2.2 | 118 ± 2.4 |
| Seq. ID. 14 (30 nM/kg, i.p) | 181 ± 5.2 | 119 ± 2.6 | 117 ± 2.1 | 119 ± 2.3 |
| Seq. ID. 15 (30 nM/kg, i.p) | 180 ± 5.3 | 118 ± 2.8 | 118 ± 2.4 | 118 ± 2.1 |
| Seq. ID. 16 (30 nM/kg, i.p) | 183 ± 4.9 | 117 ± 2.5 | 116 ± 2.3 | 119 ± 2.0 |
| Seq. ID. 17 (30 nM/kg, i.p) | 182 ± 4.8 | 118 ± 2.8 | 116 ± 2.6 | 118 ± 1.2 |
| Seq. ID. 18 (30 nM/kg, i.p) | 181 ± 4.1 | 117 ± 3.8 | 117 ± 3.0 | 117 ± 1.6 |
| Seq. ID. 19 (30 nM/kg, i.p) | 180 ± 3.2 | 119 ± 3.2 | 117 ± 3.1 | 118 ± 1.8 |
| Seq. ID. 20 (30 nM/kg, i.p) | 183 ± 3.6 | 118 ± 3.3 | 116 ± 3.2 | 117 ± 1.9 |

TABLE 7-continued

Acute single dose 120-min time-course experiments, in male C57BL/6J mice (in vivo glucose reduction); n = 8, all values are Mean ± SEM, via intraperitonial (i.p.) route of administration.

| Treatment group | 0 min | 30 min | 60 min | 120 min |
|---|---|---|---|---|
| Seq. ID. 21 (20 nM/kg, i.p) | 182 ± 3.3 | 120 ± 3.6 | 127 ± 3.4 | 145 ± 2.1 |
| Seq. ID. 22 (20 nM/kg, i.p) | 181 ± 3.0 | 121 ± 3.4 | 128 ± 2.8 | 141 ± 2.3 |
| Seq. ID. 23 (20 nM/kg, i.p) | 180 ± 3.1 | 122 ± 3.9 | 129 ± 2.2 | 140 ± 2.9 |
| Seq. ID. 24 (20 nM/kg, i.p) | 179 ± 2.9 | 121 ± 3.0 | 129 ± 3.8 | 142 ± 1.6 |
| Seq. ID. 25 (20 nM/kg, i.p) | 182 ± 2.8 | 122 ± 3.2 | 128 ± 3.4 | 141 ± 1.7 |
| Seq. ID. 26 (20 nM/kg, i.p) | 181 ± 3.0 | 123 ± 3.8 | 128 ± 3.2 | 146 ± 1.8 |
| Seq. ID. 27 (20 nM/kg, i.p) | 183 ± 4.9 | 120 ± 2.8 | 129 ± 3.0 | 139 ± 2.0 |
| Seq. ID. 28 (20 nM/kg, i.p) | 182 ± 2.1 | 121 ± 2.9 | 130 ± 3.1 | 138 ± 2.4 |
| Seq. ID. 29 (10 nM/kg, i.p) | 180 ± 2.5 | 110 ± 2.6 | 111 ± 3.2 | 112 ± 2.3 |
| Seq. ID. 30 (10 nM/kg, i.p) | 182 ± 2.1 | 111 ± 2.1 | 112 ± 2.8 | 113 ± 2.2 |
| Seq. ID. 31 (10 nM/kg, i.p) | 183 ± 2.2 | 113 ± 2.8 | 113 ± 2.9 | 114 ± 2.0 |
| Seq. ID. 32 (10 nM/kg, i.p) | 182 ± 2.3 | 110 ± 2.3 | 112 ± 3.0 | 112 ± 1.9 |
| Seq. ID. 33 (10 nM/kg, i.p) | 181 ± 2.5 | 111 ± 3.4 | 113 ± 3.1 | 110 ± 1.8 |
| Seq. ID. 34 (10 nM/kg, i.p) | 180 ± 4.2 | 113 ± 3.2 | 112 ± 2.4 | 110 ± 1.9 |
| Seq. ID. 35 (10 nM/kg, i.p) | 182 ± 4.1 | 112 ± 3.1 | 113 ± 2.6 | 111 ± 1.8 |
| Seq. ID. 36 (10 nM/kg, i.p) | 180 ± 2.8 | 110 ± 3.6 | 112 ± 2.3 | 112 ± 1.6 |

TABLE 8

Acute single dose 120-min time-course experiments, in male C57BL/6J mice (in vivo glucose reduction), with selected peptidomimetics; n = 8, all values are Mean ± SEM, via oral route of administration

| Treatment group | 0 min | 30 min | 60 min | 120 min |
|---|---|---|---|---|
| C57 control | 183 ± 2.2 | 186 ± 3.1 | 189 ± 4.2 | 182 ± 2.4 |
| Seq. ID. 29 (2 µM/kg, oral) | 184 ± 2.5 | 115 ± 3.6 | 113 ± 4.2 | 110 ± 2.4 |
| Seq. ID. 30 (2 µM/kg, oral) | 183 ± 2.4 | 116 ± 3.1 | 112 ± 4.8 | 110 ± 2.5 |
| Seq. ID. 31 (2 µM/kg, oral) | 185 ± 2.3 | 115 ± 3.8 | 113 ± 4.9 | 109 ± 2.2 |
| Seq. ID. 32 (2 µM/kg, oral) | 181 ± 2.5 | 117 ± 3.3 | 112 ± 4.0 | 108 ± 2.9 |
| Seq. ID. 33 (2 µM/kg, oral) | 182 ± 2.5 | 116 ± 3.1 | 113 ± 4.1 | 110 ± 2.8 |
| Seq. ID. 34 (2 µM/kg, oral) | 184 ± 2.2 | 118 ± 3.3 | 112 ± 4.4 | 110 ± 2.9 |
| Seq. ID. 35 (2 µM/kg, oral) | 183 ± 2.1 | 118 ± 3.4 | 113 ± 4.6 | 111 ± 2.8 |
| Seq. ID. 36 (2 µM/kg, oral) | 183 ± 2.3 | 119 ± 3.0 | 112 ± 4.3 | 109 ± 2.6 |

Some of the baseline corrected serum glucose levels, as representative figures are shown, after single dose treatment with Seq. ID. No. 32, at different doses (DRC), either in C57, via ip (FIG. 8), oral (FIG. 9) or in db/db (FIG. 10) via oral route of administration, while FIG. 11 represent the change in serum insulin levels after single oral administration of vehicles/test compounds (Seq. ID. No. 30, 31 and 32), in C57BL/6J mice (in vivo).

Overview on In Vitro and In Vivo Results of Peptidomimetics:

As described above, all the peptidomimetics prepared in the present invention were evaluated in vitro and in vivo and the data of selected peptidomimetics were presented in above section as examples of representative peptidomimetics. In RIN 5F (rat insulinoma) cell based assay, all the peptidomimetics showed only glucose-dependent insulin secretion, in the range of 1-10 nM concentration (Table 3), thereby these class of peptidomimetics are likely to be devoid of hyperglycemic episodes, which is commonly observed with other class of insulin secretagogues, such as sulfonylureas. In human glucagon receptor assay, in vitro antagonistic activity of peptidomemtics were estimated by measuring the inhibition of amount of cAMP production, with test peptidomemtics, when incubated along with the glucagon peptide. As shown in the Table 5, in general, all the peptidomimetics showed significant glucagon receptor antagonistic activity, in the range of 1 nM to 1000 nM. In HGLP-1R assay, the novel peptidomimetics showed concentration dependent cAMP production (in vitro GLP-1 agonist activity), in the range of 1-100 nM concentration (Table 4). This dual nature of peptidomimetics (antagonist of the glucagon receptor and agonist of the GLP-1 receptor), make them ideal candidate for the safe and effective treatment of type 2 diabetes and associated metabolic disorders.

Stability study results of selected peptidomimetics against DPP-IV enzyme, human plasma, simulated gastric and intestinal fluid and liver microsomes, indicates that most of the peptidomimetics are stable against DPP-IV enzyme, when incubated upto 24 hrs. Similarly, in human plasma, simulated gastric and intestinal fluid, most of the peptidomimetics were found to be stable, when incubated upto 24 hrs. Incubation of peptidomimetics with liver microsomes showed significant stability and only 26-35% degradation were observed in 24 hrs, indicated that some of the peptidomimetics could be delivered by oral route of administration.

In vivo antihyperglycaemic/antidiabetic activity of peptidomimetics, both by parenteral and oral route of administration were determined in C57 or db/db mice, using acute-single-dose 120/240-min time course experiment. As shown in Table 7, most of the peptidomimetics are active via i.p. route of administration, in the dose range of 10-50 nM, while orally, some of the selected peptidomimetics (Table 8) are active in the range of 1-2 µM/kg dose. Thus novel peptidomimetics exhibit glucagon antagonistic and GLP-1 agonistic activity and are orally bioavailable, which make them ideal candidate for the safe and effective treatment of type 2 diabetes and associated metabolic disorders.

Utilities:

In a preferred embodiment, the present invention provides a method of making a peptidomimetic, that function both as an antagonist of the glucagon receptor and agonist of the GLP-1 receptor having different degree of affinity/selectivity towards both the receptors and useful for reducing circulating glucose levels & for the treatment of diabetes.

The synthetic peptidomimetics described in the present embodiment exhibit desirable in vitro Glucagon antagonistic and GLP-1 agonist activity in CHO cells transfected with human glucagon or HGLP-1R, in nM concentration, and in vivo, some of the peptidomimetics showed glucose dependent insulin release and reduces fasting hyperglycemia, without causing hypoglycemia, when tested in different diabetic animal models, such as hyperglycemic C57 mice and db/db mice.

Novel peptidomemtics of present invention showed increased stability against various proteolytic enzymes and due to increased stability and short chain length, such peptidomimetics can also be delivered by oral route of administration, along with other invensive and non-invensive routes of administration.

The novel peptidomimetics of the present invention can be formulated into suitable pharmaceutically acceptable compositions by combining with suitable excipients as are well known.

The pharmaceutical composition is provided by employing conventional techniques. Preferably the composition is in unit dosage form containing an effective amount of the active component, that is, the peptidomimetics of formula (I) either alone or combination, according to this invention.

The quantity of active component, that is, the peptidomimetics of formula (I) according to this invention, in the pharmaceutical composition and unit dosage form thereof may be varied or adjusted widely depending upon the particular application method, the potency of the particular peptidomimetics and the desired concentration. Generally, the quantity of active component will range between 0.5% to 90% by weight of the composition.

Accordingly, the peptidomimetics of the present invention can be administered to mammals, preferably humans, for the treatment of a variety of conditions and disorders, including, but not limited to, treating or delaying the progression or onset of diabetes (preferably type II, impaired glucose tolerance, insulin resistance and diabetic complications, such as nephropathy, retinopathy, neuropathy and cataracts), hyperglycemia, hyperinsulinemia, hypercholesterolemia, elevated blood levels of free fatty acids or glycerol, hyperlipidemia, hypertriglyceridemia, wound healing, tissue ischemia, atherosclerosis, hypertension, intestinal diseases (such as necrotizing enteritis, microvillus inclusion disease or celic disease). The peptidomimetics of the present invention may also be utilized to increase the blood levels of high-density lipoprotein (HDL).

In addition, the conditions, diseases collectively referenced to as 'Syndrome X' or metabolic syndrome as detailed in Johannsson G., J., Clin. Endocrinol. Metab., 1997, 82, 727, may be treated employing the peptidomimetics of the invention. The peptidomimetics of the present invention may optionally be used in combination with suitable DPP-IV inhibitors for the treatment of some of the above disease states either by administering the compounds sequentially or as a formulation containing the peptidomimetics of the present invention along with a suitable DPP-IV inhibitors.

No adverse effects were observed for any of the mentioned peptidomimetics of invention. The compounds of the present invention showed good glucose serum-lowering activity in the experimental animals used. These peptidomimetics are used for the testing/prophylaxis of diseases caused by hyperinsulinemia, hyperglycemia such as NIDDM, metabolic disorders, since such diseases are inter-linked to each other.

We claim:

1. An isolated peptidomimetic having a sequence of Formula (I), or a tautomer or solvate thereof;

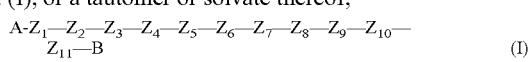

wherein, A represents the groups —NH—$R_1$, $R_3$—CO— or $R_3$—$SO_2$—, wherein $R_1$ represents hydrogen, or optionally substituted linear or branched ($C_1$-$C_{10}$) alkyl chain; $R_3$ is selected from linear or branched ($C_1$-$C_{10}$) alkyl, ($C_3$-$C_6$) cycloalkyl, aryl, heteroaryl or arylalkyl groups; B represents the groups —$COOR_2$, —$CONHR_2$ or $CH_2OR_2$ or a tetrazole, wherein $R_2$ represents H, optionally substituted groups selected from linear or branched ($C_1$-$C_{10}$) alkyl, aryl or aralkyl groups; $Z_1$ represents Histidine; $Z_2$ represents a naturally or unnaturally occurring amino acid selected from the group comprising L-Serine, D-Serine, L-alanine, D-alanine, α-amino-isobutyric acid, and 1-amino cyclopropane carboxyl acid; $Z_3$ represents glutamine (Gln; Q) or compounds of formula II;

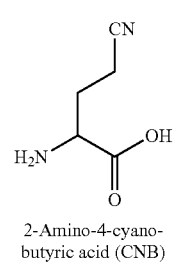

2-Amino-4-cyano-butyric acid (CNB)

$Z_4$ represents glycine or the group 1-amino cyclopropane carboxylic acid; $Z_5$ represents a naturally or non-naturally occurring amino acid comprising a hydroxyl side chain; $Z_6$ represents, a naturally of unnaturally occurring amino acid having a disubstituted alpha carbon having two side chains, wherein each of them are independently selected from an optionally substituted alkyl, aryl or an aralkyl group wherein the substituents are selected from one or more alkyl groups or one or more halo groups;

$Z_7$ and $Z_8$ independently represents a naturally or non-naturally occurring amino acid comprising a hydroxyl side chain; $Z_9$ independently represents a naturally or non-naturally occurring amino acid having an amino acid side chain comprising an acidic group;

$Z_{10}$ represents a naturally or unnaturally occurring amino acid of formula IV

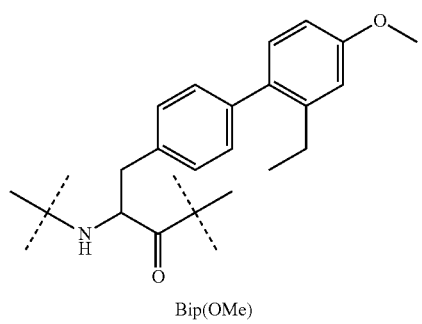

Bip(OMe)

Formula IV and $Z_{11}$ represents a naturally or unnaturally occurring amino acid of formula V(a-d)

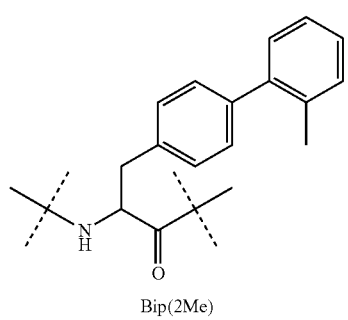

Bip(2Me)

Formula Va

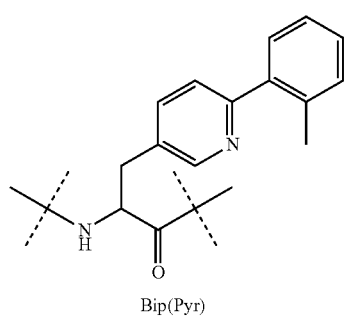

Bip(Pyr)

Formula Vb

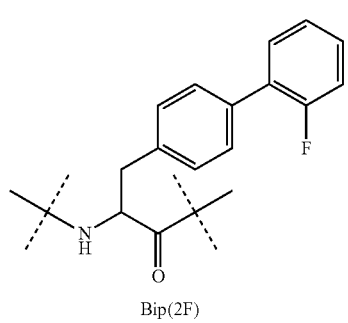

Bip(2F)

Formula Vc

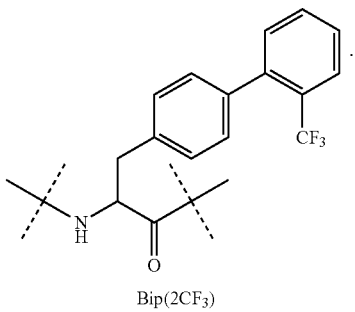

Bip(2CF₃)

Formula Vd

2. The compound of formula I as claimed in claim 1, wherein $Z_5$ is threonine.

3. The compound of formula I as claimed in claim 1, wherein $Z_5$ represents a compound of formula III

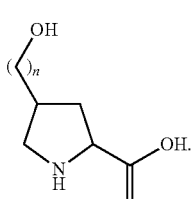

$n = 0$ or $1$
4-Hydroxy-pyrrolidine-2-carboxylic acid (PCA)

Formula III

4. The compound of formula I as claimed in claim 1, wherein $Z_6$ represents Phe (F), alpha-methyl-phenylalanine (-α-Me-Phe-), alpha-methyl-2-fluorophenylalanine (-α-Me-2F-Phe-), alpha-methyl-2,6-diflurophenylalanine (-α-Me-2,6-F-Phe-) or 2-fluorophenylalanine (-2F-Phe-).

5. The compound of formula I as claimed in claim 1 wherein each of $Z_7$ and $Z_8$ is independently selected from threonin, serine, 1-amino cyclopropane carboxylic acid or a compound of formula III

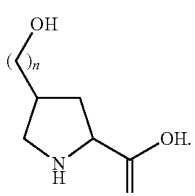

$n = 0$ or $1$
4-Hydroxy-pyrrolidine-2-carboxylic acid (PCA)

6. The compound of formula I as claimed in claim 1, wherein $Z_9$ is selected from aspartic acid or a compound of formula II

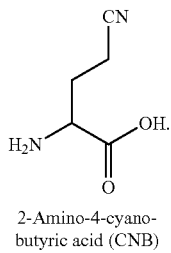

Formula II

2-Amino-4-cyano-
butyric acid (CNB)

7. The compound of formula I

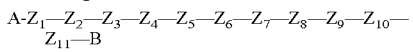

wherein
- A represents the groups —NH—$R_1$, $R_3$—CO— or $R_3$—$SO_2$—, wherein $R_1$ represents hydrogen, or optionally substituted linear or branched ($C_1$-$C_{10}$) alkyl chain, $R_3$ is selected from linear or branched ($C_1$-$C_{10}$) alkyl, ($C_3$-$C_6$) cycloalkyl, aryl, heteroaryl or arylalkyl groups;
- B represents —$COOR_2$, —$CONHR_2$ or $CH_2OR_2$ or a tetrazole, wherein $R_2$ represents H, optionally substituted groups selected from linear or branched ($C_1$-$C_{10}$) alkyl group, aryl or aralkyl groups; $Z_1$ represents Histidine (H); $Z_2$ is selected from L-Serine, D-Serine, L-alanine, D-alanine, α-amino-isobutyric acid, I-amino cyclopropane carboxylic acid; $Z_3$ represents glutamine (Gln; Q) or a compound of formula II

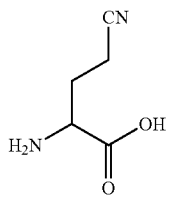

Formula II

2-Amino-4-cyano-
butyric acid (CNB)

$Z_4$ represents glycine or the group 1-amino cyclopropane carboxylic acid; $Z_5$ is selected from threonine or compounds of formula III

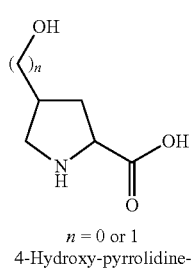

Formula III n = 0 or 1
4-Hydroxy-pyrrolidine-
2-carboxylic
acid (PCA)

$Z_6$ is selected from Phe (F), alpha-methyl-phenylalanine (-α-Me-Phe-), alpha-methyl-2-fluorophenylalanine (-α-Me-2F-Phe-), alpha-methyl-2,6-diflurophenylalanine (-α-Me-2,6-F-Phe-) or 2-fluorophenylalanine (-2F-Phe-); $Z_7$ and $Z_8$ each is independently selected from threonine, serine, 1-amino cyclopropane carboxylic acid or compound of formula III as defined earlier; $Z_9$ is selected from Aspartic acid or compounds of formula II as defined earlier; $Z_{10}$ represents a naturally or unnaturally occurring amino acid of formula IV

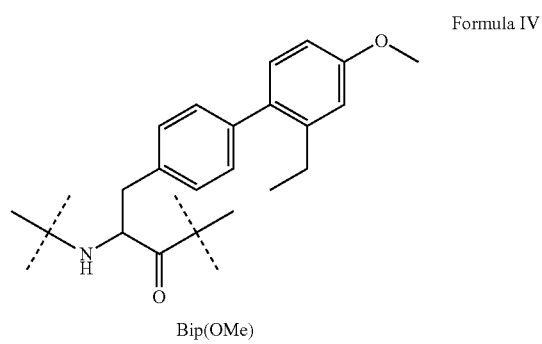

Formula IV

Bip(OMe)

and $Z_{11}$ selected from amino acids of formula V (a-d)

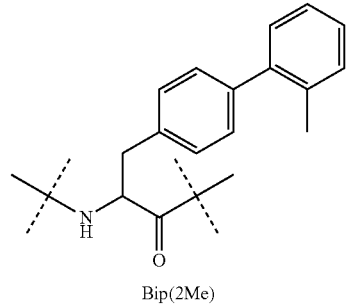

Formula Va

Bip(2Me)

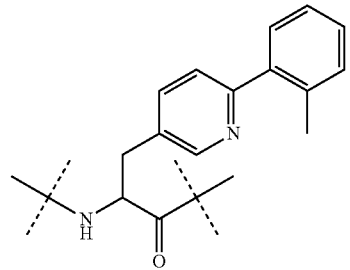

Formula Vb

Bip(Pyr)

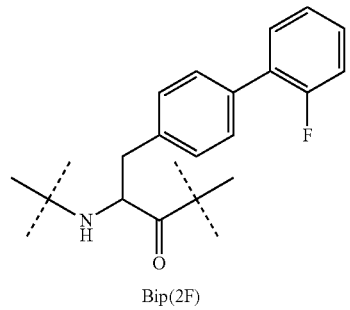

Formula Vc

Bip(2F)

Formula Vd

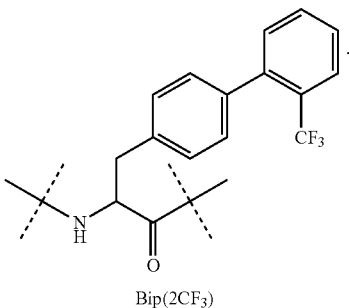
Bip(2CF₃)

8. The compound of formula I as claimed in claim 1, wherein the aryl group is selected from phenyl, napthyl, indanyl, fluorenyl and biphenyl groups.

9. The compound of formula I as claimed in claim 1, wherein the heteroaryl group is selected from pyridyl, thienyl, furyl, imidazolyl, and benzofuranyl groups.

10. A compound selected from:

```
HSQGTFTSD-Bip(OMe)-Bip(2Me);
HSQGTFTSD-Bip(OMe)-Bip(Pyr);
HSQGTFTSD-Bip(OMe)-Bip(2F);
HSQGTFTSD-Bip(OMe)-Bip(2CF₃);
HAQGTFTSD-Bip(OMe)-Bip(2Me);
HAQGTFTSD-Bip(OMe)-Bip(Pyr);
HAQGTFTSD-Bip(OMe)-Bip(2F);
HAQGTFTSD-Bip(OMe)-Bip(2CF₃);
H-Aib-QGTFTSD-Bip(OMe)-Bip(2Me);
H-Aib-QGTFTSD-Bip(OMe)-Bip(Pyr);
H-Aib-QGTFTSD-Bip(OMe)-Bip(2F);
H-Aib-QGTFTSD-Bip(OMe)-Bip(2CF₃);
H-(ACP)-QGTFTSD-Bip(OMe)-Bip(2Me);
H-(ACP)-QGTFTSD-Bip(OMe)-Bip(Pyr);
H-(ACP)-QGTFTSD-Bip(OMe)-Bip(2F);
H-(ACP)-QGTFTSD-Bip(OMe)-Bip(2CF₃);
HSQGT-(α-Me-2F-Phe)-TSD-Bip(OMe)-Bip(2Me);
HSQGT-(α-Me-2F-Phe)-TSD-Bip(OMe)-Bip(Pyr);
HSQGT-(α-Me-2F-Phe)-TSD-Bip(OMe)-Bip(2F);
HSQGT-(α-Me-2F-Phe)-TSD-Bip(OMe)-Bip(2CF₃);
HAQGT-(α-Me-2F-Phe)-TSD-Bip(OMe)-Bip(2Me);
HAQGT-(α-Me-2F-Phe)-TSD-Bip(OMe)-Bip(Pyr);
HAQGT-(α-Me-2F-Phe)-TSD-Bip(OMe)-Bip(2F);
HAQGT-(α-Me-2F-Phe)-TSD-Bip(OMe)-Bip(2CF₃);
H-Aib-QGT-(α-Me-2F-Phe)-TSD-Bip(OMe)-Bip(2Me);
H-Aib-QGT-(α-Me-2F-Phe)-TSD-Bip(OMe)-Bip(Pyr);
H-Aib-QGT-(α-Me-2F-Phe)-TSD-Bip(OMe)-Bip(2F);
H-Aib-QGT-(α-Me-2F-Phe)-TSD-Bip(OMe)-Bip(2CF₃);
H-(ACP)-QGT-(α-Me-2F-Phe)-TSD-Bip(OMe)-Bip(2Me);
H-(ACP)-QGT-(α-Me-2F-Phe)-TSD-Bip(OMe)-Bip(Pyr);
H-(ACP)-QGT-(α-Me-2F-Phe)-TSD-Bip(OMe)-Bip(2F);
H-(ACP)-QGT-(α-Me-2F-Phe)-TSD-Bip(OMe)-Bip(2CF₃);
HSQGT-(2F-Phe)-TSD-Bip(OMe)-Bip(2Me);
HSQGT-(2F-Phe)-TSD-Bip(OMe)-Bip(Pyr);
HSQGT-(2F-Phe)-TSD-Bip(OMe)-Bip(2F);
HSQGT-(☐F-Phe)-TSD-Bip(OMe)-Bip(2CF₃);
HAQGT-(2F-Phe)-TSD-Bip(OMe)-Bip(2Me);
HAQGT-(2F-Phe)-TSD-Bip(OMe)-Bip(Pyr);
HAQGT-(2F-Phe)-TSD-Bip(OMe)-Bip(2F);
HAQGT-(2F-Phe)-TSD-Bip(OMe)-Bip(2CF₃);
H-Aib-QGT-(2F-Phe)-TSD-Bip(OMe)-Bip(2Me);
H-Aib-QGT-(2F-Phe)-TSD-Bip(OMe)-Bip(Pyr);
H-Aib-QGT-(2F-Phe)-TSD-Bip(OMe)-Bip(2F);
H-Aib-QGT-(2F-Phe)-TSD-Bip(OMe)-Bip(2CF₃);
H-(ACP)-QGT-(2F-Phe)-TSD-Bip(OMe)-Bip(2Me);
H-(ACP)-QGT-(2F-Phe)-TSD-Bip(OMe)-Bip(Pyr);
H-(ACP)-QGT-(2F-Phe)-TSD-Bip(OMe)-Bip(2F);
H-(ACP)-QGT-(2F-Phe)-TSD-Bip(OMe)-Bip(2CF₃);
HS-(CNB)-GTFTSD-Bip(OMe)-Bip(2Me);
HS-(CNB)-GTFTSD-Bip(OMe)-Bip(Pyr);
HS-(CNB)-GTFTSD-Bip(OMe)-Bip(2F);
HS-(CNB)-GTFTSD-Bip(OMe)-Bip(2CF₃);
HA-(CNB)-GTFTSD-Bip(OMe)-Bip(2Me);
HA-(CNB)-GTFTSD-Bip(OMe)-Bip(Pyr);
HA-(CNB)-GTFTSD-Bip(OMe)-Bip(2F);
HA-(CNB)-GTFTSD-Bip(OMe)-Bip(2CF₃);
H-Aib-(CNB)-GTFTSD-Bip(OMe)-Bip(2Me);
H-Aib-(CNB)-GTFTSD-Bip(OMe)-Bip(Pyr);
H-Aib-(CNB)-GTFTSD-Bip(OMe)-Bip(2F);
H-Aib-(CNB)-GTFTSD-Bip(OMe)-Bip(2CF₃);
H-(ACP)-(CNB)-GTFTSD-Bip(OMe)-Bip(2Me);
H-(ACP)-(CNB)-GTFTSD-Bip(OMe)-Bip(Pyr);
H-(ACP)-(CNB)-GTFTSD-Bip(OMe)-Bip(2F);
H-(ACP)-(CNB)-GTFTSD-Bip(OMe)-Bip(2CF₃);
HS-(CNB)-GT-(α-Me-2F-Phe)-TSD-Bip(OMe)-Bip(2Me);
HS-(CNB)-GT-(α-Me-2F-Phe)-TSD-Bip(OMe)-Bip(Pyr);
HS-(CNB)-GT-(α-Me-2F-Phe)-TSD-Bip(OMe)-Bip(2F);
```

-continued

HS-(CNB)-GT-(α-Me-2F-Phe)-TSD-Bip(OMe)-Bip(2CF₃);

HA-(CNB)-GT-(α-Me-2F-Phe)-TSD-Bip(OMe)-Bip(2Me);

HA-(CNB)-GT-(α-Me-2F-Phe)-TSD-Bip(OMe)-Bip(Pyr);

HA-(CNB)-GT-(α-Me-2F-Phe)-TSD-Bip(OMe)-Bip(2F);

HA-(CNB)-GT-(α-Me-2F-Phe)-TSD-Bip(OMe)-Bip(2CF₃);

H-Aib-(CNB)-GT-(α-Me-2F-Phe)-TSD-Bip(OMe)-Bip(2Me);

H-Aib-(CNB)-GT-(α-Me-2F-Phe)-TSD-Bip(OMe)-Bip(Pyr);

H-Aib-(CNB)-GT-(α-Me-2F-Phe)-TSD-Bip(OMe)-Bip(2F);

H-Aib-(CNB)-GT-(α-Me-2F-Phe)-TSD-Bip(OMe)-Bip(2CF₃);

H-(ACP)-(CNB)-GT-(α-Me-2F-Phe)-TSD-Bip(OMe)-Bip(2Me);

H-(ACP)-(CNB)-GT-(α-Me-2F-Phe)-TSD-Bip(OMe)-Bip(Pyr);

H-(ACP)-(CNB)-GT-(α-Me-2F-Phe)-TSD-Bip(OMe)-Bip(2F);

H-(ACP)-(CNB)-GT-(α-Me-2F-Phe)-TSD-Bip(OMe)-Bip(2CF₃);

HS-(CNB)-GT-(2F-Phe)-TSD-Bip(OMe)-Bip(2Me);

HS-(CNB)-GT-(2F-Phe)-TSD-Bip(OMe)-Bip(Pyr);

HS-(CNB)-GT-(2F-Phe)-TSD-Bip(OMe)-Bip(2F);

HS-(CNB)-GT-(☐F-Phe)-TSD-Bip(OMe)-Bip(2CF₃);

HA-(CNB)-GT-(2F-Phe)-TSD-Bip(OMe)-Bip(2Me);

HA-(CNB)-GT-(2F-Phe)-TSD-Bip(OMe)-Bip(Pyr);

HA-(CNB)-GT-(2F-Phe)-TSD-Bip(OMe)-Bip(2F);

HA-(CNB)-GT-(2F-Phe)-TSD-Bip(OMe)-Bip(2CF₃);

H-Aib-(CNB)-GT-(2F-Phe)-TSD-Bip(OMe)-Bip(2Me);

H-Aib-(CNB)-GT-(2F-Phe)-TSD-Bip(OMe)-Bip(Pyr);

H-Aib-(CNB)-GT-(2F-Phe)-TSD-Bip(OMe)-Bip(2F);

H-Aib-(CNB)-GT-(2F-Phe)-TSD-Bip(OMe)-Bip(2CF₃);

H-(ACP)-(CNB)-GT-(2F-Phe)-TSD-Bip(OMe)-Bip(2Me);

H-(ACP)-(CNB)-GT-(2F-Phe)-TSD-Bip(OMe)-Bip(Pyr);

H-(ACP)-(CNB)-GT-(2F-Phe)-TSD-Bip(OMe)-Bip(2F);

H-(ACP)-(CNB)-GT-(2F-Phe)-TSD-Bip(OMe)-Bip(2CF₃);

HSQ-(ACP)-TFTSD-Bip(OMe)-Bip(2Me);

HSQ-(ACP)-TFTSD-Bip(OMe)-Bip(Pyr);

HSQ-(ACP)-TFTSD-Bip(OMe)-Bip(2F);

HSQ-(ACP)-TFTSD-Bip(OMe)-Bip(2CF₃);

HAQ-(ACP)-TFTSD-Bip(OMe)-Bip(2Me);

HAQ-(ACP)-TFTSD-Bip(OMe)-Bip(Pyr);

HAQ-(ACP)-TFTSD-Bip(OMe)-Bip(2F);

HAQ-(ACP)-TFTSD-Bip(OMe)-Bip(2CF₃);

H-Aib-Q-(ACP)-TFTSD-Bip(OMe)-Bip(2Me);

H-Aib-Q-(ACP)-TFTSD-Bip(OMe)-Bip(Pyr);

H-Aib-Q-(ACP)-TFTSD-Bip(OMe)-Bip(2F);

H-Aib-Q-(ACP)-TFTSD-Bip(OMe)-Bip(2CF₃);

H-(ACP)-Q-(ACP)-TFTSD-Bip(OMe)-Bip(2Me);

H-(ACP)-Q-(ACP)-TFTSD-Bip(OMe)-Bip(Pyr);

H-(ACP)-Q-(ACP)-TFTSD-Bip(OMe)-Bip(2F);

H-(ACP)-Q-(ACP)-TFTSD-Bip(OMe)-Bip(2CF₃);

HSQ-(ACP)-T-(α-Me-2F-Phe)-TSD-Bip(OMe)-Bip(2Me);

HSQ-(ACP)-T-(α-Me-2F-Phe)-TSD-Bip(OMe)-Bip(Pyr);

HSQ-(ACP)-T-(α-Me-2F-Phe)-TSD-Bip(OMe)-Bip(2F);

HSQ-(ACP)-T-(α-Me-2F-Phe)-TSD-Bip(OMe)-Bip(2CF₃);

HAQ-(ACP)-T-(α-Me-2F-Phe)-TSD-Bip(OMe)-Bip(2Me);

HAQ-(ACP)-T-(α-OMe-2F-Phe)-TSD-Bip(OMe)-Bip(Pyr);

HAQ-(ACP)-T-(α-Me-2F-Phe)-TSD-Bip(OMe)-Bip(2F);

HAQ-(ACP)-T-(α-Me-2F-Phe)-TSD-Bip(OMe)-Bip(2CF₃);

H-Aib-Q-(ACP)-T-(α-Me-2F-Phe)-TSD-Bip(OMe)-Bip(2Me);

H-Aib-Q-(ACP)-T-(α-Me-2F-Phe)-TSD-Bip(OMe)-Bip(Pyr);

H-Aib-Q-(ACP)-T-(α-Me-2F-Phe)-TSD-Bip(OMe)-Bip(2F);

H-Aib-Q-(ACP)-T-(α-Me-2F-Phe)-TSD-Bip(OMe)-Bip(2CF₃);

H-(ACP)-Q-(ACP)-T-(α-Me-2F-Phe)-TSD-Bip(OMe)-Bip(2Me);

H-(ACP)-Q-(ACP)-T-(α-Me-2F-Phe)-TSD-Bip(OMe)-Bip(Pyr);

H-(ACP)-Q-(ACP)-T-(α-Me-2F-Phe)-TSD-Bip(OMe)-Bip(2F);

H-(ACP)-Q-(ACP)-T-(α-Me-2F-Phe)-TSD-Bip(OMe)-Bip(2CF₃);

HSQ-(ACP)-T-(2F-Phe)-TSD-Bip(OMe)-Bip(2Me);

HSQ-(ACP)-T-(2F-Phe)-TSD-Bip(OMe)-Bip(Pyr);

HSQ-(ACP)-T-(2F-Phe)-TSD-Bip(OMe)-Bip(2F);

HSQ-(ACP)-T-(☐F-Phe)-TSD-Bip(OMe)-Bip(2CF₃);

HAQ-(ACP)-T-(2F-Phe)-TSD-Bip(OMe)-Bip(2Me);

HAQ-(ACP)-T-(2F-Phe)-TSD-Bip(OMe)-Bip(Pyr);

HAQ-(ACP)-T-(2F-Phe)-TSD-Bip(OMe)-Bip(2F);

HAQ-(ACP)-T-(2F-Phe)-TSD-Bip(OMe)-Bip(2CF₃);

H-Aib-Q-(ACP)-T-(2F-Phe)-TSD-Bip(OMe)-Bip(2Me);

H-Aib-Q-(ACP)-T-(2F-Phe)-TSD-Bip(OMe)-Bip(Pyr);

H-Aib-Q-(ACP)-T-(2F-Phe)-TSD-Bip(OMe)-Bip(2F);

H-Aib-Q-(ACP)-T-(2F-Phe)-TSD-Bip(OMe)-Bip(2CF₃);

-continued

H-(ACP)-Q-(ACP)-T-(2F-Phe)-TSD-Bip(OMe)-Bip(2Me);

H-(ACP)-Q-(ACP)-T-(2F-Phe)-TSD-Bip(OMe)-Bip(Pyr);

H-(ACP)-Q-(ACP)-T-(2F-Phe)-TSD-Bip(OMe)-Bip(2F);

H-(ACP)-Q-(ACP)-T-(2F-Phe)-TSD-Bip(OMe)-Bip(2CF₃);

HSQG-(PCA)-FTSD-Bip(OMe)-Bip(2Me);

HSQG-(PCA)-FTSD-Bip(OMe)-Bip(Pyr);

HSQG-(PCA)-FTSD-Bip(OMe)-Bip(2F);

HSQG-(PCA)-FTSD-Bip(OMe)-Bip(2CF₃);

HAQG-(PCA)-FTSD-Bip(OMe)-Bip(2Me);

HAQG-(PCA)-FTSD-Bip(OMe)-Bip(Pyr);

HAQG-(PCA)-FTSD-Bip(OMe)-Bip(2F);

HAQG-(PCA)-FTSD-Bip(OMe)-Bip(2CF₃);

H-Aib-QG-(PCA)-FTSD-Bip(OMe)-Bip(2Me);

H-Aib-QG-(PCA)-FTSD-Bip(OMe)-Bip(Pyr);

H-Aib-QG-(PCA)-FTSD-Bip(OMe)-Bip(2F);

H-Aib-QG-(PCA)-FTSD-Bip(OMe)-Bip(2CF₃);

H-(ACP)-QG-(PCA)-FTSD-Bip(OMe)-Bip(2Me);

H-(ACP)-QG-(PCA)-FTSD-Bip(OMe)-Bip(Pyr);

H-(ACP)-QG-(PCA)-FTSD-Bip(OMe)-Bip(2F);

H-(ACP)-QG-(PCA)-FTSD-Bip(OMe)-Bip(2CF₃);

HSQG-(PCA)-(α-Me-2F-Phe)-TSD-Bip(OMe)-Bip(2Me);

HSQG-(PCA)-(α-Me-2F-Phe)-TSD-Bip(OMe)-Bip(Pyr);

HSQG-(PCA)-(α-Me-2F-Phe)-TSD-Bip(OMe)-Bip(2F);

HSQG-(PCA)-(α-Me-2F-Phe)-TSD-Bip(OMe)-Bip(2CF₃);

HAQG-(PCA)-(α-Me-2F-Phe)-TSD-Bip(OMe)-Bip(2Me);

HAQG-(PCA)-(α-Me-2F-Phe)-TSD-Bip(OMe)-Bip(Pyr);

HAQG-(PCA)-(α-Me-2F-Phe)-TSD-Bip(OMe)-Bip(2F);

HAQG-(PCA)-(α-Me-2F-Phe)-TSD-Bip(OMe)-Bip(2CF₃);

H-Aib-QG-(PCA)-(α-Me-2F-Phe)-TSD-Bip(OMe)-Bip(2Me);

H-Aib-QG-(PCA)-(α-Me-2F-Phe)-TSD-Bip(OMe)-Bip(Pyr);

H-Aib-QG-(PCA)-(α-Me-2F-Phe)-TSD-Bip(OMe)-Bip(2F);

H-Aib-QG-(PCA)-(α-Me-2F-Phe)-TSD-Bip(OMe)-Bip(2CF₃);

H-(ACP)-QG-(PCA)-(α-Me-2F-Phe)-TSD-Bip(OMe)-Bip(2Me);

H-(ACP)-QG-(PCA)-(α-Me-2F-Phe)-TSD-Bip(OMe)-Bip(Pyr);

H-(ACP)-QG-(PCA)-(α-Me-2F-Phe)-TSD-Bip(OMe)-Bip(2F);

H-(ACP)-QG-(PCA)-(α-Me-2F-Phe)-TSD-Bip(OMe)-Bip(2CF₃);

-continued

HSQG-(PCA)-(2F-Phe)-TSD-Bip(OMe)-Bip(2Me);

HSQG-(PCA)-(2F-Phe)-TSD-Bip(OMe)-Bip(Pyr);

HSQG-(PCA)-(2F-Phe)-TSD-Bip(OMe)-Bip(2F);

HSQG-(PCA)-(2F-Phe)-TSD-Bip(OMe)-Bip(2CF₃);

HAQG-(PCA)-(2F-Phe)-TSD-Bip(OMe)-Bip(2Me);

HAQG-(PCA)-(2F-Phe)-TSD-Bip(OMe)-Bip(Pyr);

HAQG-(PCA)-(2F-Phe)-TSD-Bip(OMe)-Bip(2F);

HAQG-(PCA)-(2F-Phe)-TSD-Bip(OMe)-Bip(2CF₃);

H-Aib-QG-(PCA)-(2F-Phe)-TSD-Bip(OMe)-Bip(2Me);

H-Aib-QG-(PCA)-(2F-Phe)-TSD-Bip(OMe)-Bip(Pyr);

H-Aib-QG-(PCA)-(2F-Phe)-TSD-Bip(OMe)-Bip(2F);

H-Aib-QG-(PCA)-(2F-Phe)-TSD-Bip(OMe)-Bip(2CF₃);

H-(ACP)-QG-(PCA)-(2F-Phe)-TSD-Bip(OMe)-Bip(2Me);

H-(ACP)-QG-(PCA)-(2F-Phe)-TSD-Bip(OMe)-Bip(Pyr);

H-(ACP)-QG-(PCA)-(2F-Phe)-TSD-Bip(OMe)-Bip(2F); and

H-(ACP)-QG-(PCA)-(2F-Phe)-TSD-Bip(OMe)-Bip(2CF₃).

11. A pharmaceutical composition comprising a compound of formula (I) as claimed in claim 1, and a pharmaceutically acceptable carrier(s).

12. A method of treating a disease caused by hyperlipidaemia, hypercholesteremia, hyperglycemia, hyperinsulinemia, elevated blood levels of free fatty acids or glycerol, hypertriglyceridemia, wound healing, impaired glucose tolerance, leptin resistance, insulin resistance or other diabetic complication comprising administering an effective, non-toxic amount of compound of formula (I) as claimed in claim 1 to a patient in need thereof.

13. The method according to claim 12, wherein the disease is type 2 diabetes, impaired glucose tolerance, dyslipidaemia, hypertension, atherosclerosis, hyperlipidaemia, coronary artery disease, cardiovascular disorders and other diseases wherein insulin resistance is the underlying pathophysiological mechanism.

14. A pharmaceutical composition comprising a compound as claimed in claim 10 and a pharmaceutically acceptable carrier(s).

15. A method of treating a disease caused by hyperlipidaemia, hypercholesteremia, hyperglycemia, hyperinsulinemia, elevated blood levels of free fatty acid or glycerol, hypertriglyceridemia, wound healing, impaired glucose tolerance, leptin resistance, insulin resistance or other diabetic complication comprising administering an effective, non-toxic amount of compound as defined in claim 10 to a patient in need thereof.

16. The method according to claim 15, wherein the disease is type 2 diabetes, impaired glucose tolerance, dyslipidaemia, hypertension, atherosclerosis, hyperlipidaemia, coronary artery disease, cardiovascular disorders and other diseases wherein insulin resistance is the underlying pathophysiological mechanism.

17. A method of treating a disease caused by hyperlipidaemia, hypercholesteremia, hyperglycemia, hyperinsulinemia, elevated blood levels of free fatty acids or glycerol, hypertriglyceridemia, wound healing, impaired glucose tolerance, leptin resistance, insulin resistance or other diabetic complication comprising administering an effective, non-toxic amount of a composition according to claim 11 to a patient in need thereof.

18. The method according to claim 17, wherein the disease is type 2 diabetes, impaired glucose tolerance, dyslipidaemia, hypertension, atherosclerosis, hyperlipidaemia, coronary artery disease, cardiovascular disorders and other diseases wherein insulin resistance is the underlying pathophysiological mechanism.

19. A method of treating a disease caused by hyperlipidaemia, hypercholesteremia, hyperglycemia, hyperinsulinemia, elevated blood levels of free fatty acids or glycerol, hypertriglyceridemia, wound healing, impaired glucose tolerance, leptin resistance, insulin resistance or other diabetic complication comprising administering an effective, non-toxic amount of a composition as claimed in claim 14 to a patient in need thereof.

20. The method according to claim 19, wherein the disease is type 2 diabetes, impaired glucose tolerance, dyslipidaemia, hypertension, atherosclerosis, hyperlipidaemia, coronary artery disease, cardiovascular disorders and other diseases wherein insulin resistance is the underlying pathophysiological mechanism.

\* \* \* \* \*